(12) United States Patent
Allen

(10) Patent No.: US 6,294,168 B1
(45) Date of Patent: Sep. 25, 2001

(54) METHOD FOR INHIBITING PATHOGENIC MICROBES IN AN ANIMAL USING A HALOPEROXIDASE-HALIDE-PEROXIDE SYSTEM

(75) Inventor: Robert Charles Allen, San Antonio, TX (US)

(73) Assignee: ExOxEmis, Inc., Little Rock, AR (US)

(*) Notice: Subject to any disclaimer, the term of this patent is extended or adjusted under 35 U.S.C. 154(b) by 0 days.

(21) Appl. No.: 08/271,583

(22) Filed: Jul. 7, 1994

Related U.S. Application Data

(63) Continuation of application No. 08/137,817, filed on Oct. 19, 1993, now abandoned, which is a continuation of application No. 07/660,994, filed on Feb. 21, 1991, now abandoned.

(51) Int. Cl.$^7$ .............................. A61K 38/44; C12N 9/08

(52) U.S. Cl. .......................................... 424/94.4; 435/192

(58) Field of Search ........................ 424/94.4; 435/189, 435/192; 422/28

(56) References Cited

U.S. PATENT DOCUMENTS

| | | | |
|---|---|---|---|
| 2,679,533 | 5/1954 | Darragh et al. | 564/282 |
| 4,473,500 | * 9/1984 | Rosenbaum et al. | 424/94.4 |
| 4,588,586 | * 5/1986 | Kessler et al. | 435/78 |
| 4,726,948 | * 2/1988 | Prieels et al. | 424/94.4 |
| 4,937,072 | * 6/1990 | Kessler et al. | 424/94.4 |
| 4,996,146 | 2/1991 | Kessler | 435/28 |

FOREIGN PATENT DOCUMENTS

| | | |
|---|---|---|
| 098073 | 1/1984 | (EP). |
| 361908 | 4/1990 | (EP). |
| 0361908 | * 4/1990 | (EP). |
| 397227 | 11/1990 | (EP). |
| 2108387 | 5/1983 | (GB). |
| WO8802600 | 4/1988 | (WO). |
| WO89/12457 | 12/1989 | (WO). |

OTHER PUBLICATIONS

H. Rosen et al., Formation of Singlet Oxygen by the Myelo Peroxidase Mediated Anti Microbial System, Biological Abstract No. 65021608 and J. Biol. Chem., vol. 252, No. 14, 1977, pp. 4803–4810.

E.L. Thomas et al., Oxidation of Chloride and Thiocyanate by Isolated Leukocytes, Biological Abstract No. 82079537 & J. Biol. Chem. vol. 261, No. 21, 1986, pp. 9694–9702.

Clark et al, Blood, 45(2), p. 161–170, Feb. 1975 (Biosis abstract only).*

Klebanoff, "Myeloperoxidase–Halide–Hydrogen Peroxide Antibacterial System," *J. Bacteriol.*, 95, 2131–2138, 1968.

Allen, R.C., Dissertation entitled Studies on the Generation of Electronic Excitation States in Human Polymorphonuclear Leukocytes and their Participation in Microbicidal Activity, Jul., 1973.

Allen, R.C. et al., "Evidence for the Generation of an Electronic Excitation State(s) in Human Polymorphonuclear Leukocytes and its Participation in Bactericidal Activity", *Biochemical and Biophysical Research Communications*, 47(4), 679–684, 1972.

Allen, R.C., "Halide Dependence of the Myeloperoxidase–mediated Antimicrobial System of the Polymorphonuclear Leukocyte in the Phenomenon of Electronic Excitation", *Biochemical and Biophysical Research Communications*, 63(3), 675–683, 1975.

Allen, R.C., "The Role of pH in the Chemiluminescent Response of the Myeloperoxidase–Halide–HOOH Antimicrobial System", *Biochemical and Biophysical Research Communications*, 63(3), 684–691, 1975.

Allen, R.C. and L.D. Loose, "Phagocytic Activation of a Luminol–Dependent Chemiluminescence in Rabbit Alveolar and Peritoneal Macrophages", *Biochemical and Biophysical Research Communications*, 69(1), 245–252, 1976.

Allen, R.C., "Evaluation of Serum Opsonic Capacity by Quantitating the Initial Chemiluminescent Response from Phagocytizing Polymorphonuclear Leukocytes", *Infection and Immunity*, 15(3), 828–833, 1977.

Allen, R.C. et al., "Correlation of Metabolic and Chemiluminescent Responses of Granulocytes from Three Female Siblings with Chronic Granulomatous Disease", *Journal of Infectious Diseases*, 136(4), 510–518, 1977.

(List continued on next page.)

*Primary Examiner*—David M. Naff
*Assistant Examiner*—Mike Meller
(74) *Attorney, Agent, or Firm*—Christensen O'Connor Johnson Kindness PLLC

(57) ABSTRACT

Haloperoxidases are used to selectively bind to and, in the presence of peroxide and halide, inhibit the growth of target microbes without eliminating desirable microbes or significantly damaging other components, such as host cells, in the environment of the target microbe. When a target microbe, e.g., a pathogenic microbe, has a binding capacity for haloperoxidase greater than that of a desired microbe, e.g., members of the normal flora, the target microbe selectively binds the haloperoxidase with little or no binding of the haloperoxidase by the desired microbe. In the presence of peroxide and halide, the target bound haloperoxidase catalyzes halide oxidation and facilitates the disproportionation of peroxide to singlet molecular oxygen at the surface of the target microbe. The lifetime of singlet molecular oxygen restricts damage to the surface resulting in selective killing of the target microbe with a minimum of collateral damage to the desired microbe or physiological medium. Methods and compositions provided are highly useful in the therapeutic or prophylactic antiseptic treatment of human or animal subjects, since their use can be designed to be highly effective in combatting bacterial or fungal infections without significant damage to normal flora or host cells. Suitable haloperoxidases include myeloperoxidase (MPO), eosinophil peroxidase (EPO), lactoperoxidase (LPO), chloroperoxidase (CPO) and derivatives thereof capable of selective binding to target microbes.

48 Claims, 9 Drawing Sheets-

OTHER PUBLICATIONS

Allen, R.C., "Reduced, radical, and exicted state oxygen in leukocyte microbicidal activity", In J.T. Dingle, P.J. Jacques and I.H. Shaw [eds.]. Lysosomes in Applied Biology and Therapeutics, North–Holland Publishing Company, 1979, pp. 197–233.

Allen, R.C., "Chemiluminescence: An Approach to the Study of the Humoral–phagocyte Axis in Host Defense Against Infection", In Liquid Scintillation Counting, Recent Applications and Development, vol. II. Sample Preparation and Applications, Academic Press, Inc., 1980, pp. 377–393.

Allen, R.C., et al., "Role of Myeloperoxidase and Bacterial Metabolism in Chemiluminescence of Granulocytes from Patients with Chronic Granulomatous Disease", *Journal of Infectious Diseases*, 144(4), 344–348, 1981.

Allen, R.C. et al., "Humoral–Phagocyte Axis of Immune Defense in Burn Patients", *Archives of Surgery*, 117, 133–140, 1982.

Allen, R.C., "Direct Quantification of Phagocyte Activity in Whole Blood: A Chemiluminigenic Probe Approach", In E. Kaiser, F. Gabl, M.M. Muller and P.M. Bayer [eds.] Proceedings of XI International Congress of Clinical Chemistry, Vienna, 1981. Walter de Gruyter, Berlin, New York, 1982, pp. 1043–1058.

Allen, R.C., "Biochemiexcitation: Chemiluminescence and the Study of Biological Oxygenation Reactions", In W. Adam and G. Cilento [eds.] Chemical and Biological Generation of Excited States, Academic Press, Inc., New York, 1982, pp. 309–344.

Allen, R.C., "Chemiluminescence and the Study of Phagocyte Redox Metabolism", In F. Rossi and P. Patrisica [eds.] Biochemistry and Function of Phagocytes, Plenum Publishing Corporation, 1982, pp. 411–421.

Allen, R.C. and M.M. Lieberman, "Kinetic Analysis of Microbe Opsonification Based on Stimulated Polymorphonuclear Leukocyte Oxygenation Activity", *Infection and Immunity*, 45(2), 475–482, 1984.

Allen, R.C., "Phagocytic Leukocyte Oxygenation Activities and Chemiluminescence: A Kinetic Approach to Analysis", In Marlene A. DeLuca and William D. McElroy [eds.] Methods in Enzymology, vol. 133, Bioluminescence and Chemiluminescence, Academic Press, Inc., 1986, pp. 449–493.

Allen, R.C., "Oxygen–Dependent Microbe Killing by Phagocyte Leukocytes: Spin Conservation and Reaction Rate", In W. Ando and Y. Moro–oka [eds.] The Role of Oxygen in Chemistry and Biochemistry, Proceedings of an International Symposium on Activation of Dioxygen and Homogeneous Catalytic Oxidations, Tsukuba, Japan, Jul. 12–16, 1987, *Studies in Organic Chemistry*, vol. 33, pp. 425–434, 1988 Elsevier Science Publishers B.V., Amsterdam.

Steinbeck, M.J. and J.A. Roth, "Neutrophil Activation by Recombinant Cytokines", *Reviews of Infectious Diseases*, 11(4), 549–568, 1989.

Malech, H.L. and J.I. Gallin, "Medical Intelligence, Neutrophils in Human Diseases", *New England Journal of Medicine*, 317(11), 687–694, 1987.

Olsson, I. and P. Venge, "The Role of the Human Neutrophil in the Inflammatory Reaction", *Allergy*, 35, 1–13, 1980.

Chenoweth, D.E., "Complement Mediators of Inflammation", In Gordon D. Ross [ed.] Immunobiology of the Complement System, An Introduction for Research and Clinical Medicine, pp 63–86, Academic Press, 1986.

Fearon, D.T. and L.A. Collins, "Increased Expression of C3b Receptors on Polymorphonuclear Leukocytes Induced by Chemotactic Factors and By Purification Procedures", *J. Immunology* 130(1), 370–175, 1983.

Fearon, D.T. and W.W. Wong, "Complement Ligand–Receptor Interactions that Mediate Biological Responses", *Ann. Rev. Immunol.* 1, 243–271, 1983.

Kearns, D.R. and A.U. Khan, "Sensitized Photooxygenation Reactions and the Role of Singlet Oxygen", *Photochemistry and Photobiology*, 10, 193–210, 1969.

Kanofsky, J.R., "Singlet Oxygen Production by Lactoperoxidase", *Journal of Biological Chemistry*, 258(10), 5991–5993, 1983.

Lehrer, R.I., "Antifungal Effects of Peroxidase Systems", *J. Bacteriol.* 99(2), 361–365, 1969.

Klebanoff, S.J. et al., "The Peroxidase–Thiocyanate–Hydrogen Peroxide Antimicrobial System", *Biochimica et Biophysica Acta*, 117, 63–72, 1966.

Klebanoff, S.J., "Myeloperoxidase–Halide–Hydrogen Peroxide Antibacterial System", *J. Bacteriol.* 95(6), 2131–2138, 1968.

Klebanoff, S.J., "Myeloperoxidase–mediated Antimicrobial Systems and their Role in Leukocyte Function", reprinted from*Biochemistry of the Phagocytic Process*, Julius Schultz ed., (North–Holland Publishing Company, 1970), reprinted.

Klebanoff, S.J. et al., "Toxic Effect of the Peroxidase–Hydrogen Peroxide–Halide Antimicrobial System on *Mycobacterium leprae*", *Infect. and Immun.* 44(2), 534–536, 1984.

Hamon, C.B. et al., "A Peroxidase–mediated, Streptococcus mitis–dependent antimicrobial system in saliva", *J. Exp. Med.* 137, 438–450, 1973.

Belding, M.E. et al., "Peroxidase–Mediated Virucidal Systems", *Science* 167, 195–196, 1970.

Steele, W.F. et al., "Antistreptococcal Activity of Lactoperoxidase", *J. Bacteriol.* 97(2), 635–639, 1969.

Mickelson, M.N., "Effect of Lactoperoxidase and Thiocyanate on the Growth of *Streptococcus pyogenes* and *Streptococcus agalactiae* in a Chemically Defined Culture Medium", *J. gen. Microbiol.* 43, 31–43, 1966.

* cited by examiner

METHOD FOR INHIBITING PATHOGENIC MICROBES IN AN ANIMAL USING A HALOPEROXIDASE-HALIDE-PEROXIDE SYSTEM

This is a continuation of application Ser. No. 08/137,817, filed Oct. 19, 1993, now abandoned, which is a continuation of Ser. No. 07/660,994 filed Feb. 21, 1991, abandoned.

FIELD OF THE INVENTION

The present invention relates to methods and compositions for the treatment of infection and control of flora composition. More particularly, the present invention relates to antiseptic methods and compositions using haloperoxidase microbicidal activity.

BACKGROUND OF THE INVENTION

Historical Background

The use of oxidizing antiseptics and disinfectants has an interesting development dating back to the late eighteenth century. Because of the relevance of hypohalite and peroxide antiseptics to the present invention, their abbreviated histories are presented. In 1788, the French chemist Berthollet described the disinfecting and bleaching properties of a solution prepared from aqueous alkali and chlorine, and in 1792 a potassium-based preparation of similar composition, eau de Javel, was sold commercially as a disinfectant. In 1820 Labarraque prepared a solution from aqueous sodium carbonate and chlorine. This liqueur de Labarraque was well known for its disinfectant and deodorizer qualities. In 1846 Semmelweis used chloride of lime, a calcium hypochlorite solution, to successfully control the spread of puerperal sepsis, and in 1881 Koch reported his results on the bactericidal action of hypochlorite.

In 1818 Thenard synthesized hydrogen peroxide ($H_2O_2$) by reacting dilute acid with barium dioxide to yield a 3 to 4% solution of $H_2O_2$ that was relatively unstable. The disinfectant properties of $H_2O_2$ were recognized by the mid nineteenth century. "Its application has been advocated for rendering water and milk safe, for disinfection of sewage; it has been applied in medicine, surgery, dentistry, hairdressing etc" (Heinemann, 1913, *J.A.M.A.* 60: 1603–1606). However, its antiseptic capacity is relatively poor in comparison with hypochlorites.

The antiseptic action of dyes was also known and used prior to and during the First World War. In 1900 Raab reported that the dye acridine killed living cells (i.e., paramecia) only in the presence of light (*Z. Biol.* 39: 524 et seq.), and in 1905 Jodlbauer and von Tappeiner demonstrated that $O_2$ was required for the dye-sensitized photokilling of bacteria (*Deut.Arch.Klin.Med.* 82: 520–546). Dye-sensitized, $O_2$-dependent photooxidation and photooxygenation reactivity is commonly referred to as photodynamic activity (Blum, 1941, *Photodynamic Action and Diseases Caused by Light,* Reinhold, New York). Dyes, such as flavine and brilliant green, were effective as antiseptic agents even when employed at relatively high dilutions in serous medium. Unfortunately, in addition to their potent antimicrobial action, these dyes also produce host damage, i.e., leukocyte killing (Fleming, 1919, *Brit.J.Surg.* 7: 99–129).

Research in the area of antiseptic action was accelerated by the First World War. During this period the previously described potency of hypochlorite-based antiseptics (Andrewes and Orton, 1904, *Zentrabl.Bakteriol.(Orig.A)* 35: 811–816) was firmly established, and preparations, such as Eusol (Smith et al., 1915, *Brit.Med.J.* 2: 129–136) and Dakin's solution (Dakin, 1915, *Brit.Med.J.* 2: 318–320) supplanted the initially favored carbolic acid and iodine antiseptics.

Alexander Fleming's 1919 Hunterian lecture (supra), entitled, "The Action of Chemical and Physiological Antiseptics in a Septic Wound" provides an excellent exposition of the subject of antisepsis that is relevant to this day. Fleming described two schools of thought regarding the treatment of wounds: (1) the physiological school which directed "their efforts to aiding the natural protective agencies of the body against infection", and (2) the antiseptic school which directed their efforts to killing the wound microbes with chemical agents.

The physiologic school maintained that the greatest protection against infection was obtained by aiding the physiological agencies: (1) blood and humoral defense mechanisms, and (2) phagocytic leukocytes. It was known that leukocytes collected in the walls and emigrate into the cavity of the wound, ultimately forming the cellular elements of pus. Fleming noted that the phagocytic leukocytes of "fresh pus" exert potent antimicrobial effect, but that "stale pus" (i.e., pus from an unopened furuncle), as well as heat-treated or antiseptic-treated "fresh pus", lack microbe killing capacity.

The Nonspecific Nature of Antiseptic Treatment

The basic problem of the chemical approach to antisepsis is that chemical antiseptics react non-specifically. "Disinfection is a chemical reaction in which the reactive agent acts not only on bacteria but upon the media in which they are found" (Dakin, 1915, *Brit.Med.J.* 2: 809–810). Antiseptic solutions produce maximum microbe killing when the organisms are suspended in an aqueous medium, but germicidal action is greatly decreased by competitive reaction with the organic matter present in serous fluid or blood.

Antiseptics can non-specifically react with and inhibit normal immunophysiologic defense mechanisms. Germicidal concentrations of antiseptics inhibit the antimicrobial function of phagocytic leukocytes. "The leukocytes are more sensitive to the action of chemical antiseptics than are the bacteria, and, in view of this, it is unlikely that any of these antiseptics have the power of penetrating into the tissues and destroying the bacteria without first killing the tissues themselves. The natural antiseptic powers of the pus are done away with, but the microbes are not completely destroyed, and those which are left are allowed to grow unhindered until such time as fresh pus-cells can emigrate to keep them in check. A consideration of the leucocidal property of antiseptics will show us that certain antiseptics are suitable for washing of a wound, while others are bad. If we desire, therefore, an antiseptic solution with which to wash out a wound, we should choose one which loses its antileucocytic power rapidly and which exercises its antiseptic action very quickly. We then have the washing effect of the fluid without doing much damage to the wound. One great advantage of eusol and Dakin's solution is that they disappear as active chemical agents in a few minutes and do not have any lasting deleterious effect on the leukocytes" (Fleming, 1919).

Mechanism of Action

Many of the early workers believed that hypochlorite microbicidal action was dependent on the nascent oxygen liberated as a product of hypochlorous acid autoprotolysis, and that the liberated oxygen combined with the unsaturated components in the cell protoplasm to effect killing. This view was challenged early in this century by Dakin. "It has been repeatedly stated that the antiseptic action of hypochlorous acid was due to the liberation of oxygen. I have been unable to find any evidence to support this statement." He went on to propose a more direct chlorination mechanism. "It appears that when hypochlorous acid and hypochlorites act upon organic matter of bacterial or other origin some of the (NH) groups of the proteins are converted into (NCl) groups. The products thus formed—belonging to the group of chloramines—I have found to possess approximately the same antiseptic action as the original hypochlorite, and it appears more probable that the antiseptic action of the hypochlorites is conditioned by the formation of these chloramines rather than by any decomposition with liberation of oxygen" (Dakin, 1915). Furthermore, it was known that "oxygen from sources other than chlorine does not kill bacteria as readily as does the amount of chlorine theoretically necessary to yield an equivalent amount of nascent oxygen" (Mercer and Somers, 1957, Adv.Food Res. 7: 129–160).

Dakin's position on the direct microbicidal action of chlorine, which persists to the present, is also problematic. "Experimental proof is lacking also for other hypotheses advanced to explain the bactericidal action of chlorine. These include suggestions that bacterial proteins are precipitated by chlorine; that cell membranes are altered by chlorine to allow diffusion of cell contents; and that cell membranes are mechanically disrupted by chlorine" (Mercer and Somers, 1957). Chlorine-binding to bacteria is remarkably low at pH 6.5 and is doubled by raising the pH to 8.2 (Friberg, 1956, Acta Pathol.Microbiol.Scand. 38: 135–144). On the other hand, the bactericidal and virucidal capacity of hypochlorite is increased by acidity, i.e., by lowering the pH (Butterfield et al., 1943, Publ.Health Reports 58: 1837–1866; Friberg and Hammarstrom, 1956, Acta Pathol. Microbiol.Scand. 38: 127–134). As such, chlorine-binding is inversely related to chlorine-dependent killing.

Organic chloramine preparations, e.g. chloramine-T, also serve as antiseptic agents, but paradoxically, the microbicidal action of these chloramines is concluded to result in whole or in large part from the hypochlorous acid formed from chloramine hydrolysis (Leech, 1923, J.Am.Pharm. Assoc. 12: 592–602). Chloramine bactericidal action "may be due in whole or in part to the hypochlorous acid formed in accordance with the hydrolysis and ionization equilibria" (Marks et al., 1945, J.Bacteriol. 49: 299–305). The greater stability afforded by the slower hydrolysis of chloramines slows germicidal action.

Hypochlorite exerts a bactericidal action at concentrations of 0.2 to 2.0 ppm, (i.e., 4 to 40 nmol per ml). The high potency of such a "trace" concentration strongly suggest that microbicidal action results from the inhibition of an essential enzyme or enzymes (Green, 1941, Adv.Enzymol. 1: 177–198). Evidence has been presented that hypochlorous acid inhibits various sulfhydryl enzymes and that inhibition of glucose metabolism is proportional to bacterial killing (Knox et al., 1948, J.Bacteriol. 55: 451–458).

The literature with regard to the mechanism of $H_2O_2$ action is somewhat incomplete. However, the overall consensus is that "$H_2O_2$ in spite of its high oxidation-reduction potential is as sluggish an oxidizing agent as molecular oxygen and in fact a large number of oxidations attributed to this substance have been found, on careful examination, to be due to free radical formation which occurs on addition of catalytic amounts of $Fe^{++}$ or $Cu^{++}$" (Guzman-Barron et al., 1952, Arch.Biochem.Biophys. 41: 188–202). This view expresses the consensus conclusion of several studies (Yoshpe-Purer and Eylan, 1968, Health Lab.Sci. 5: 233–238; Miller, 1969, J.Bacteriol. 98: 949–955).

Various dyes have also been used as antiseptics. Photodynamic action results when a dye ($^1$Dye), i.e., a singlet multiplicity sensitizer molecule, absorbs a photon and is promoted to its singlet excited state ($^1$Dye*). If $^1$dye* decays back to its $^1$Dye ground state by photon emission, the phenomenon of fluorescence is observed without photodynamic action. In order to serve as a photodynamic sensitizer the $^1$Dye* must undergo intersystem crossing (ISC), i.e., change in spin multiplicity, to yield the metastable triplet excited state of the dye ($^3$Dye*) in relatively high quantum yield (Gollnick, 1968, Advan.Photochem. 6: 1–122):

$$^1Dye \text{ - - - } h\nu \rightarrow {}^1Dye^* \text{ - - - } ISC \rightarrow {}^3Dye^* \qquad (1)$$
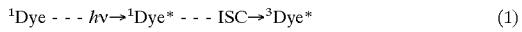

Sensitizers absorb light ranging from the near ultraviolet throughout the visible to include the near infrared. This absorption is responsible for the color properties of the "$^1$dye". The wavelength of light (i.e., the energy of the photon) required for dye excitation is defined by the absorption spectrum of the dye.

The $^3$Dye* state is relatively long-lived and as such, can react with other molecules. Photodynamic reactions can be divided into two main classes depending on the reactivity of $^3$Dye* (Schenck and Koch, 1960, Z.Electrochem. 64: 170–177). In Type I reactions the excited triplet sensitizer undergoes direct redox transfer with another molecule. Sensitizers for Type I reactions typically are readily oxidized or reduced.

$$^3Dye^* + {}^1SubH \rightarrow {}^2Dye + {}^2Sub. \qquad (2)$$

In equation (2), the triplet sensitizer serves as a univalent oxidant and is reduced to its doublet state ($^2$Dye), and the singlet multiplicity substrate (1SubH) is oxidized to a doublet multiplicity, free radical $^2$Sub. state. In a analogous fashion, a reducing $^3$Dye* may serve as a radical reductant. The $^2$Dye product of reaction (2) can react with ground state $O_2$, a triplet multiplicity diradical molecule ($^3O_2$), to yield the doublet multiplicity hydrodioxylic acid radical ($^2.O_2H$) or its conjugate base the superoxide anion ($^2.O_2^-$) and regenerate the singlet ground state of the dye:

$$^2Dye + {}^3O_2 \rightarrow {}^1Dye + {}^2.O_2H(\text{or } {}^2.O_2^-) \qquad (3)$$
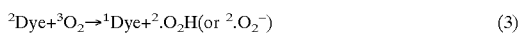

Under neutral to acid conditions these products of oxygen reduction undergo doublet-doublet (i.e., radical-radical) annihilation to yield $H_2O_2$:

$$^2.O_2H + {}^2.O_2^- + H^+ \rightarrow {}^1H_2O_2 + {}^1O_2 \qquad (4)$$

If the reaction is by direct annihilation spin conservation will be maintained, and as such, singlet molecular oxygen ($^1O_2$) can also be produced (Khan, 1970, Science 168: 476–477).

In Type II reactions the excited triplet sensitizer interacts directly with triplet (ground state) $^3O_2$. Reaction involves the spin-balanced transfer of excitation energy from $^3$Dye* to $^3O_2$ yielding the ground state $^1$Dye and singlet molecular oxygen ($^1O_2$) as products (Kautsky, 1939, Trans.Faraday Soc. 35: 216–219):

$$^3Dye^* + {}^3O_2 \text{ - - - } {}^1DyeO_2 \rightarrow {}^1Dye + {}^1O_2 \qquad (5)$$
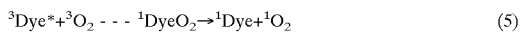

Reaction (5) is very fast and is the most common Type II pathway. However, if $^3$Dye* is sufficiently reducing, direct univalent electron transfer to $O_2$ may occur:

$$3Dye^* + {}^3O_2 \text{ - - - } {}^1DyeO_2 \rightarrow {}^2Dye^+ + {}^2.O_2 \qquad (6)$$
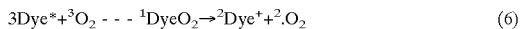

Radical annihilation can proceed to yield $H_2O_2$ as described by reaction (4). In considering these reaction pathways it should be appreciated that reaction (5) is favored over reaction (6) by over two orders of magnitude (Kasche and Lindqvist, 1965, *Photochem. Photobiol.* 4: 923–933).

Microbial killing by dyes could result from the reaction of the $^3$Dye* itself or its Type I and Type II reaction products, i.e., $^2.O_2^-$, $H_2O_2$, and especially $^1O_2$, with microbial proteins, nucleic acids, unsaturated lipids, et cetera (Spikes and Livingston, 1969, *Adv.Rad.Biol.* 3: 29–121).

$^1O_2$, a broad spectrum electrophilic oxygenating agent, can inhibit enzymes by destroying amino acids essential to catalytic activity. The rate constants ($k_r$, in $M^{-1}sec^{-1}$) for the reaction of $^1O_2$ with tryptophan, histidine, and methionine range from $2*10^7$ to $9*10^7$ (Matheson and Lee, 1979, *Photochem.Photobiol.* 29: 879–881; Kraljic and Sharpatyi, 1978, *Photochem.Photobiol.* 28: 583–586). If generated in close proximity to a target microbe, a "trace" quantity of $^1O_2$ could effectively inhibit enzymes required for microbe metabolism. Unsaturated lipids, nucleic acids and other electron dense biological molecules are also reactive with $^1O_2$. The dioxygenation of such essential cellular components might also play a part in microbicidal action.

The Continuing Problem:

The following essential points can be distilled from the preceding material. First, high potency chemical antiseptics are typically oxidizing agents, e.g., HOCl. These oxidizing and oxygenating agents are capable of microbicidal action in "trace" quantities, and probably exert their effects via inhibition of enzymes essential for metabolism (Green, 1941).

Second, the antimicrobial potency of such antiseptics is compromised by their nonspecific reactivity. Damage is not limited to the target microbe. As pointed out by Fleming, host cells are generally more susceptible than microbes to toxic action of antiseptics.

An ideal antiseptic agent would exert potent reactivity against a broad range of pathogenic microbes including fungi with minimum toxicity to host cells. In keeping with the principles of the physiological school of wound care, an antiseptic should aid or augment the natural protective agencies of the body against infection.

To a limited extent, these requirements are met by certain antibiotics. The selective bactericidal action of antibiotics is based on differences between prokaryotic and eukaryotic cells with regard to protein synthesis, nucleic acid replication, and the presence or composition of the cell wall. Antibiotics can, in effect, selectively poison certain bacteria, i.e., prokaryotic organisms, without poisoning the eukaryotic host cells. However, the broad spectrum action of antibiotics can have detrimental effects on the bacteria that make up the normal flora of the host. The bacteria of the normal flora serve as a barrier to the growth of pathogenic organisms, and as such, antibiotic destruction of the normal flora provides an opportunity for the growth of more pathogenic bacteria. Antibiotic-associated pseudomembranous colitis results from the overgrowth of pathogens, i.e., *Clostridium difficile* and rarely *Staphylococcus aureus*, following antibiotic destruction of normal flora.

In addition, yeast and fungi are eukaryotic microbes, and as such, are essentially unaffected by antibiotics. Consequently, yeast overgrowth and infections can follow antibiotic treatment of bacterial infections.

Antibiotics can also exert direct toxic effects. These detrimental effects can result from the direct action of the drug on host cells and tissue, e.g., the nephrotoxicity of antibiotics.

As is readily apparent from the foregoing, there is a long felt need for new and improved antiseptics which have reactivity against a broad range of pathogenic microbes, but exhibit a minimum of activity toward host cells and normal flora.

SUMMARY OF THE INVENTION

It has now been discovered that haloperoxidases may be used to selectively bind to and, in the presence of peroxide and halide, inhibit the growth of target microbes without eliminating desirable microbes or significantly damaging other components of the medium, such as host cells, in the target microbe's environment. Due to the newly discovered selective binding properties of haloperoxidases, when a target microbe, such as a pathogenic microbe, has a binding capacity for haloperoxidase greater than that of a desired microbe, such as members of the normal flora, the target microbe selectively binds the haloperoxidase with little or no binding of the haloperoxidase by the desired microbe. In the presence of peroxide and halide, the target bound haloperoxidase catalyzes halide oxidation and facilitates the disproportionation of peroxide to singlet molecular oxygen at the surface of the target microbe, resulting in selective killing of the target microbe with a minimum of collateral damage to the desired microbe or physiological medium.

The selective nature of haloperoxidase binding makes the methods and compositions of the invention highly useful in the therapeutic or prophylactic antiseptic treatment of human or animal subjects, since their use can be designed to be highly effective in combatting bacterial or fungal infections without significant damage to normal flora or host cells.

Suitable haloperoxidases for use in the methods and compositions of the invention include myeloperoxidase (MPO), eosinophil peroxidase (EPO), lactoperoxidase (LPO) and chloroperoxidase (CPO).

BRIEF DESCRIPTION OF THE DRAWINGS

FIG. 7 shows plots of binding data for MPO as described in detail in Example 6.

FIG. 8 shows plots of binding data for CPO as described in detail in Example 7.

FIG. 9 shows plots of binding data for EPO as described in detail in Example 8.

FIG. 10 shows plots of binding data for LPO as described in detail in Example 8.

DETAILED DESCRIPTION OF THE INVENTION

Figure 1:
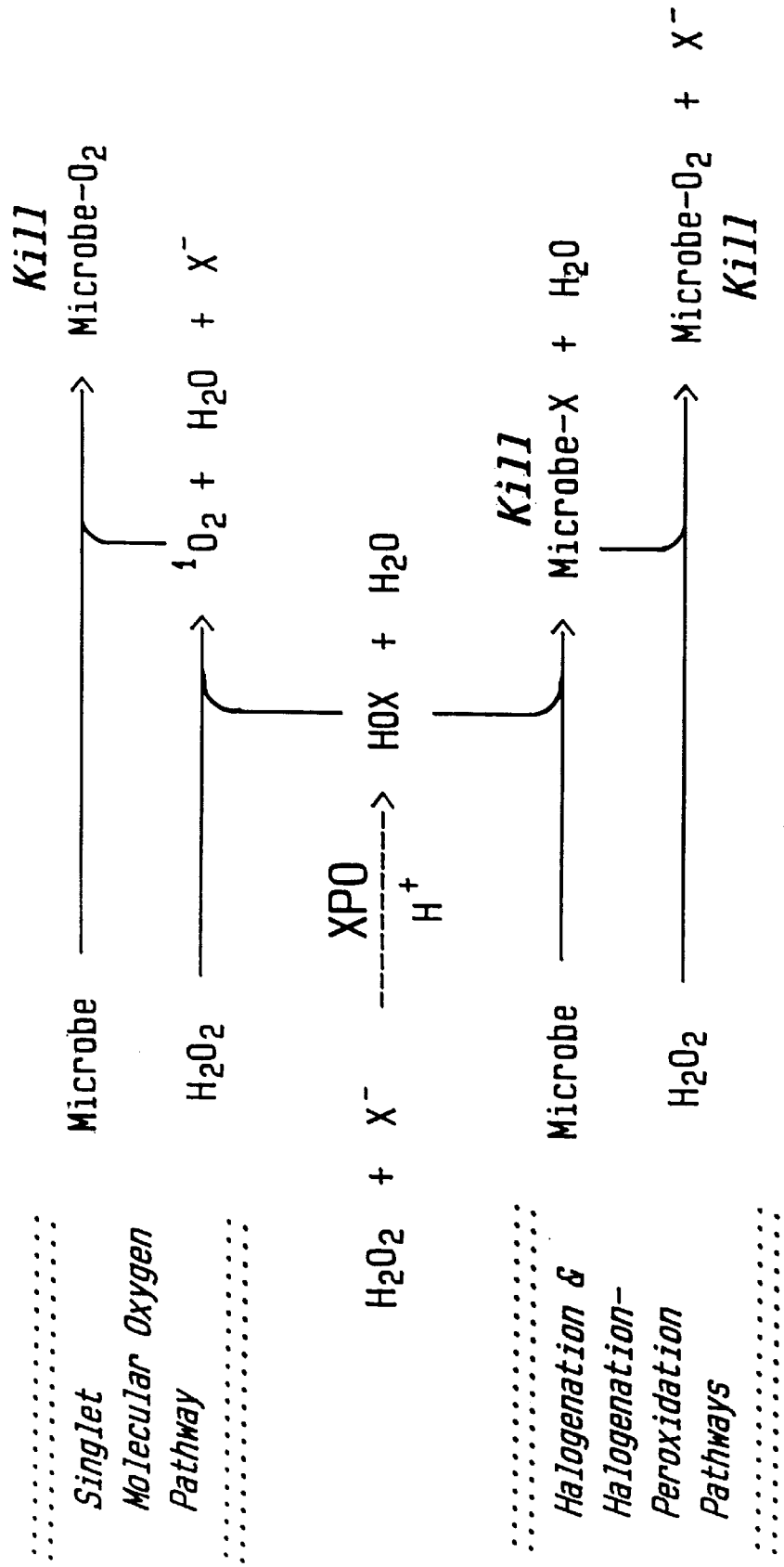
FIG. 1 is a schematic representation of microbial killing via the single-molecular oxygen ($^1O_2$) pathway and the halogenation-peroxidation (virtual singlet molecular oxygen) pathway of the invention.

The present invention is broadly directed to methods and compositions using haloperoxidases to selectively bind to and kill target microbes, without eliminating desirable microbes or significantly damaging components of the medium, such as host cells in the target microbe's environment.

In one particularly preferred embodiment, the methods and compositions are used as antiseptic agents. In addition to potent reactivity against a broad range of pathogenic microbes including fungi, and minimum toxicity to host cells, an ideal antiseptic agent should also selectively preserve the normal flora of the host organism. In one aspect, the present invention provides antiseptic systems based on the use of dioxygenating enzyme systems with selective affinity for pathogenic microbes. The antiseptic systems of the invention have the potency of chemical antiseptics without the associated host tissue destruction or disruption of normal flora; i.e., the antiseptic action is selective and confined to the target microbe. The invention satisfies the above stated criteria for an ideal antiseptic system.

Generation of Oxidizing and Oxygenating Agents:

Haloperoxidases (XPOs) such as myeloperoxidase (MPO) and eosinophil peroxidase (EPO), are known to exhibit microbe killing activity in natural systems when presented with an appropriate halide cofactor ($X^-$) and $H_2O_2$ as substrate (Klebanoff, 1968, *J.Bacteriol.* 95: 2131–2138). However, the selective nature of haloperoxidase binding and the utility of these systems for therapeutic, research and industrial applications has not heretofor been recognized.

Initial Reaction

The initial step of the XPO-catalyzed reaction involves the oxidation of $X^-$ by $H_2O_2$:

$$H_2O_2 + X^- + H^+ \text{ - - - (XPO)} \rightarrow HOX + H_2O \quad (7)$$

This reaction is best appreciated in terms of the Nernstian relationship:

$$E = E_O + \frac{RT}{nF} \ln \frac{[\text{Oxidized}]}{[\text{Reduced}]} + \frac{RT}{nF} \ln [H^+] \quad (8)$$

where E is the observed potential in volts, $E_o$ is the standard potential in volts, R is the gas constant, T is the absolute temperature, n is the number of electrons per gram-equivalent transferred, F is a faraday, ln is the natural log of the ratio of the concentrations of reduced to oxidized reactants ([oxidized]/[reduced]), and ln [$H^+$] is the natural log of the proton (hydrogen ion) concentration. The reaction described by equation (7) can be considered as two separate half reactions: the reduction of $H_2O_2$ to $H_2O$, $$E_{H_2O_2} = E_O + \frac{RT}{nF} \ln \frac{[H_2O_2]}{[H_2O]} + \frac{RT}{nF} \ln [H^+] \quad (9)$$

and the oxidation of $X^-$ to HOX, $$E_{X^-} = E_O + \frac{RT}{nF} \ln \frac{[HOX]}{[X^-]} + \frac{RT}{nF} \ln [H^+] \quad (10)$$

The combined reaction for the oxidation of $X^-$ by $H_2O_2$ is driven by the net potential $\Delta E$, i.e., $$\Delta E = E_{H_2O_2} - E_{X^-} = \frac{RT}{nF} \ln \frac{[H_2O][HOX]}{[X^-][H^+][H_2O_2]} \quad (11)$$

Thermodynamically, the net change in potential can be described as the change in free energy ($\Delta G$) for the reaction:

$$\Delta G = RT \ln \frac{[H_2O][HOX]}{[X^-][H^+][H_2O_2]} \quad (12)$$

Change in free energy is related to the change in potential by the equation, $$\Delta G = -nF\Delta E \quad (13)$$

An enzyme can greatly increase the rate of a specific chemical reaction, but it does not affect the $\Delta G$ of the reaction. Enzymes provide a mechanistic pathway for thermodynamically allowed reactions. In the present invention haloperoxidases provide the mechanism for utilizing $H_2O_2$ to generate more reactive oxidants, i.e., hypohalites (HOX), and oxygenating agents, i.e., singlet molecular oxygen ($^1O_2$). The data of Table 1 illustrate that $H_2O_2$ oxidation of halides yielding hypohalites are thermodynamically favored, i.e., exergonic. Note that exergonicity is inversely related to electronegativity of the halogen.

TABLE 1

Primary Reaction
$H_2O_2 + X^- + H^+ \xrightarrow{(XPO)} H_2O_2 + HOX + \Delta G_1$

| pH | $E_{H_2O_2}$ volts | − | $E_{Cl^-}$ volts | = | $\Delta E_1$ volts | kcal mol$^{-1}$ ($\Delta G_1$) |
|---|---|---|---|---|---|---|
| 4 | 1.5396 | − | 1.3760 | = | 0.1636 | (−7.53) |
| 5 | 1.4805 | − | 1.3465 | = | 0.1340 | (−6.16) |
| 6 | 1.4214 | − | 1.3170 | = | 0.1044 | (−4.80) |
| 7 | 1.3623 | − | 1.2875 | = | 0.0748 | (−3.44) |
| 8 | 1.3032 | − | 1.2580 | = | 0.0452 | (−2.08) |

| pH | $E_{H_2O_2}$ | − | $E_{Br^-}$ | = | $\Delta E_1$ | ($\Delta G_1$) |
|---|---|---|---|---|---|---|
| 4 | 1.5396 | − | 1.2130 | = | 0.3266 | (−15.02) |
| 5 | 1.4805 | − | 1.1835 | = | 0.2970 | (−13.66) |
| 6 | 1.4214 | − | 1.1540 | = | 0.2674 | (−12.30) |
| 7 | 1.3623 | − | 1.1245 | = | 0.2378 | (−10.94) |
| 8 | 1.3032 | − | 1.0950 | = | 0.2082 | (−9.58) |

| pH | $E_{H_2O_2}$ | − | $E_{I^-}$ | = | $\Delta E_1$ | ($\Delta G_1$) |
|---|---|---|---|---|---|---|
| 4 | 1.5396 | − | 0.8690 | = | 0.6706 | (−30.85) |
| 5 | 1.4805 | − | 0.8395 | = | 0.6410 | (−29.49) |
| 6 | 1.4214 | − | 0.8100 | = | 0.6114 | (−28.12) |
| 7 | 1.3623 | − | 0.7805 | = | 0.5818 | (−26.76) |
| 8 | 1.3032 | − | 0.7510 | = | 0.5522 | (−25.40) |

Value calculated from the data of Pourbaix, 1966, *Atlas of Electrochemical Equilibria in Aqueous Solutions*, Pergamon Press, p. 644.

Secondary Reaction

Reaction of HOX with $H_2O_2$, both singlet multiplicity reactants, will proceed via a singlet multiplicity surface to yield $^1O_2$, $X^-$, and $H_2O$, all singlet multiplicity products (Kasha and Khan, 1970, *Ann.N.Y.Acad.Sci.* 171: 5–23); i.e., $$HOX + H_2O_2 \rightarrow X^- + H^+ + {}^1O_2 + H_2O \quad (14)$$

The net potential of this reaction is given by the relationship:

$$\Delta E = E_{HOX} - E_{H_2O_2} = \frac{RT}{nF} \ln \frac{[H_2O][X^-][H^+][]}{[HOX][H_2O_2]} \quad (15)$$

Tables 2 illustrates that the HOCl or HOBr oxidation of $H_2O_2$ has more than sufficient exergonicity for the generation of $^1O_2$. When the HOX is HOI, the reaction is sufficiently exergonic only in the near-neutral to alkaline pH range.

TABLE 2

Secondary Reaction
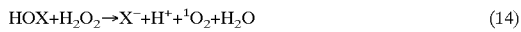

| pH | $E_{HOCl}$ volts | − | $E_{H_2O_2}$ volts | = | $\Delta E_2$ volts | ($\Delta G_2$) kcal mol$^{-1}$ | ($\Delta G_a$) |
|---|---|---|---|---|---|---|---|
| 4 | 1.3760 | − | 0.4456 | = | 0.9304 | (−42.80) | (−20.27) |
| 5 | 1.3465 | − | 0.3865 | = | 0.9600 | (−44.16) | (−21.63) |
| 6 | 1.3170 | − | 0.3274 | = | 0.9896 | (−45.52) | (−22.99) |
| 7 | 1.2875 | − | 0.2683 | = | 1.0192 | (−46.88) | (−24.35) |
| 8 | 1.2580 | − | 0.2092 | = | 1.0488 | (−48.25) | (−25.72) |

| pH | $E_{HOBr}$ | − | $E_{H_2O_2}$ | = | $\Delta E_2$ | ($\Delta G_2$) | ($\Delta G_a$) |
|---|---|---|---|---|---|---|---|
| 4 | 1.2130 | − | 0.4456 | = | 0.7674 | (−35.30) | (−12.77) |
| 5 | 1.1835 | − | 0.3865 | = | 0.7970 | (−36.66) | (−14.13) |
| 6 | 1.1540 | − | 0.3274 | = | 0.8266 | (−38.02) | (−15.49) |
| 7 | 1.1245 | − | 0.2683 | = | 0.8562 | (−39.39) | (−16.86) |

TABLE 2-continued

Secondary Reaction

| | | | | | | | |
|---|---|---|---|---|---|---|---|
| 8 | 1.0950 | − | 0.2092 | = | 0.8858 | (−40.75) | (−18.22) |

| pH | $E_{HOI}$ | − | $E_{H_2O_2}$ | = | $\Delta E_2$ | ($\Delta G_2$) | ($\Delta G_a$) |
|---|---|---|---|---|---|---|---|
| 4 | 0.8690 | − | 0.4456 | = | 0.4234 | (−19.48) | (3.05) |
| 5 | 0.8395 | − | 0.3865 | = | 0.4530 | (−20.84) | (1.69) |
| 6 | 0.8100 | − | 0.3274 | = | 0.4826 | (−22.20) | (0.33) |
| 7 | 0.7805 | − | 0.2683 | = | 0.5122 | (−23.56) | (−1.03) |
| 8 | 0.7510 | − | 0.2092 | = | 0.5418 | (−24.92) | (−2.39) |

The generation of $^1O_2$ in this secondary reaction is endergonic by 22.6 kcal mol$^{-1}$.
The value of $\Delta G_a$ reflects the adjusted exergonicity; i.e., $\Delta G_2 + 22.56 = \Delta G_a$.
Values calculated from the data of Pourbaix (1966).

The overall net reaction, i.e., the sum of reactions (7) and (14):

$$2H_2O_2 \cdots (XPO) \rightarrow 2H_2O + {}^1O_2 \quad (16)$$

is a $H_2O_2$ disproportionation yielding $^1O_2$ plus a $\Delta G$ of −27.8 kcal mol$^{-1}$ as illustrated by the data of Table 3.

TABLE 3

Net Reaction
$2H_2O_2 \rightarrow 2H_2O + {}^1O_2 + \Delta G_{na}$

| pH | $E_{H_2O_2}$ volts | − | $E_{H_2O}$ volts | = | $\Delta E_n$ volts | ($\Delta G_n$) kcal mol$^{-1}$ | ($\Delta G_{na}$) |
|---|---|---|---|---|---|---|---|
| 4 | 1.5396 | − | 0.4456 | = | 1.094 | (−50.32) | (−27.79) |
| 5 | 1.4805 | − | 0.3865 | = | 1.094 | (−50.32) | (−27.79) |
| 6 | 1.4214 | − | 0.3274 | = | 1.094 | (−50.32) | (−27.79) |
| 7 | 1.3623 | − | 0.2683 | = | 1.094 | (−50.32) | (−27.79) |
| 8 | 1.2580 | − | 0.2092 | = | 1.094 | (−50.32) | (−27.79) |

The generation of $^1O_2$ in this secondary reaction is endergonic by 22.6 kcal mol$^{-1}$.
The value of $\Delta G_{na}$ reflects the adjusted exergonicity; i.e., $\Delta G_n + 22.56 = \Delta G_{na}$.
Values calculated from the data of Pourbaix (1966).

XPO's catalyze $H_2O_2$ disproportionation by introducing redox asymmetry favoring reactive adjustment. $H_2O_2$ oxidation of $X^-$ is mildly exergonic yielding HOX. HOX oxidation of $H_2O_2$ is highly exergonic yielding $^1O_2$. Stated differently, both $H_2O_2$ oxidation of Cl$^-$ and HOCl oxidation of $H_2O_2$ are thermodynamically favored. When the XPO is myeloperoxidase (MPO), $X^-$ can be Cl$^-$, Br$^-$, and to a limited extent, I$^-$. When the XPO is eosinophil peroxidase (EPO) or lactoperoxidase, $X^-$ can be Br$^-$ and to a limited extent, I$^-$.

One aspect of the invention provides a method for selectively inhibiting the growth of a first, target microbe in a medium without eliminating a second, desired microbe from the medium by introducing into the medium, in the presence of peroxide and halide, an amount of the haloperoxidase effective to selectively bind to and inhibit the growth of the first microbe, but ineffective to eliminate the second microbe from the medium. The ability to selectively inhibit the growth of a target microbe in a medium results from the discovery that haloperaxidases of the invention, at controlled concentration levels, selectively bind to microbes to varying degrees and with differing affinities. When the target microbe has a binding capacity for a haloperoxidase greater than that of a desired microbe, as is described in detail infra, the provision of the haloperoxidase to the medium in less than saturating amounts results in the selective binding of the haloperoxidase to the surface of the target microbes with minimal or no binding of the haloperoxidase to the surface of the desired microbe. In the presence of peroxide and a halide, the target-bound haloperoxidase catalyzes halide oxidation and facilitates the disproportionation of peroxide to singlet molecular oxygen at the surface of the target microbe. Since the lifetime of singlet molecular oxygen is relatively short lived and its diffusion potential is proportionately limited, as is also described in detail infra, the production of singlet molecular oxygen at the surface of the target microbe results in selective killing of the target microbe with a minimum of collateral damage to the desired microbe or other physiological components of the medium.

In accordance with another aspect of the invention, it has been discovered that haloperoxidases of the invention can be employed as antiseptics in the therapeutic or prophylactic treatment of human or animal subjects to selectively bind to and kill pathogenic microbes with a minimum of collateral damage to host cells. Thus, the invention further provides a method of treating a human or animal host by administering to the host an amount of a haloperoxidase which is antiseptically effective in the presence of a peroxide and a halide, but is ineffective to significantly damage normal cells of the host. Preferably, the nature and amount of haloperoxidase employed is controlled so as to be ineffective to eliminate normal flora of the host.

Haloperoxidases useful in the present invention are defined as halide:hydrogen peroxide oxidoreductases (e.g., EC No. 1.11.1.7 and EC No. 1.11.1.10 under the International Union of Biochemistry) for which halide is the electron donor or reductant and peroxide Is the electron receiver or oxidant. Any haloperoxidase which catalyzes the halide dependent generation of singlet molecular oxygen from hydrogen peroxide may be used in the present invention. Suitable haloperoxidases, as demonstrated herein, include myeloperoxidase (MPO), eosinophil peroxidase (EPO), lactoperoxidase (LPO), chloroperoxidase (CPO), and derivatives thereof, with the presently preferred haloperoxidases being myeloperoxidase and eosinophil peroxidase. By "derivatives thereof" as used herein generally means chemically or functionally modified MPO, EPO, CPO, and LPO which are capable of specifically binding to target microbes or specific eukaryotic cell types and which retain haloperoxidase activity in the enhancement of the disproportionation of peroxide to form singlet molecular oxygen in the presence of a suitable halide, as described herein. Illustrative examples of useful derivatives include haloperoxidases which have been conjugated to antibodies, antibody fragments, lectins or other targeting moieties which are capable of specifically recognizing and selectively binding to antigens, receptor sites, or other distinguishing features on the surface of target microbes or target cells, such as cancer cells. Due to the relative nonspecificity of microbe binding of underivatized CPO and LPO, these haloperoxidases will be preferably employed in the practice of the invention after derivatization to enhance target microbe binding specificity and/or affinity.

Since the antiseptic activity of the haloperoxidase compositions of the invention involves the reaction of peroxide and halide to form hypohalite, and the reaction of peroxide and hypohalite to form singlet molecular oxygen, as described above, the activity of the compositions of the invention is dependent upon the presence, at the site of infection, of a suitable peroxide and halide. In some situations, peroxide (e.g., hydrogen peroxide) may be present at the site of infection due, for example, to the activity of naturally occurring flora, and sufficient amounts of chloride may be present in the physiological milieu to act as a cofactor in the conversion reaction. In these situations, no additional peroxide or halide need be administered to the subject to be treated. In other situations, it may be necessary to additionally provide hydrogen peroxide and/or halide at the site of infection. Accordingly, the compositions of the invention may additionally comprise, if desired, a peroxide or agent capable of producing peroxide in vivo and a halide.

Peroxides useful in the methods and compositions of the invention include hydrogen peroxide and alkyl hydroperoxides of the formula:

R—OOH wherein R is a hydrogen or a short chain alkyl group having from 1 to 3 carbon atoms. The oxidant activity generally decreases with increasing R chain length, as follows:

$R=H>>CH_3>CH_3CH_2>CH_3(CH_2)_2$

The presently preferred peroxide for use in the compositions of the invention is hydrogen peroxide. Hydrogen peroxide may also be made available at the site of the infection by including in the antiseptic composition an agent capable of producing hydrogen peroxide in vivo. Particularly useful agents for this purpose include, for example, oxidases, such as glucose oxidase and galactose oxidase.

When hydrogen peroxide is directly included in compositions of the invention, the amounts employed are preferably designed to provide maximal antiseptic activity while minimizing damage to the cells and tissue of the human or animal subject. Accordingly, when included in liquid compositions for topical or buccal administration, the compositions of the invention may comprise from about 1 nmol to about 10 μmol of hydrogen peroxide per ml of liquid composition, more preferably from about 5 nmol to about 5 μmol of hydrogen peroxide per ml of liquid composition, and most preferably from about 10 nmol to about 1 μmol of hydrogen peroxide per ml of liquid composition. Agents capable of producing hydrogen peroxide in vivo, e.g., oxidases, are particularly useful for dynamic control of the amounts of hydrogen peroxide present at the site of infection. Such agents maximize antiseptic activity of the composition while minimizing damage to tissue of the subject to be treated. Accordingly, the amount of such agents to be employed will be highly dependent on the nature of the agent and the therapeutic effect desired, but will preferably be capable of producing a steady state level of from about 1 pmol to about 100 nmol of hydrogen peroxide per ml of liquid per minute, depending on the type and concentration of halide available at the site of microbe infection.

Suitable halides for use in the methods and compositions of the invention may be bromide or chloride. The use, selection, and amount of halide employed in a particular application will depend upon various factors, such as the haloperoxidase used in the antiseptic composition, the desired therapeutic effect, the availability of peroxide and other factors. When the haloperoxidase is MPO or CPO, the halide may be bromide or chloride. Since chloride is present in most physiological media at levels sufficient to be non-limiting as the halide cofactor, an external source of chloride is generally not required and thus the presently most preferable halide for use in chloride. When an external source of chloride is desired, the amount of chloride employed will preferably fall in the range of about 10 μmol chloride to about 150 μmol chloride per ml of solution to approximate physiological conditions. When the haloperoxidase is EPO or LPO, chloride is relatively ineffective as a cofactor, and accordingly, the preferred halide is bromide. When included in liquid compositions for topical or buccal administration, the compositions of the invention may comprise from about 1 nmol bromide to about 20 $\mu$mol bromide per ml of liquid composition, more preferably from about 10 nmol bromide to about 10 $\mu$mol bromide per ml of liquid composition, and most preferably from about 100 nmol bromide to about 1 pmol bromide per ml of liquid composition. Liquid compositions for systemic delivery and other dosage forms of the compositions of the invention will preferably provide substantially equivalent amounts of halide at the site of the microbe infection to be treated.

As is described in detail in Example 10, infra, the ratio of halide to peroxide is an important consideration in formulating an effective microbicidal environment. Accordingly, in addition to ensuring effective levels of halide and peroxide at the situs of microbial attack, as described above, it is preferable to practice the methods of the invention at halide-:peroxide ratios that provide optimal microbicidal activity. For example, when the haloperoxidase is MPO and the halide is $Cl^-$, the ratio of $Cl^-$ to peroxide is preferably maintained in the range of about 1 to about 40,000 in the environment of microbicidal activity, more preferably from about 50 to about 40,000 and most preferably from about 200 to about 40,000. When the halide is $Br^-$, the ratio of $Br^-$ to peroxide is preferably maintained in the range of about 0.1 to about 4,000 in the environment of microbicidal activity, more preferably from about 0.5 to about 2,000 and most preferably from about 1 to about 1,000.

When used in antiseptic applications, the methods and compositions of the invention can be used to treat a broad spectrum of infections by pathogenic microbes, preferably with a minimum of damage to normal flora. As used herein, "pathogenic microbes" is intended to include pathogenic bacteria or fungi which do not normally reside in the host or which have over populated in the host to a pathogenic degree. Microbes which result in pathogenic infection of a host are well known (see *Principles and Practice of Infectious Diseases,* 3rd Ed., 1990, G. Mandell et al., ed., Churchill Livingstone Inc., New York). Thus, the methods and compositions of the invention can be used in the treatment or prophylaxis of infection by pathogenic microbes associated with any condition permitting delivery of the compositions of the invention to the site of infection, including, without limitation, the treatment of superficial or surgical wounds, burns or other significant epidermal damage such as toxic epidermal necrolysis, urinary tract infections such as cystitis and urethritis, vaginitis such as vulvovaginitis and cervicitis, gingivitis, otitis externa, acne, external fungal infections, upper respiratory tract infections, gastrointestinal tract infections, subacute bacterial endocarditis and other bacterial or fungal infections to which the compositions of the invention can be effectively delivered. Representative pathogenic microbes which can be selectively killed in the practice of the invention include, without limitation, *Streptococcus pyogenes, Streptococcus agalactiae, Staphylococcus aureus, Pseudomonas aeruginosa, Escherichia coli* and other coliform bacteria, *Candida albicans,* and other infectious bacteria and fungi. The selection of a particular haloperoxidase for use in the treatment of microbial infection is preferably made based on the binding properties of the pathogenic microbe to be treated. In general, when the pathogenic microbe is a bacteria, the preferred haloperoxidase will frequently be myeloperoxidase. Due to the greater affinity of eosinophil peroxidase for *Candida albicans* and other fungi, as is further described below, EPO will commonly be the haloperoxidase of preference for the treatment of infections by these microbes.

As used herein, the term "normal flora" means bacteria which normally reside in or on body surfaces of a healthy host at symbiotic levels. Normal flora include, for example, the lactic acid family of bacteria in the mouth, intestine, or vagina of human subjects, e.g. Streptococcus (viridans) in the mouth, and *Lactobacillus sp.* (e.g., Tissier's bacillus and Doderlein's bacillus) in the intestines of breast-fed infants, external genitalia, anterior urethra and vagina. Microbes which constitute normal flora of a host are well known (e.g., see *Principles and Practice of Infectious Diseases,* supra, New York, pp. 34–36 and 161). It has been found that the haloperoxidases of the invention selectively bind to many pathogenic bacteria and fungi in preference over normal flora. The host is preferably treated with an amount of haloperoxidase which is ineffective to eliminate normal flora from the host. In some situations, such as when normal flora populations have been depressed due to overpopulation of the pathogenic microbe or for other reasons, it may be desirable to further stimulate growth of normal flora. Accordingly, the host may additionally be treated with an amount of normal flora effective to facilitate recolonization of the normal flora in the host in connection with the practice of the invention.

Antiseptic compositions of the invention generally comprise an amount of a haloperoxidase effective in the presence of a peroxide and a halide to inhibit the growth of pathogenic microbes, together with a pharmaceutically acceptable carrier. Any pharmaceutically acceptable carrier may be generally used for this purpose, provided that the carrier does not significantly interfere with the selective binding capabilities of the haloperoxide or with enzyme activity.

The antiseptic compositions can be administered in any effective pharmaceutically acceptable form to warm blooded animals, including human and animal subjects, e.g., in topical, lavage, oral, suppository, parenteral, or infusable dosage forms, as a topical, buccal, or nasal spray or in any other manner effective to deliver active haloperoxidase to a site of microbe infection. The route of administration will preferably be designed to obtain direct contact of the antiseptic compositions with the infecting microbes.

For topical applications, the pharmaceutically acceptable carrier may take the form of liquids, creams, lotions, or gels, and may additionally comprise organic solvents, emulsifiers, gelling agents, moisturizers, stabilizers, surfactants, wetting agents, preservatives, time release agents, and minor amounts of humectants, sequestering agents, dyes, perfumes, and other components commonly employed in pharmaceutical compositions for topical administration. Compositions of the invention may be impregnated into absorptive materials, such as sutures, bandages, and gauze, or coated onto the surface of solid phase materials, such as staples, zippers and catheters to deliver the compositions to a site of microbe infection. Other delivery systems of this type will be readily apparent to those skilled in the art.

Compositions designed for injection may comprise pharmaceutically acceptable sterile aqueous or nonaqueous solutions, suspensions or emulsions. Examples of suitable nonaqueous carriers, diluents, solvents, or vehicles include propylene glycol, polyethylene glycol, vegetable oils, such as olive oil, and injectable organic esters such as ethyl oleate. Such compositions may also comprise adjuvants such as preserving, wetting, emulsifying, and dispensing agents. They may be sterilized, for example, by filtration through a bacteria-retaining filter, or by incorporating sterilizing agents into the compositions. They can also be manufactured in the form of sterile solid compositions which can be dissolved or suspended in sterile water, saline, or other injectable medium prior to administration.

Solid dosage forms for oral or topical administration include capsules, tablets, pills, suppositories, powders, and granules. In solid dosage forms, the compositions may be admixed with at least one inert diluent such as sucrose, lactose, or starch, and may additionally comprise lubricating agents, buffering agents, enteric coatings, and other components well known to those skilled in the art.

Actual dosage levels of haloperoxidase in the compositions of the invention may be varied so as to obtain amounts of haloperoxidase at the site of infection effective to obtain the desired therapeutic or prophylactic response for a particular haloperoxidase and method of administration. Accordingly, the selected dosage level will depend on the nature and site of infection, the desired therapeutic response, the route of administration, the desired duration of treatment and other factors. Generally, when the haloperoxidase is myeloperoxidase, liquid dosage forms for topical or buccal administration will comprise from about 0.01 picomoles (pmol) to about 500 pmol of myeloperoxidase per ml of liquid composition, more preferably from about 0.1 pmol to about 50 pmol of myeloperoxidase per ml of liquid composition, and most preferably from about 0.5 pmol to about 5 pmol of myeloperoxidase per ml of liquid composition. Similar dosages of other haloperoxidases may be employed.

The foregoing may be better understood in connection with the following representative examples, which are presented for purposes of illustration and not by way of limitation.

EXAMPLES

Example 1

$H_2O_2$ versus HOCl Microbicidal Activity, the Effect of Erythrocytes

Materials: Bacteria, more fully described below, were grown 15 to 16 hours in trypticase soy broth (TSB) at 35° C. Yeast, more fully described below, were grown 16 hours in Sabouraud's dextrose agar (SDA) at 35° C. The cultures were centrifuged at 3,000 rpm for 15 min. and the supernatants removed. The pellet was collected and washed twice with sterile 0.85% normal saline (NS). The washed microbes were resuspended and diluted with NS to an absorbance of 0.1 at a wavelength of 540 nm, i.e., approximately $10^7$ bacteria colony forming units (CFU) per ml and approximately $10^6$ yeast CFU per ml.

A stock 3% $H_2O_2$ solution (0.88M) was used to prepare the dilutions of $H_2O_2$ required. The $H_2O_2$ concentration was verified by ultraviolet absorbance using a 240 nm extinction coefficient of 43.6 $M^{-1}$ $cm^{-1}$ or a 300 nm extinction coefficient of 1.0 $M^{-1}$ $cm^{-1}$. A stock 5.25% HOCl solution (0.7M) was used to prepare the dilutions of HOCl required.

Blood was collected by venipuncture from a healthy human volunteer. Lithium heparin was used as anticoagulant. The whole blood was centrifuged at 1,500 rpm for 15 min and the buffy coat was aspirated along with the plasma to recover the erythrocytes, i.e., red blood cells (RBC). The erythrocytes were resuspended in NS and the centrifugation, aspiration, and resuspension was repeated. The erythrocyte suspension was then passed through sterile cotton gauze to remove any remaining leukocytes. The centrifugation and aspiration was again repeated and the pellet was resuspended in 50 ml NS. The cells were counted by hemocytometer and the suspension adjusted to $10^8$ RBC per ml. The hemoglobin concentration was measured by the Drabkins technique (J. B. Henry, 1984, *Clinical Diagnosis and Management By Laboratory Methods,* 17th Edition, pp. 580–585, W.B. Saunders Co.).

Methodology: Using sterile technique, 100 μl of microbe suspension and 100 μl of NS or 100 μl of RBC suspension were added to 12×75 mm polystyrene tubes. The reaction was initiated by adding the various dilutions of the $H_2O_2$ or HOCl; the final volume was adjusted to 1 ml by the addition of NS. The reaction was allowed to run for 30 min at 23° C. After mixing to resuspend the cellular components, 100 μl of the reaction suspension was added to 900 μl of NS and serially ($_{10}$n) diluted out to $10^{-3}$. 100 μl of each dilution was then uniformly spread to dryness on pre-labeled agar plates using the "glass hockey stick" technique. Trypticase soy agar (TSA) was used for the bacteria and Sabouraud's dextrose agar (SDA) was used for the yeast. The plates were then incubated at 36° C. for about 24 to about 48 hours until read. The colonies were counted and the CFU/test were derived by multiplying the number of colonies counted by 10 (the initial dilution factor) and this value was multiplied by the plate dilution factor.

Tables 4 and 5 present the results of $H_2O_2$ (Table 4) and HOCl (Table 5) kill studies directed against three bacteria and one yeast, *Candida albicans.* Two of the bacteria, *Pseudomonas aeruginosa* and *Escherichia coli* are gram-negative bacilli; *Staphylococcus aureus* is a gram-positive coccus. These microbes were chosen for type diversity, and because they are all commonly associated with infectious pathology. These experiments were also constructed to quantify the inhibitory effect of red blood cells (RBCs) on the antiseptic action of $H_2O_2$ and HOCl. RBCs contain catalase, an enzyme that disproportionates $H_2O_2$ yielding $^3O_2$ and $H_2O$. RBCs also contain a multitude of substrates that can react with $^1O_2$ and HOCl, and thus competitively inhibit antiseptic action.

TABLE 4

Hydrogen Peroxide Microbicidal Action: Inhibitory Effect of Erythrocytes (Red Blood Cells, RBC) and Associated Hemolysis and Hemoglobin Destruction:

| Organism | $H_2O_2$, μmol | No RBC CFU: | RBC ($10^7$) CFU: | Hemoglobin: Pellet | Supern. |
|---|---|---|---|---|---|
| *P. aeruginosa* | None | 2,000,000 | 2,000,000 | 0.9 | 0.0 |
| | 790 | 0 | 0 | 0.0 | 0.0 |
| | 79 | 0 | 2,200,000 | 0.2 | 0.1 |
| | 7.9 | 4,500 | 1,700,000 | 0.9 | 0.1 |
| | 0.79 | 2,000,000 | 1,800,000 | 0.9 | 0.1 |
| | 0.079 | 1,600,000 | 1,700,000 | 0.9 | 0.1 |
| | 0.0079 | 1,200,000 | 2,000,000 | 0.9 | 0.1 |
| | 0.0008 | 1,400,000 | 1,700,000 | 0.9 | 0.1 |
| *E. coli* | None | 1,600,000 | 1,300,000 | 0.9 | 0.0 |
| | 790 | 0 | 10,000 | 0.0 | 0.0 |
| | 79 | 0 | 1,100,000 | 0.4 | 0.0 |
| | 7.9 | 670,000 | 1,300,000 | 0.9 | 0.1 |
| | 0.79 | 1,600,000 | 1,200,000 | 0.9 | 0.1 |
| | 0.079 | 1,300,000 | 1,700,000 | 0.9 | 0.1 |
| | 0.0079 | 1,600,000 | 1,200,000 | 0.9 | 0.1 |
| | 0.0008 | 1,200,000 | 1,300,000 | 1.0 | 0.0 |
| *Staph. aureus* | None | 1,200,000 | 1,300,000 | 0.9 | 0.0 |
| | 790 | 0 | 280,000 | 0.0 | 0.0 |
| | 79 | 0 | 1,600,000 | 0.4 | 0.0 |
| | 7.9 | 0 | 1,600,000 | 0.9 | 0.1 |
| | 0.79 | 880,000 | 1,500,000 | 0.9 | 0.1 |

TABLE 4-continued

Hydrogen Peroxide Microbicidal Action: Inhibitory Effect of Erythrocytes (Red Blood Cells, RBC) and Associated Hemolysis and Hemoglobin Destruction:

| Organism | $H_2O_2$, µmol | No RBC CFU: | RBC ($10^7$) CFU: | Hemoglobin: Pellet | Supern. |
|---|---|---|---|---|---|
| | 0.079 | 1,400,000 | 1,400,000 | 0.9 | 0.1 |
| | 0.0079 | 1,400,000 | 1,200,000 | 0.9 | 0.1 |
| | 0.0008 | 1,400,000 | 1,200,000 | 1.0 | 0.0 |
| Cand. albicans | None | 190,000 | 350,000 | 1.0 | 0.0 |
| | 790 | 78,000 | 150,000 | 0.0 | 0.0 |
| | 79 | 230,000 | 300,000 | 0.3 | 0.0 |
| | 7.9 | 150,000 | 380,000 | 1.0 | 0.0 |
| | 0.79 | 180,000 | 330,000 | 1.0 | 0.0 |
| | 0.079 | 170,000 | 280,000 | 0.9 | 0.0 |
| | 0.0079 | 160,000 | 290,000 | 0.9 | 0.0 |
| | 0.0008 | 270,000 | 320,000 | 1.0 | 0.0 |

The compiled data of Table 4 indicate the quantities of $H_2O_2$ required for microbe killing in the presence or absence of RBCs. For example, in the absence of RBCs. 79 µmol $H_2O_2$ are required for 100% kill of $2*10^6$ P. aeruginosa and 7.9 µmol $H_2O_2$ killed 99.8% of the $2*10^6$ P. aeruginosa. This equates to approximately 4 pmol or $2*10^{12}$ molecules $H_2O_2$/ml for each P. aeruginosa killed. In the presence of $10^7$ RBCs/ml, 790 µmol $H_2O_2$ were required to kill the $2*10^6$ P. aeruginosa, i.e., $2*10^{14}$ molecules $H_2O_2$/P. aeruginosa killed. Note that a hundredfold inhibition of killing is effected by the presence of approximately 5 RBCs per bacterium. Based on the absence of hemoglobin in both the supernatant and pellet fractions, the RBCs were completely destroyed at 790 pmol $H_2O_2$/ml and 80% destroyed at 79 µmol $H_2O_2$/ml. Note that in the presence of RBCs, there is no killing of P. aeruginosa even at a concentration of $H_2O_2$ that effected an 80% destruction of RBCs. Similar results were obtained with E. coli as the target microbe.

The inhibitory effect of RBCs is even more dramatic with Staph. aureus as the target microbe. Although slightly more susceptible to $H_2O_2$ in the absence of RBCs, i.e., approximately $9*10^{11}$ molecules $H_2O_2$/Staph. aureus killed, RBCs exert a very large inhibitory effect on killing. Approximately $4*10^{14}$ molecules $H_2O_2$/ml are required per Staph. aureus killed in the suspensions containing RBC. The presence of $10^7$ RBCs/ml effected a four hundredfold inhibition of Staph. aureus killing. As seen with the gram-negative microbes, in the presence of RBCs there is no killing of Staph. aureus at a concentration of 79 µmol/ml $H_2O_2$, a concentration that destroyed 60% of the RBCs present.

Candida albicans is exceptionally resistant to the action of $H_2O_2$. Greater than $10^{15}$ molecules $H_2O_2$ were required per Candida albicans killed in the absence or presence of RBCs.

TABLE 5

Hypochlorite Microbicidal Action: Inhibitory Effect of Erythrocytes (RBC) and Associated Hemolysis and Hemoglobin Destruction.

| Organism | HOCl, nmol | No RBC CFU: | RBC ($10^7$) CFU: | Hemoglobin: Pellet | Supern. |
|---|---|---|---|---|---|
| P. aeruginosa | None | 1,800,000 | 2,700,000 | 0.9 | 0.1 |
| | 6300 | 0 | 0 | 0.0 | 0.0 |
| | 630 | 0 | 2,000,000 | 0.0 | 1.0 |
| | 63 | 0 | 2,300,000 | 1.0 | 0.0 |
| | 6.3 | 400 | 2,100,000 | 1.0 | 0.0 |
| | 0.63 | 5,000 | 2,300,000 | 0.9 | 0.1 |
| | 0.063 | 2,100 | 2,300,000 | 1.0 | 0.0 |
| | 0.0063 | 1,200 | 2,900,000 | 0.9 | 0.1 |
| | 0.0006 | 2,100,000 | 2,500,000 | 0.9 | 0.0 |
| E. coli | None | 1,700,000 | 1,500,000 | 0.9 | 0.0 |
| | 6300 | 0 | 0 | 0.0 | 0.0 |
| | 630 | 0 | 1,400,000 | 0.1 | 0.3 |
| | 63 | 0 | 1,400,000 | 0.0 | 0.7 |
| | 6.33 | 0 | 1,700,000 | 1.0 | 0.0 |
| | 0.63 | 1,600,000 | 1,500,000 | 0.9 | 0.0 |
| | 0.063 | 1,500,000 | 1,500,000 | 1.0 | 0.0 |
| | 0.0063 | 1,500,000 | 1,600,000 | 1.0 | 0.0 |
| | 0.0006 | 1,400,000 | 1,600,000 | 1.0 | 0.0 |
| Staph. aureus | None | 1,500,000 | 1,400,000 | 1.0 | 0.0 |
| | 6300 | 0 | 0 | 0.0 | 0.0 |
| | 630 | 0 | 710,000 | 0.1 | 0.3 |
| | 63 | 0 | 1,200,000 | 0.0 | 1.0 |
| | 6.33 | 0 | 1,500,000 | 1.0 | 0.0 |
| | 0.63 | 1,300,000 | 1,400,000 | 0.9 | 0.0 |
| | 0.063 | 1,400,000 | 1,500,000 | 1.0 | 0.0 |
| | 0.0063 | 1,300,000 | 1,200,000 | 1.0 | 0.0 |
| | 0.0006 | 1,500,000 | 1,300,000 | 1.0 | 0.0 |
| Cand. albicans | None | 360,000 | 340,000 | 1.0 | 0.1 |
| | 6300 | 0 | 0 | 0.0 | 0.0 |
| | 630 | 0 | 350,000 | 0.0 | 0.2 |
| | 63 | 0 | 350,000 | 0.0 | 0.9 |
| | 6.33 | 240,000 | 250,000 | 0.9 | 0.1 |
| | 0.63 | 250,000 | 310,000 | 0.7 | 0.1 |
| | 0.063 | 280,000 | 360,000 | 0.8 | 0.1 |
| | 0.0063 | 240,000 | 340,000 | 0.9 | 0.1 |
| | 0.0006 | 290,000 | 290,000 | 0.9 | 0.1 |

The compiled data of Table 5 indicate the quantities of HOCl required for microbe killing in the presence or absence of RBCs. HOCl is a highly potent antiseptic agent. In the absence of RBCs, $10^6$ molecules HOCl are required per P. aeruginosa killed. Note that in the absence of RBCs, HOCl is a millionfold more effective than H2O2 in killing P. aeruginosa. However, its potency is severely compromised by the presence of RBCs. In the presence of RBCs, $10^{12}$ molecules HOCl are required per P. aeruginosa killed. At a ratio of approximately 5 RBCs per bacterium, erythrocytes exert a millionfold inhibition with respect to the quantity of HOCl required for P. aeruginosa killing. Note, at 630 nmol HOCl/ml there is complete lysis of RBCs but no effective microbicidal action.

Both E. coli and Staph. aureus show similar patterns of sensitivity to HOCl action, i.e., approximately $10^9$ molecules/bacterium killed in the absence of RBCs and $10^{12}$ molecules/bacterium killed in the presence of RBCs. Thus, RBCs exert a thousandfold inhibition on HOCl action, and at 63 nmol HOCl/ml there is no effective microbicidal action despite total lysis of the $10^7$ RBCs.

Candida albicans is sensitive to HOCl; $10^{11}$ molecules HOCl/ml are required per Candida albicans killed. Thus relative to $H_2O_2$, HOCl is ten thousandfold more potent for Candida albicans killing. HOCl microbicidal action was inhibited a hundredfold by the presence of RBCs, and as observed for the bacteria, 63 nmol HOCl/ml showed no effective Candida albicans killing despite total lysis of the $10^7$ RBCs present.

These data quantify the antiseptic action of $H_2O_2$ and HOCl and thus serve as reference data for comparing the antiseptic activities of haloperoxidases of the invention. The results are in keeping with the observations and conclusions of Dakin, Fleming, and Knox, described earlier. First, HOCl is a potent antiseptic agent. Knox et al. (1948) reported that HOCl is effectively microbicidal at concentrations ranging from 0.2 to 2.0 ppm, i.e., 4 to 40 nmol/ml HOCl. The data of Table 5 are in quantitative agreement with this range of activity. Second, microbes are less susceptible to the actions of $H_2O_2$ and HOCl than host cells, e.g., RBCs. The potential for host tissue damage must be considered when assessing the therapeutic efficacy of an antiseptic agent.

Example 2

Myeloperoxidase and Eosinophil Peroxidase Microbicidal Action

Cell-free myeloperoxidase is known to exert a microbicidal action in combination with an oxidizable halide, i.e., $I^-$, $Br^-$, and $Cl^-$, and $H_2O_2$ (Klebanoff, 1968). When $I^-$ is the halide, iodination is observed. With $Br^-$ or $Cl^-$ as halide, HOBr and HOCl are produced, and these potent oxidants can either directly react with microbial substrates or react with an additional $H_2O_2$ to yield $^1O_2$ as described in reaction (14) (Allen, 1975, *Bioch.Biophys.Res.Com.* 63: 675–683 and 684–691). The reactive pathway taken will in large part be determined by $H_2O_2$ availability. In accordance with reaction (7), the rate of HOCl generation:

$$d\text{HOCl}/dt = k[H_2O_2]^1 \quad (17)$$

is directly proportional to $H_2O_2$ concentration in a first order manner, but in accordance with reaction (16), the rate of $^1O_2$ generation:

$$d^1O_2/dt = k[H_2O_2]^2 \quad (18)$$

is dependent on the square of the $H_2O_2$ concentration; i.e., the reaction is second order with respect to $H_2O_2$ concentration. As such, a tenfold decrease in $H_2O_2$ results in a tenfold decrease in HOCl availability, but the same tenfold decrease in $H_2O_2$ results in a hundredfold decrease in $^1O_2$ generation. When $H_2O_2$ is limiting, direct halogenation of microbial substrates, e.g., chloramine formation, is favored. However, if adequate $H_2O_2$ is available, the generation of $^1O_2$ is favored.

Chloramine formation may be intermediate to the ultimate dioxygenation of microbial substrates. Acid pH favors chloramine dissociation yielding HOCl, and acid pH also favors microbial killing. Thus, either HOCl, chloramine, or possibly some other form of chlorinated microbial substrate, could react with $H_2O_2$ to yield a dioxygenated microbe with $^1O_2$ serving as the virtual or actual dioxygenating agent. Reaction of chlorinated and brominated organic compounds with $H_2O_2$ yields dioxygenated products, i.e., dioxetanes, identical to those obtained via $^1O_2$ reaction (Kopecky, 1982, in *Chemical and Biological Generation of Excited States,* Adam and Cilento, eds., pp.85–114, Academic Press).

The microbe killing action of $^1O_2$ has been previously considered with regard to dye-sensitized photokilling reactions. $^1O_2$ is a potent electrophile capable of reacting with the pi ($\pi$) bonding electrons of singlet multiplicity substrates. The resulting electrophilic dioxygenations are highly exergic and spin allowed, i.e., mechanistically favored (Allen et al, 1972, *Biochem.Biophys.Res.Commun.* 47: 679; Allen, 1986, *Meth. Enzymol.* 133: 449–493). A schematic depiction of the haloperoxidase mechanism for $^1O_2$ generation is presented in FIG. 1. Microbe killing by $^1O_2$ is most probably related to oxidative destruction of membrane integrity, oxidative inhibition of the enzymes required for metabolic function, and/or oxidative disintegration of the nucleic acids required for reproduction.

The microbicidal activity of myeloperoxidase and eosinophil peroxidase in the presence or absence of peroxide were determined as follows. When present, glucose and glucose oxidase were used as a source of hydrogen peroxide.

Materials: Bacteria and yeast were prepared as described in Example 1. Glucose oxidase (GOX) was purchased from Sigma Chemical Co., and a sterile stock solution of D-glucose (1 mg/ml) was prepared in NS. GOX was quantified by absorbance spectroscopy using the FAD (flavine adenine dinucleotide, Whitby, 1953, *Biochem.J.* 54:437–442) extinction coefficient of 11.3 $mM^{-1}$ $cm^{-1}$ at 450 nm. Each GOX contains two FADs, and thus an extinction coefficient of 22.6 $mM^{-1}$ $cm^{-1}$ at 450 nm was used to quantify GOX. GOX was also quantified as orthodianisidine millimolar oxidation units in the presence of excess horseradish peroxidase, as described by the supplier (Sigma Chemical Co.). One unit is that quantity of GOX that will oxidize 1 $\mu$mole of glucose to peroxide per minute under the same conditions as those used in testing.

Figure 2:
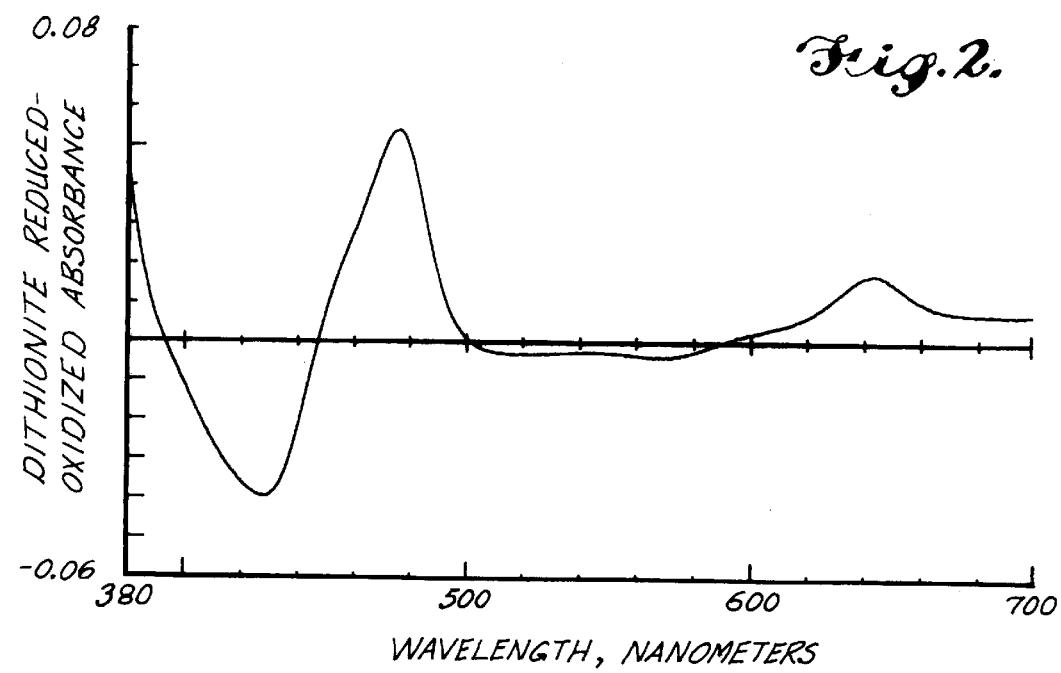
FIG. 2 is a dithionite reduced minus oxidized (R–O) difference spectrum of myeloperoxidase (MPO).
Figure 3:
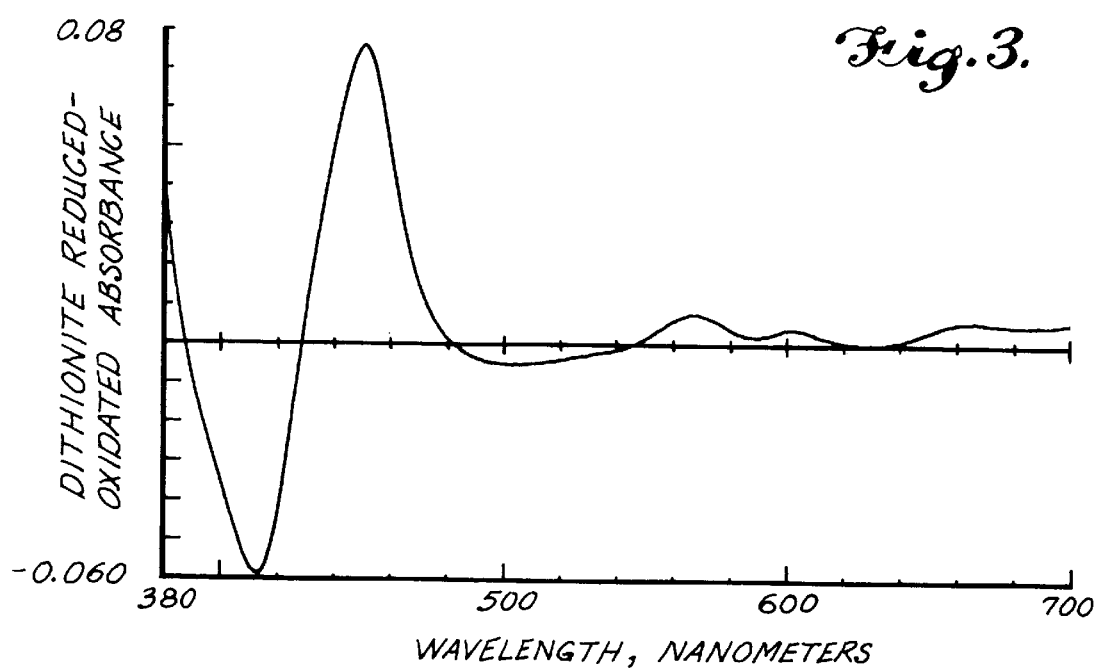
FIG. 3 is a dithionite reduced minus oxidized (R–O) difference spectrum of eosinophil peroxidase (EPO).

Myeloperoxidase (MPO) and eosinophil peroxidase (EPO) were extracted and purified from porcine leukocytes by chromatography. The quantity of haloperoxidase was assessed by reduced minus oxidized (R–O) difference spectroscopy using dithionite as the reductant. The reinheitszahl (RZ, the purity number), i.e., the ratio of 430 nm to 280 nm absorbance ($A_{430/280}$), for MPO was 0.7, indicating approximately 90% purity. The R–O difference spectrum of MPO is shown in FIG. 2; a R–O difference extinction coefficient of 50 $mM^{-1}$ $cm^{-1}$ at 475 nm was used for MPO quantification. The EPO R–O difference spectrum is shown in FIG. 3. The R–O difference extinction coefficient for EPO quantification was 56 $mM^{-1}$ $cm^{-1}$ at 450 nm. The RZ for EPO, i.e., $A_{412/280}$, was 0.7, indicating approximately 70% purity. Spectrophotometric measurements were performed on a DW2000 UV-visible spectrophotometer (SLM Instruments Co.).

Methodology: The procedure of Example 1 was generally followed, except for the inclusion of haloperoxidase, and of glucose and GOX as a source of peroxide in place of added hydrogen peroxide or hypochlorite. In this example, 100 $\mu$l of microbe suspension, 100 $\mu$l of haloperoxidase, 100 $\mu$l of glucose and 600 $\mu$l of NS were added to 12×75 mm tubes. The reaction was initiated by adding 100$\mu$l of GOX. The reaction was allowed to run for 30 min at 23° C. Diluting, plating and colony counting were as described in Example 1.

Tables 6 and 7 present the results of MPO and EPO killing of the three bacteria and one yeast previously tested in Example 1. In this Example, the microbes were diluted an additional tenfold. 100 pmol of glucose oxidase (GOX) were employed for $H_2O_2$ generation, and the final concentration of glucose per tube was 0.1 mg/ml, i.e., 0.56 $\mu$mol/ml. Since $H_2O_2$ generation is proportional to glucose availability in a first order manner, the total quantity of $H_2O_2$ generated by this system is limited to 0.56 $\mu$mol. As demonstrated by the data of Table 4, this concentration of $H_2O_2$ alone is insufficient for direct microbe killing. The microbicidal activities of MPO and EPO were tested in the presence and absence of the GOX-feeder system, as shown in Tables 6 and 7.

TABLE 6

Myeloperoxidase (MPO) Kill Capacity in the Presence and Absence of Glucose Oxidase (GOX) as $H_2O_2$ Generator:

| Organism: | MPO, pmol | GOX, none CFU: | GOX, 100 pmol CFU: |
|---|---|---|---|
| P. aeruginosa | None | 130,000 | 100,000 |
|  | 450 | 100,000 | 0 |
|  | 90 | 78,000 | 0 |
|  | 18 | 50,000 | 0 |
|  | 3.6 | 110,000 | 1,000 |
|  | 0.7 | 100,000 | 4,000 |
| E. coli | None | 243,000 | 287,000 |
|  | 450 | 149,000 | 0 |
|  | 90 | 217,000 | 0 |
|  | 18 | 113,000 | 0 |
|  | 3.6 | 208,000 | 430,000 |
|  | 0.7 | 178,000 | 790,000 |
| Staph. aureus | None | 384,000 | 298,000 |
|  | 450 | 222,000 | 0 |
|  | 90 | 379,000 | 0 |
|  | 18 | 584,000 | 43,000 |
|  | 3.6 | 263,000 | 78,000 |
|  | 0.7 | 217,000 | 114,000 |
| Cand. albicans | None | 240,000 | 520,000 |
|  | 450 | 180,000 | 0 |
|  | 90 | 420,000 | 0 |
|  | 18 | 300,000 | 0 |
|  | 3.6 | 740,000 | 26,000 |
|  | 0.7 | 400,000 | 340,000 |

The microbes (100 μl), MPO (100 μl), and glucose (100 μl, 1 mg/ml) plus or minus GOX (100 pmol, i.e., approximately 1 mM-unit, in 100 μl) were added to NS for a final volume of 1.0 ml.

TABLE 7

Eosinophil peroxidase (EPO) Kill Capacity in the Presence and Absence of Glucose Oxidase (GOX) as $H_2O_2$ Generator:

| Organism: | EPO, pmol | GOX, none CFU: | GOX, 100 pmol CFU: |
|---|---|---|---|
| P. aeruginosa | None | 160,000 | 220,000 |
|  | 500 | 110,000 | 0 |
|  | 100 | 500,000 | 0 |
|  | 20 | 110,000 | 1,000 |
|  | 4 | 180,000 | 11,000 |
|  | 0.8 | 140,000 | 190,000 |
| E. coli | None | 180,000 | 140,000 |
|  | 500 | 100,000 | 0 |
|  | 100 | 91,000 | 0 |
|  | 20 | 150,000 | 0 |
|  | 4 | 170,000 | 27,000 |
|  | 0.8 | 280,000 | 100,000 |
| Staph. aureus | None | 180,000 | 100,000 |
|  | 500 | 110,000 | 0 |
|  | 100 | 140,000 | 0 |
|  | 20 | 130,000 | 0 |
|  | 4 | 100,000 | 0 |
|  | 0.8 | 180,000 | 3,500 |
| Cand. albicans | None | 110,000 | 100,000 |
|  | 500 | 170,000 | 0 |
|  | 100 | 110,000 | 0 |
|  | 20 | 110,000 | 0 |
|  | 4 | 110,000 | 0 |
|  | 0.8 | 100,000 | 0 |

The microbes (100 μl), EPO (100 μl), and glucose (100 μl, 1 mg/ml) plus or minus GOX (100 pmol, i.e., approximately 1 mM-unit, in 100 μl) were added to NS for a final volume of 1.0 ml.

MPO and especially EPO are basic, i.e., cationic (positively charged), proteins, and some cationic proteins exert a microbicidal action in the absence of any demonstrable redox enzymatic action. However, under the present conditions of testing, essentially no direct, peroxide-independent, microbicidal action was noted with either MPO or EPO over the 0.7 to 500 pmol/ml concentration range. Likewise, a 100 pmol/ml concentration of GOX, i.e., approximately 1 mM o-dianisidine oxidation units activity under the conditions of testing, did not exert a detectable microbicidal action in the absence of XPO. This is expected since the total conversion of 0.1 mg (0.56 μmol) glucose to 0.56 μmol $H_2O_2$ by GOX would be insufficient for microbicidal action. Addition of this same quantity of GOX to picomole per milliliter concentrations of either MPO or EPO produces a potent microbicidal action against all of the microbes tested. The MPO and EPO data also appear to demonstrate a killing specificity, set forth in more detail, infra.

Example 3

The Effect of Myeloperoxidase on Peroxide Microbicidal Action

Materials: The bacteria and yeast were prepared as described in Example 1. MPO was prepared as described in Example 2.

Methodology: The procedure of Example 1 was generally followed, in which 100 μl of microbe suspension, 100 μl of MPO (10 pmol), and 800 μl of the indicated $H_2O_2$ concentration in acetate buffer (AcB), pH 6, were added to 12×75 mm tubes. The reaction was initiated by $H_2O_2$ addition. The reactions were run in the presence of 100 μmol Cl⁻ (Table 8A), or in the absence of halide or in the presence of 10 μmol Br⁻ (Table 8B). The reaction was allowed to run for 30 min at 23° C. Diluting, plating and colony counting were as described in Example 1.

TABLE 8A $H_2O_2$ Kill Capacity in the Presence and Absence of Myeloperoxidase (10 pmol MPO) and Chloride (100 μmol Cl):

| Organism: | $H_2O_2$, μmol | MPO, none CFU: | MPO, 10 pmol CFU: |
|---|---|---|---|
| P. aeruginosa | None | 2,100,000 | 2,500,000 |
|  | 700 | 0 | 0 |
|  | 70 | 0 | 0 |
|  | 14 | 23,000 | 0 |
|  | 2.8 | 950,000 | 0 |
|  | 0.56 | 1,800,000 | 0 |
|  | 0.112 | 2,700,000 | 0 |
|  | 0.0224 | 2,500,000 | 13,000 |
|  | 0.00448 | 1,800,000 | 220,000 |
|  | 0.000896 | 2,600,000 | 2,500,000 |
| E. coli | None | 3,200,000 | 2,500,000 |
|  | 700 | 0 | 0 |
|  | 70 | 0 | 0 |
|  | 14 | 40,000 | 0 |
|  | 2.8 | 1,700,000 | 0 |
|  | 0.56 | 2,800,000 | 0 |
|  | 0.112 | 3,200,000 | 0 |
|  | 0.0224 | 3,600,000 | 37,000 |
|  | 0.00448 | 2,100,000 | 0 |
|  | 0.000896 | 3,000,000 | 19,000 |
| Staph. aureus | None | 2,400,000 | 1,700,000 |
|  | 700 | 0 | 0 |
|  | 70 | 0 | 0 |
|  | 14 | 6,600 | 1,300,000 |
|  | 2.8 | 1,500,000 | 1,900,000 |
|  | 0.56 | 1,600,000 | 0 |
|  | 0.112 | 2,000,000 | 0 |
|  | 0.0224 | 2,500,000 | 0 |
|  | 0.00448 | 2,700,000 | 30,000 |
|  | 0.000896 | 2,300,000 | 2,300,000 |
| Cand. albicans | None | 620,000 | 760,000 |
|  | 700 | 360,000 | 320,000 |
|  | 70 | 320,000 | 380,000 |

TABLE 8A-continued

H$_2$O$_2$ Kill Capacity in the Presence and Absence of Myeloperoxidase (10 pmol MPO) and Chloride (100 µmol Cl):

| Organism: | H$_2$O$_2$, µmol | MPO, none CFU: | MPO, 10 pmol CFU: |
|---|---|---|---|
| | 14 | 480,000 | 460,000 |
| | 2.8 | 440,000 | 0 |
| | 0.56 | 460,000 | 0 |
| | 0.112 | 420,000 | 0 |
| | 0.0224 | 540,000 | 0 |
| | 0.00448 | 440,000 | 180,000 |
| | 0.000896 | 420,000 | 520,000 |

The microbes (100 µl), MPO (100 µl), and the indicated quantity of H$_2$O$_2$ were added to NS for a final volume of 1.0 ml.

TABLE 8B

H$_2$O$_2$ Kill Capacity of Myeloperoxidase (10 pmol MPO) in the Presence and Absence of Bromide (10 µmol Br):

| Organism | H$_2$O$_2$, µmol | No Halide CFU: | 10 µmol Br CFU: |
|---|---|---|---|
| P. aeruginosa | None | 2,600,000 | 1,500,000 |
| | 0.56 | 2,800,000 | 0 |
| | 0.112 | 2,000,000 | 0 |
| | 0.0224 | 2,200,000 | 2,000 |
| | 0.00448 | 2,200,000 | 23,000 |
| | 0.000896 | 2,600,000 | 2,300,000 |
| | 0.0001792 | ND[1] | 3,100,000 |
| E. coli | None | 520,000 | 1,700,000 |
| | 0.56 | 1,400,000 | 0 |
| | 0.112 | 970,000 | 0 |
| | 0.0224 | 1,900,000 | 0 |
| | 0.00448 | 1,200,000 | 600 |
| | 0.000896 | 780,000 | 910,000 |
| | 0.0001792 | ND | 1,600,000 |
| | 0.0000358 | ND | 1,300,000 |
| Staph. aureus | None | 3,700,000 | 3,800,000 |
| | 0.56 | 3,500,000 | 0 |
| | 0.112 | 3,300,000 | 0 |
| | 0.0224 | 3,000,000 | 0 |
| | 0.00448 | 3,300,000 | 0 |
| | 0.000896 | 3,800,000 | 54,000 |
| | 0.0001792 | ND | 500 |
| | 0.0000358 | ND | 200,000 |
| | 0.0000072 | ND | 3,200,000 |
| Cand. albicans | None | 820,000 | 450,000 |
| | 0.56 | 920,000 | 0 |
| | 0.112 | 940,000 | 0 |
| | 0.0224 | 660,000 | 500 |
| | 0.00448 | 880,000 | 5,600 |
| | 0.000896 | 880,000 | 580,000 |
| | 0.0001792 | ND | 23,000 |
| | 0.0000358 | ND | 63 |
| | 0.0000072 | ND | 540,000 |

[1] Not done.

The data of Tables 8A and 8B illustrate the potentiating effect of MPO on the microbicidal action of H$_2$O$_2$ using 100 µmol Cl$^-$ and 10 µmol Br$^-$ as the halide cofactor, respectively. At a concentration of 10 pmol/ml, MPO is not rate limiting with respect to MPO:Cl$^-$(or Br$^-$):H$_2$O$_2$ dependent killing of the 10$^6$ target microbes. This quantity of MPO provides an essentially zero order condition with respect to XPO in microbicidal kinetics, and as such, if halide is not limiting, and if the halide:peroxide ratio is not inhibitory (described in full infra), killing will be proportional to H$_2$O$_2$ availability. The catalytic effect of MPO on H$_2$O$_2$ microbicidal action was tested using the same bacteria and yeast previously described.

The concentrations of MPO and halide were held constant and H$_2$O$_2$ was varied over a wide range of concentrations. Note in the data of Table 8A that the H$_2$O$_2$ kill activities in the absence of MPO are comparable to the direct H$_2$O$_2$ kill activities in the absence of RBC. See the compiled data of Table 4. In both studies approximately 10$^{12}$ molecules H$_2$O$_2$ are required per bacteria killed, and H$_2$O$_2$ was ineffective in killing Candida albicans even at a concentration of 700 µmol/ml, i.e., 2.4%9 H$_2$O$_2$. The data of Table 8B further establish that bromide can serve as the halide for MPO microbicidal action. Essentially, no killing was observed using the MPO-H$_2$O$_2$ system in the absence of halide.

In the absence of H$_2$O$_2$, MPO did not kill the microbes tested, but MPO increased microbicidal capacity of H$_2$O$_2$ by several magnitudes. At relatively high concentrations, e.g., in the µmol/ml range, H$_2$O$_2$ can inhibit XPO catalytic activity unless there is a proportional increase in halide concentration. The inhibition of MPO-dependent Candida albicans killing at high H$_2$O$_2$ concentrations results from the greatly decreased Cl$^-$:H$_2$O$_2$ ratio. Lack of an observable effect with the bacteria may be the result of the much greater MPO independent killing activity of H$_2$O$_2$ with respect to these bacteria; i.e., killing occurs despite MPO inhibition. Note that inhibition of Staph. aureus killing is observed with 2.8 and 14 µmol peroxide. MPO can be protected from the action of H$_2$O$_2$ by increasing the concentration of halide or decreasing the pH. However, it is probably more appropriate to decrease the concentration H$_2$O$_2$ added, or to introduce a H$_2$O$_2$ generator system that would insure a relatively low but dynamically sustained H$_2$O$_2$ availability. The ratio of chloride/peroxide is the critical factor with regard to haloperoxidase stability and functional catalytic activity. A broad range of peroxide concentrations may be employed as long as the chloride/peroxide ratio is maintained preferably above about 50. For example, if the chloride concentration is 100 µmol/ml, i.e., approximately equal to physiological plasma concentration, then the peroxide concentration should be maintained below 2 µmol/ml and preferably below 1 µmol/ml.

Picomole quantities of MPO produce a greater than ten thousandfold increase in H$_2$O$_2$ bactericidal action. With 10 pmol MPO, approximately 10$^8$ molecules H$_2$O$_2$ are required per bacterium killed regardless of the bacteria tested. This is equivalent to a 0.01 ppm concentration of H$_2$O$_2$. This lower range of peroxide concentration might be extended still lower by optimum adjustment of the chloride/peroxide or bromide/peroxide ratio. As such, the bactericidal action of MPO-catalyzed H$_2$O$_2$ surpasses that reported for HOCl, i.e., 0.2 to 2.0 ppm (Knox et al., 1948). Recall that in Table 5 the molecules/microbe killed ratio using HOCl was approximately 10$^9$ for E. coli and Staph. aureus, but was approximately 10$^6$ for P. aeruginosa. With exception, the MPO-catalyzed H$_2$O$_2$ microbicidal action is greater than that of HOCl when equated on a concentration or molecule/microbe basis.

As demonstrated in the data of Tables 4, 8A and 8B, Candida albicans is highly resistant to the direct action of H$_2$O$_2$, but introduction of 10 pmol MPO in the presence of Cl$^-$ or Br$^-$ produces a greater than hundred-thousandfold increase in H$_2$O$_2$ killing activity with respect to this yeast. MPO-dependent H$_2$O$_2$ killing of Candida albicans is effected at a molecule/yeast ratio of approximately 5*10$^9$. Although the yeast killing capacity of the MPO system is less potent than that observed for the bacteria, the killing system is extraordinarily potent in comparison with conventional antiseptics or antibiotics. Based on comparison of the data of Tables 5 and 8, MPO-catalyzed H$_2$O$_2$-dependent Candida albicans killing is greater than that observed using HOCl.

Example 4

The Effect of Erythrocytes on MPO-GOX Microbicidal Action

Materials: Bacteria and yeast were prepared as described in Example 1. MPO, GOX, and RBC suspensions were prepared as described in Example 2, except that glucose was used at a tenfold higher concentration, i.e., 10 mg/ml stock glucose.

Methodology: The procedure of Example 2 was followed, in which 100 μl of microbe suspension, 100 μl of MPO, 100 μl glucose (1 mg/100 μl), plus or minus 100 μl RBC suspension, and sufficient NS to yield 0.9 ml volume were added to 12×75 mm tubes. The reaction was initiated by addition of 100 μl of GOX (100 pmol/ml; approximately 1 mM o-dianisidine oxidation units). The reaction was allowed to run for 30 min at 23° C. Diluting, plating and colony counting were as described in Example 1.

The data of Table 9 once again illustrate the potent microbicidal activity of MPO in combination with glucose-:GOX as the $H_2O_2$ generation system. The first portion of the procedure of this Example 4 differed from the procedure described in Example 2 (data of Table 6) only in that the glucose concentration was increased tenfold. 100 pmol GOX were employed for $H_2O_2$ generation, and the final concentration of glucose per tube was 1.0 mg/ml, i.e., 5.6 μmol/ml. Therefore, the total quantity of $H_2O_2$ generated by this system is limited to 5.6 μmol. Based on the data of Table 4, this quantity of $H_2O_2$ is sufficient for direct microbicidal action in the absence but not in the presence of RBCs.

This example was designed to assess the effect of RBCs on MPO microbicidal action. The RBC:bacterium ratios were approximately 2 and the RBC:yeast ratio was approximately 40. These ratios are within the same magnitudinal range as in the experiments compiled in Tables 4 and 5. In accordance with the cell size differences, erythrocyte mass is several magnitudes greater than that of the microbes.

TABLE 9

Erythrocyte (Red Blood Cell, RBC) Inhibition of Myeloperoxidase:Glucose Oxidase (MPO:GOX) Microbicidal Action: Associated Hemolysis and Hemoglobin Destruction:

| Organism | MPO, pmol | No RBC CFU: | RBC ($10^7$) CFU: | Pellet | Hemoglobin: Supern. |
|---|---|---|---|---|---|
| P. aeruginosa | None | 4,500,000 | 4,500,000 | 0.6 | 0.0 |
|  | 100.0 | 0 | 4,600 | 0.0 | 0.8 |
|  | 33.3 | 0 | 5,200 | 0.0 | 0.9 |
|  | 11.1 | 0 | 1,600 | 0.0 | 0.9 |
|  | 3.7 | 0 | 3,700 | 0.0 | 1.0 |
|  | 1.2 | 0 | 1,200 | 0.2 | 0.9 |
|  | 0.4 | 0 | 4,400 | 0.8 | 0.4 |
|  | 0.13 | 0 | 22,000 | 0.7 | 0.0 |
| E. coli | None | 4,800,000 | 4,200,000 | 0.9 | 0.0 |
|  | 100.0 | 0 | 0 | 0.0 | 0.5 |
|  | 33.3 | 0 | 0 | 0.0 | 0.6 |
|  | 11.1 | 0 | 300 | 0.0 | 0.6 |
|  | 3.7 | 0 | 0 | 0.1 | 0.6 |
|  | 1.2 | 0 | 2,000 | 1.0 | 0.0 |
|  | 0.4 | 0 | 1,400 | 0.9 | 0.0 |
| Staph. aureus | None | 4,900,000 | 5,400,000 | 0.7 | 0.0 |
|  | 100.0 | 0 | 0 | 0.0 | 0.7 |
|  | 33.3 | 0 | 0 | 0.0 | 0.7 |
|  | 11.1 | 0 | 0 | 0.0 | 0.6 |
|  | 3.7 | 0 | 0 | 0.0 | 0.5 |
|  | 1.2 | 0 | 5,000 | 1.0 | 0.1 |
|  | 0.4 | 0 | 3,000 | 1.0 | 0.0 |
| Cand. albicans | None | 200,000 | 260,000 | 0.8 | 0.0 |
|  | 100.0 | 0 | 90,000 | 0.0 | 0.9 |
|  | 33.3 | 0 | 120,000 | 0.0 | 1.0 |
|  | 11.1 | 0 | 110,000 | 0.0 | 0.9 |
|  | 3.7 | 0 | 180,000 | 0.0 | 1.3 |
|  | 1.2 | 100 | 90,000 | 0.4 | 0.9 |
|  | 0.4 | 310,000 | 190,000 | 0.9 | 0.5 |
|  | 0.13 | 130,000 | 190,000 | 0.8 | 0.0 |

The microbes (100 μl), MPO (100 μl), glucose (100 μl, 10 mg/ml), GOX (100 pmol, i.e., approximately 1 mM-unit, in 100 μl) plus or minus $10^7$ RBC (100 μl) were added to NS for a final volume of 1.0 ml.

As shown in Table 9, bactericidal capacity of the MPO-GOX system is inhibited by the presence of RBCs, but the inhibitory effect is relatively small. The approximately 6 μmol quantity of $H_2O_2$ should exert detectable bactericidal action but no fungicidal action in the absence of RBCs, and no detectable bactericidal or fungicidal action in the presence of RBCs. The data of Table 9 illustrate that the MPO-GOX system effects potent microbicidal action even in the presence of RBCs. This MPO-GOX system caused hemolysis when MPO was used at a concentration greater than about 1 pmol/ml. However, bactericidal action without associate hemolytic activity is observed in the sub-pmol/ml range of MPO concentration. This latter observation is of profound importance in that it suggests a selectivity with respect to the destructive activity of MPO; i.e., under optimum conditions, bacteria can be selectively killed with minimal collateral damage to host cells.

Example 5

Spectral Analysis of MPO Binding to Microbes $^1O_2$ offers several advantages as an antiseptic agent. It is a broad spectrum yet relatively selective electrophilic oxygenating agent capable of reacting with key amino acids, unsaturated lipids and nucleic acids. The reactive rate constants ($k_r$, in $M^{-1}sec^{-1}$) for $^1O_2$ reaction with tryptophan, histidine, and methionine are $3*10^7$ (Matheson and Lee, 1979, Photochem.Photobiol. 29: 879–881), $8.8*10^7$, and $2*10^7$ (Kraljic and Sharpatyi, 1978, Photochem.Photobiol. 28: 583–586) respectively. These essential amino acids are required components of protein structure and typically participate in enzyme catalytic mechanisms. As such, a "trace" concentration of $^1O_2$ could reactively inhibit a large number of the enzymes required for metabolic function (Green, 1941).

Spin multiplicity change, i.e., intersystem crossing, is required for relaxation of $^1O_2$ to $^3O_2$. In accordance with Wigner's spin conservation rules, metastability results from the low probability associated with any change in spin state. As such, the $^1O_2$ excited state of oxygen is metastable with a aqueous reactive lifetime in the is range (Merkel and Kearns, 1972, J.Am.Chem.Soc. 94: 1029–1030). Thus, in addition to the mechanistic restrictions imposed by its electrophilic character, $^1O_2$ reactivity is also confined to a temporal domain governed by its lifetime. "The lifetime of 102 in aqueous solution has been found to be in the μs region, during which interval it can diffuse mean radial distances of at least 1,000 angstroms. Thus it is able to react at loci remote from the site of generation" (Lindig and Rodgers, 1981, Photochem.Photobiol. 33: 627–634).

This time-gated restriction of reactivity imposes a biologically necessary limitation on the region and extent of $^1O_2$ oxidative damage by linking the volume of damage to the proximity of the generator enzyme, XPO. Stated differently, reaction in three dimensional space is limited by the forth dimensional quality of the reactant, i.e., the lifetime of $^1O_2$. If the XPO binds to the surface of the microbe, a volume of oxidative damage with a radius of approximately 1000 angstroms (0.1 µm or 100 nm) from the XPO locus would be sufficient to destroy essentially any component of the microbe. The diameters of bacteria range from approximately 0.5 to 1.0 µm, and the membrane and peptidoglycan region is typically less than 50 nm thick. Thus key components of the microbe membrane as well as essential cytoplasmic enzymes and nucleic acids are susceptible to $^1O_2$ generated by surface-bound XPO.

If the XPO is in close proximity to the target microbe, this reactive volume limitation serves to confine oxygenation damage to the microbe. Furthermore, if the binding of XPO to microbes is selective relative to eukaryotic cells, then microbicidal action could be effected with a minimum of bystander host cell damage, e.g., hemolysis.

Myeloperoxidase (MPO) and especially eosinophil peroxidase (EPO) are cationic glycoproteins. Both XPO's also bind to a number of lectins, e.g., concanavalin A. As such, these XPO might bind to microbes via electrostatic charges, lectin binding, or by some additional mechanism. If binding to target microbes is sufficiently selective, as is demonstrated herein, the antiseptic potential of volume-limited oxygenation activity of the XPO system may be fully realized.

Materials: The bacteria were grown approximately 16 hours in trypticase soy broth (TSB) at 35° C. The cultures were then centrifuged (3,000 rpm for 15 min) and the supernatant removed. The pellet was collected and washed twice with sterile 0.85% normal saline (NS). The washed microbes were resuspended to a density of approximately $10^9$ bacteria/ml. Final quantification was by hemocytometer count. MPO was prepared as described in Example 2.

Methodology: Various dilutions of MPO were added to a suspension of $2.1*10^9$ Staph. aureus; the final volume was 1 ml. The suspension was mixed gently for 30 minutes and then centrifuged at 2,000 rpm for 10 minutes. The supernatant was removed and saved for quantification of free MPO. The pellet was washed by resuspending in 5 equivalent volumes of NS. After thorough mixing for about 10 minutes on a tilt table, the bacteria were again centrifuged. The supernatant was discarded and the pellet was resuspended to original volume with NS.

R–O difference spectroscopic measurements were modified from those described in Example 2, as follows. The relatively dense Staph. aureus suspension introduced a signal-to-noise problem with regard to quantifying MPO based on the R–O difference extinction coefficient of 50 $mM^{-1} cm^{-1}$ at 475 nm. This problem was solved by averaging the R–O difference absorptions at 449 and 500 nm. This average was then subtracted from the R–O difference absorption at 475 nm. The adjusted R–O difference absorption at 475 nm was used to calculate the MPO concentration using the 50 $mM^{-1} cm^{-1}$ extinction coefficient.

Figure 4:
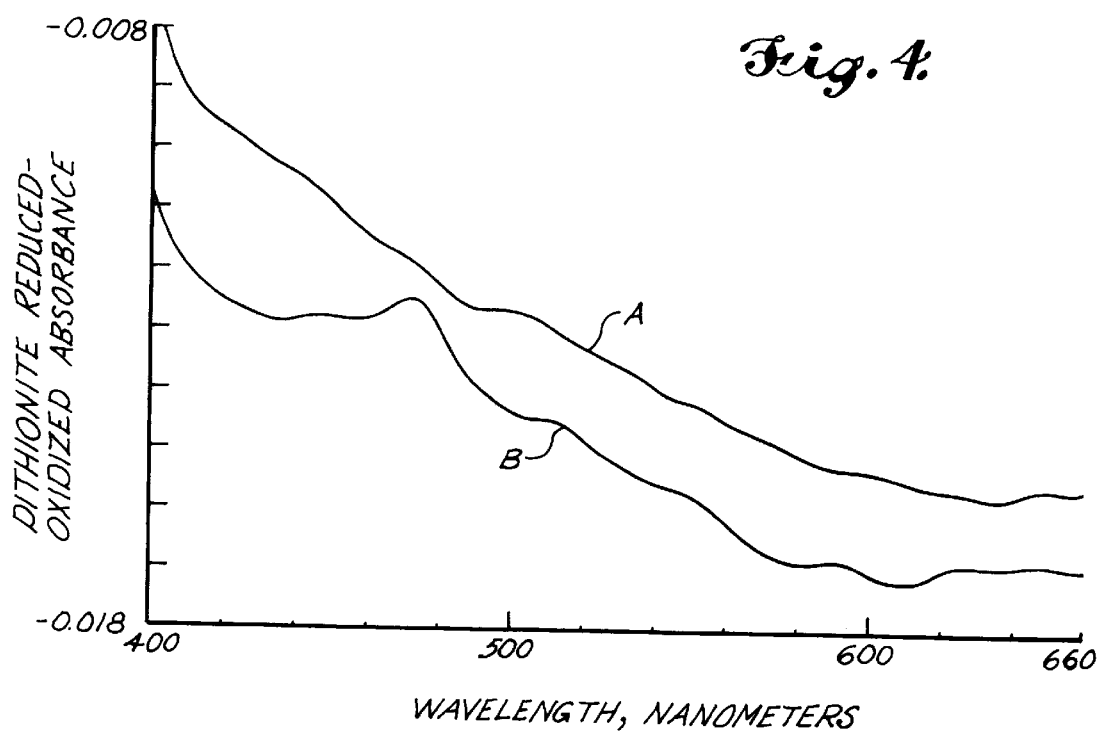
FIG. 4 shows the dithionite reduced minus oxidized (R–O) difference spectra of a Staphylococcus aureus suspension before (spectrum A) and after (spectrum B) exposure to myeloperoxidase (MPO).
Figure 5:
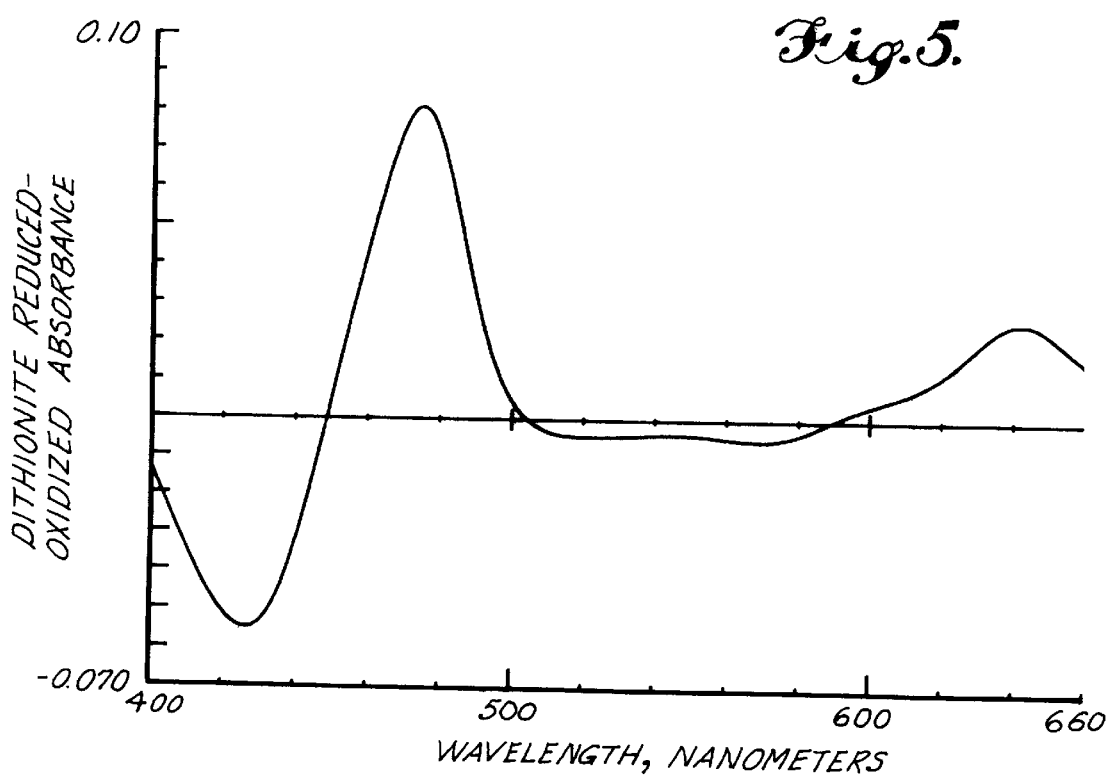
FIG. 5 shows the dithionite R–O difference spectrum of MPO remaining in solution (free MPO) after exposure to and removal of bacteria by centrifugation.

FIG. 4 depicts the dithionite reduced minus oxidized (R–O) difference spectra of the Staph. aureus suspension pre and post MPO exposure, i.e., bound MPO. FIG. 5 depicts the R–O spectrum of the MPO remaining in solution after centrifugal removal of the bacteria, i.e., free MPO. Approximately 20 pmol MPO bound to $2.1*10^9$ Staph. aureus, while 1,560 pmol MPO remained in the one ml volume of solution. As such, the MPO bound:free ratio is 0.013 with approximately 5,700 molecules MPO bound per bacterium. Serial $2^n$ dilution from this starting MPO concentration yielded MPO bound:free ratios of 0.020 and 0.018 where n was 1 and 2 respectively. Likewise, the number of MPO molecules bound per bacterium was 4,100 and 1,700 when n was 1 and 2 respectively.

Unfortunately, the signal:noise ratios were very poor at higher MPO dilutions. Thus direct spectroscopic measurement of bound MPO is limited to the relatively low affinity range of binding. Despite this limitation in sensitivity, these spectroscopic measurements provide direct evidence of MPO binding to bacteria. In fact, if a sufficient number of bacteria and adequate MPO are combined, the binding of MPO to bacteria can be visually observed with the unaided eye.

Example 6

Scatchard Analysis of MPO Binding to Microbes

The Scatchard method is frequently employed as a graphic method for analyzing binding affinity (see Rodbard, 1981, in: Ligand Assay, Langan and Clapp, eds., pp 45–101, Masson Publ., New York). The dynamics of XPO binding to a microbe:

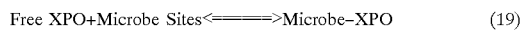

can be expressed according to the mass action relationship:

$$K_{aff} = \frac{[Microbe - XPO]}{[Free\ XPO][Microbe\ Sites]} \quad (20)$$

and therefore:

$$\frac{[Microbe - XPO]}{[Free\ XPO]} = K_{aff}[Microbe\ Sites] \quad (21)$$

Thus the ratio of bound to free MPO is a linear function of the number of sites per microbe multiplied by the affinity constant, $K_{aff}$.

Materials: P. aeruginosa, E. coli, Salmonella typhimurium, and Staph. Aureus were prepared as described in Example 1. Streptococcus sps. and Lactobacillus sps. were prepared as described in Example 1 except that Todd-Hewitt and MRS media were used to support growth of each group, respectively. Candida albicans and Cryptococcus neoformans were prepared in like manner except that Sabouraud's dextrose agar media was employed. RBCs were prepared as previously described in Example 1. The bacteria and yeast were quantified by hemocytometer count. MPO was prepared and quantified as described in Example 2.

Methodology: Serial $1.5^n$ or $2^n$ dilutions of MPO were prepared and combined with the microbes. The MPO concentration was varied and the number of microbes was held constant. Approximately $10^5$ to $10^6$ bacteria or yeast cells were employed per test. One volume of the microbe preparation was added to one volume of the MPO dilution or NS. The suspension was mixed and allowed to incubate for 30 minutes at 23° C. The suspension was then centrifuged at 15,000 rpm for 5 minutes on an Eppendorf Model 5414 high speed centrifuge. The supernatant was decanted and saved for testing. The pellet was resuspended and washed with an equivalent volume of NS. The resuspended pellet was recentrifuged and the wash supernatant discarded. The pellet was resuspended to one volume, i.e., the original volume of the microbe preparation.

The MPO activity of each MPO dilution was measured as its product luminescence using $Br^-$ as halide, $H_2O_2$ as oxidant and luminol as the chemiluminigenic substrate as described in copending U.S. patent application Ser. No.

417,276 filed Oct. 5, 1989. A 100 µl aliquot of each MPO dilution was tested. Each sample was added to a 12×75 mm test tube. Luminescence was measured with a LB950 luminometer (Berthold Instruments, Wildbad, Germany). Two injectors were employed. The first injected 300 µl of 150 µM (45 nmol) luminol in 50 mM acetate buffer (AcB), pH 5 containing 5 µmol Br⁻. A 20 second measurement was taken following the injection of 300 µl of 16.7 mM (5 µmol) $H_2O_2$ from the second injector.

The free and microbe-bound MPO activities were measured using the same methodology except that 100 µl of test supernatant, i.e., free MPO, or 100 µl of MPO-microbe suspension, i.e., bound MPO, were added per tube. By this methodology, the free MPO is diluted by a factor of two relative to the bound MPO. This was allowed in order to extend the effective range of free MPO measurement. The activity values for the free MPO measurements were therefore multiplied by a factor of two prior to use in Scatchard analysis.

The great sensitivity of luminescence for quantifying XPO activity makes it ideally suited for measuring pmol and sub-pmol quantities of free and microbe-bound MPO as required for Scatchard analysis of binding affinity. The first step in such analysis is construction of a standard curve equating the measured CL activity to a molecular quantity of MPO.

Figure 6A:
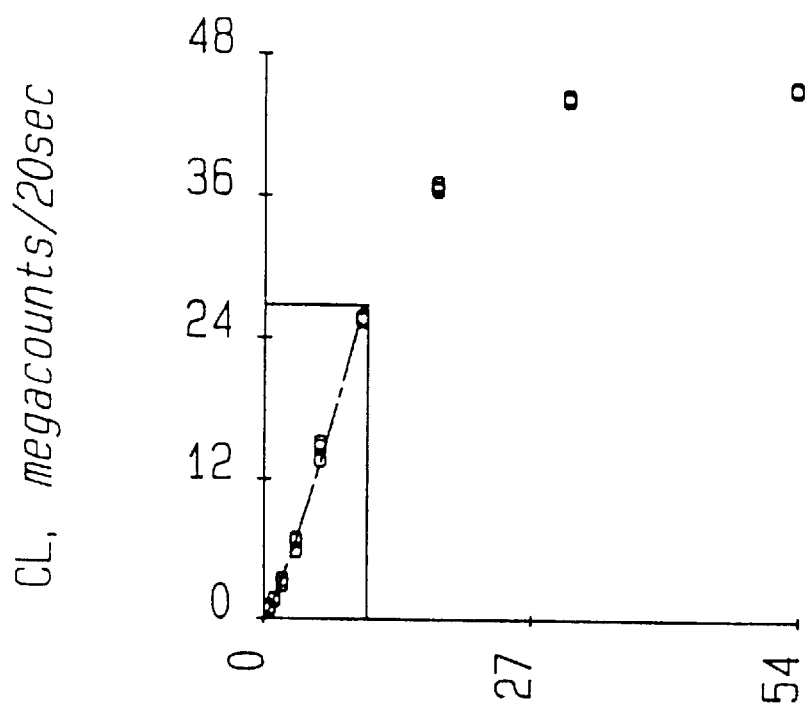
FIG. 6A is a plot of chemiluminescence (CL), expressed as megaphotons per 20 seconds, resulting from MPO-dependent luminol oxidation versus the MPO concentration employed.
Figure 6B:
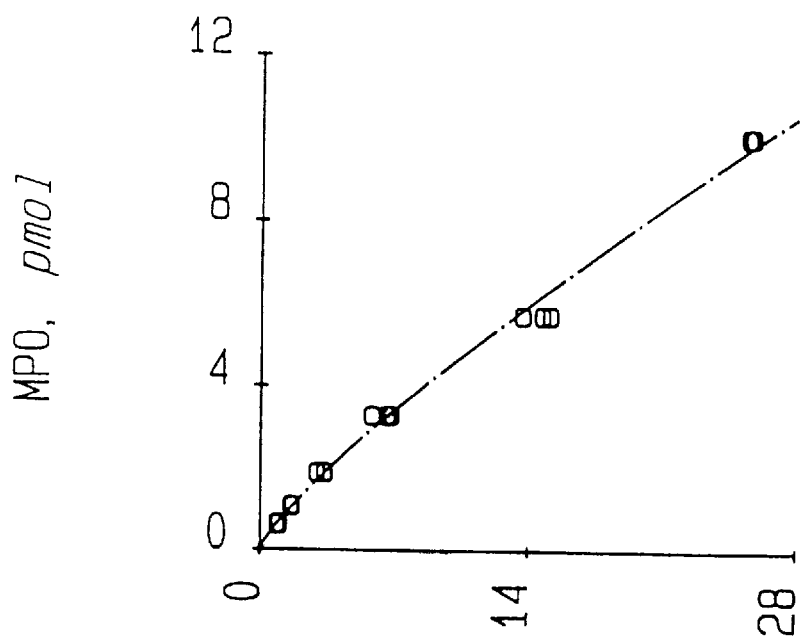
FIG. 6B is a restricted range replot of data shown in FIG. 6A in which the x and y axes have been reversed from FIG. 6A.

FIG. 6 is the plot of chemiluminescence (CL) expressed as megaphotons/20 s, i.e., $10^6$ photons/20 seconds, versus the pmol quantity of MPO tested. The relationship of MPO to CL is essentially linear in the 0 to 10 pmol range of MPO concentration, as shown by the plot of this range in FIG. 6B, in which the x and y axes have been reversed from FIG. 6A. Regression analysis yields the equation:

$$CL_{photons/20\ s} = k*[MPO_{pmol}]^p \quad (22)$$

where k is the constant and the superscript p is the reaction order with respect to MPO concentration. The actual values for the equation:

$$CL_{megaphotons/20\ s} = 3.35*[MPO_{pmol}]^{1.15} \quad (23)$$

or its reciprocal expression:

$$MPO_{pmol} = 0.702*[CL_{megaphotons/20\ s}]^{0.811} \quad (24)$$

were determined by averaging ten separate standard range determinations. The coefficient of determination, i.e., $r^2$, is 0.987. The pmol values for MPO are based on initial quantification by R–O difference spectroscopy and estimation based on serial $2^n$ dilution. Dilution in polystyrene tubes is associated with some loss due to tube binding; this is especially apparent at relatively high dilutions. As such, the estimation of reaction order is slightly skewed. The p value of 1.15 is thus slightly greater than first order.

Figure 7A:
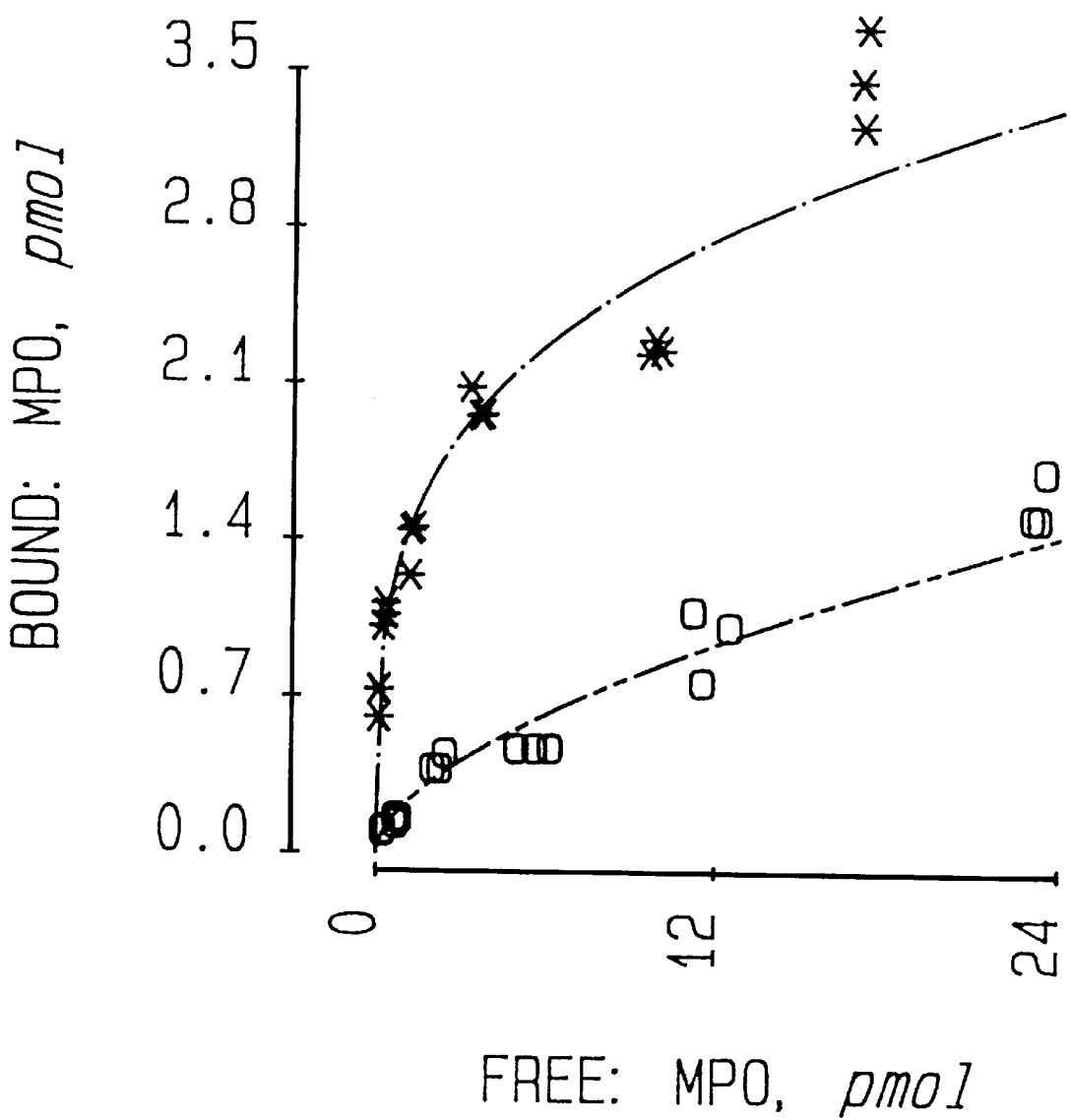
FIG. 7A is a plot of bound versus free MPO expressed in picomoles per reaction volume (1 ml) on separate incubation with the microbes *Staph. Aureus* (shown as "*" in FIG. 7) and *Streptococcus sp.* (viridans, shown as "o" in FIG. 7).

FIG. 7A plots the MPO bound to *Staph. aureus* and viridans streptococci versus free MPO using $7.5*10^8$ *Staph. aureus* and $2.4*10^8$ viridans streptococci per test respectively. The relationship of microbe-bound to free MPO is described as:

$$Free\ MPO_{pmol} = k*[Bound\ MPO_{pmol}]^p \quad (25)$$

At a free concentration of approximately 10 pmol MPO/ml, the quantity of MPO bound to $7.5*10^8$ *Staph. aureus* is limited to approximately 2 pmol, and the quantity of MPO bound per $2.4*10^8$ viridans streptococci is approximately 1 pmol.

The near-saturation MPO binding capacity of the microbe can be estimated by expressing the quantity of MPO bound in terms of molecules per microbe. For example, the molar quantity of MPO bound, i.e., $2*10^{-12}$ mol for *Staph. aureus*, is multiplied by Avagadro's number, i.e., $6*10^{23}$, and the product in molecules of MPO bound, is divided by the number of microbes, $7.5*10^8$, yielding the quotient, 2,400 molecules MPO bound per *Staph. aureus*.

Figure 7B:
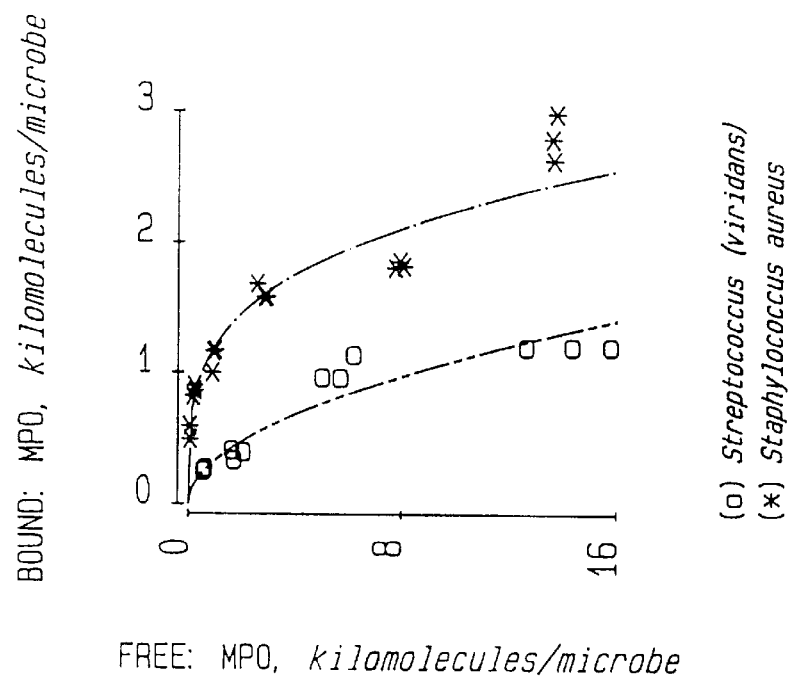
FIG. 7B is a plot of the data of FIG. 7A with MPO concentration expressed in kilomolecules ($^1O_3$ molecules) per microbe.

FIG. 7B plots the bound-versus-free MPO expressed as molecules per microbe.

Figure 7C:
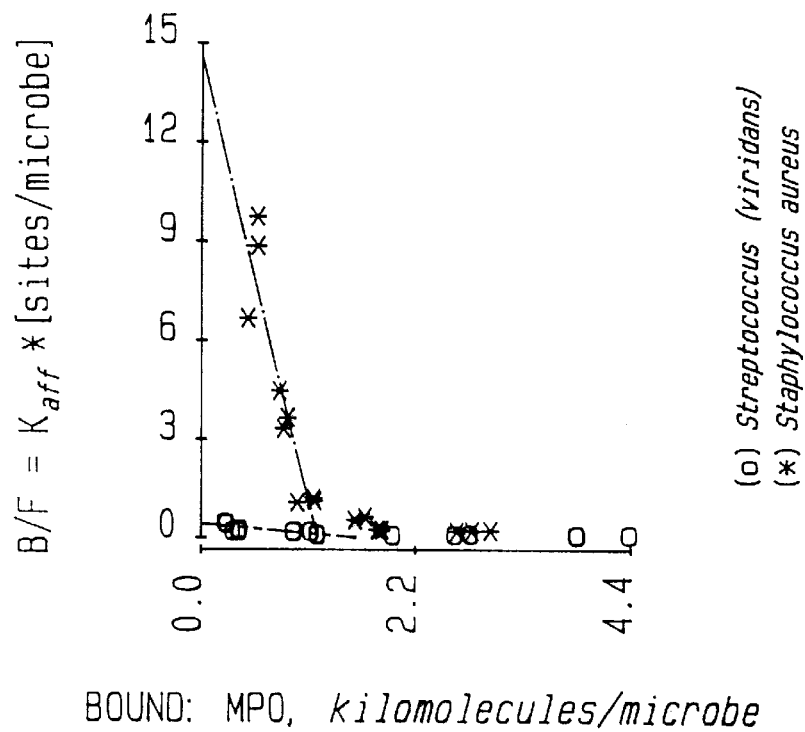
FIG. 7C is a Scatchard plot of the data of FIG. 7B, in which the ratio of bound to free MPO is plotted against the bound MPO expressed as kilomolecules per microbe in 1 ml reaction volume of a *Staph. aureus* suspension (shown as "*") or a *Streptococcus sp.* (viridans) suspension (shown as "o").

The Scatchard plots of these data are presented in FIG. 7C, wherein the Staph. aureus data points are marked as "*" and the viridans streptococcus are marked at "o". As previously developed in consideration of equations (19) through (21), there is a linear relationship between the ratio of Bound/Free MPO and the concentration of Bound MPO. The absolute value of the slope of this line is the value of the affinity constant, $K_{aff}$. In FIG. 7C, Bound MPO is expressed as the total binding sites per microbe per reaction volume, i.e., MPO Bound/microbe/ml. Thus the x-intercept approximates the number of MPO binding sites per microbe, and the y-intercept is the maximum extrapolated bound/free ratio, i.e., the product of $K_{aff}$ multiplied by the number of MPO binding sites per microbe.

Two relatively distinct linear relationship are demonstrated by the plot of the *Staph. aureus* data. In the 0 to 1,000 MPO molecules bound per microbe range the relationship is relatively linear, i.e., $r^2=0.83$, and can be described by the function:

$$MPO\text{-}Staph.\ aureus = -0.012128*[Sites] + 14.647 \quad (28)$$

Therefore, the $K_{aff}$ is $1.213*10^{-2}$, the $K_{aff}*$[Microbe Sites] is 14.647, and the total binding capacity is 1,208 MPO molecules per microbe. The *Staph. aureus* plot also indicates the presence of a second class of binding sites with relatively low affinity. In the 1,000 to 3,000 MPO molecules bound per microbe range, this low affinity binding is defined by the function:

$$MPO\text{-}Staph.\ aureus = -0.000491*[Sites] + 1.433 \quad (29)$$

with an $r^2=0.65$. Note that the $K_{aff}$, $4.907*10^{-4}$, for this second class of binder is twenty-fivefold lower than that calculated for the high affinity binding sites, but that the number of MPO binding sites per microbe is higher, approximately 2,900/microbe.

Although less obvious from the plot, the viridans streptococcus data also indicate the presence of at least two different types of binding. In the 0 to 1,500 MPO molecules bound per microbe range, the relationship is roughly linear, i.e., $r^2 = 0.66$, as defined by the equation:

$$MPO\text{-}Strep.(viridans) = -0.000255*[Sites] + 0.406 \quad (30)$$

Note that this $K_{aff}$, $2.551*10^{-4}$, is magnitudinally lower than the "high affinity" binding sites of *Staph. aureus*. Approximately 1,600 of these low affinity MPO binding sites are present per viridans streptococcus. As previously deduced from the raw plot of the data, MPO binding capacities for the two microbes are comparable with respect to the total number of binding sites per microbe. Note that the plots are quite similar about 2,000 molecules per microbe. The values for B/F, $K_{aff}$, and sites/microbe calculated by Scatchard analysis are set forth in the following Table 10. In like manner several gram-negative and gram-positive bacteria, fungal yeasts, and human erythrocytes were tested for MPO binding capacity. The results these Scatchard analyses are also presented in Table 10.

TABLE 10

Myeloperoxidase:Microbe Binding Statistics Derived by the Scatchard Method:
$$B/F = K_{aff}*[\text{Microbe Sites}]$$

| Cell Type | Range | B/F | $K_{aff}$ ($*10^6$) | Sites/Microbe | $r^2$ |
|---|---|---|---|---|---|
| Gram Negative Bacteria: | | | | | |
| P. aeruginosa | 0 ... 100 | 1.141 | 16,568 | 69 | 0.73 |
| | 8,000 ... 18,000 | 49.458 | 2,703 | 18,469 | 0.92 |
| S. typhimurium | 1,000 ... 8,800 | 4.161 | 510 | 8,156 | 0.98 |
| E. coli | 0 ... 250 | 0.383 | 1,511 | 253 | 0.73 |
| | 10,000 ... 23,000 | 2.765 | 83 | 33,305 | 0.68 |
| Gram Positive Bacteria: | | | | | |
| Staph. aureus | 400 ... 1,200 | 14.646 | 12,124 | 1,208 | 0.83 |
| Lactic Acid Bacteria (LAB): | | | | | |
| Lact. (Doderleins) | 400 ... 2,500 | 1.805 | 329 | 5,488 | 0.68 |
| Strep. viridans | 200 ... 1,200 | 0.406 | 255 | 1,591 | 0.66 |
| St. pyogenes (A) | 700 ... 1,200 | 1.775 | 1,370 | 1,295 | 0.77 |
| St. agalactiae (B) | 500 ... 2,000 | 0.732 | 325 | 2,253 | 0.93 |
| St. faecalis (D) | 1,000 ... 6,000 | 6.373 | 1,053 | 6,055 | 0.95 |
| Yeast (Eukaryote, Fungus): | | | | | |
| Cand. albicans | 2,400 ... 7,000 | 0.657 | 57 | 11,480 | 0.91 |
| Cryp. neoformans | 700 ... 14,000 | 0.256 | 15 | 17,141 | 0.86 |
| Erythrocyte (Eukaryote, Human): | | | | | |
| Red Blood Cell (Human RBC) | 0 ... 30,000 | <0.2 | | | <0.1 |

The MPO content of the supernatant and pellet was determined by luminometry using simultaneously run MPO standards.
Range is expressed as the ratio of MPO molecules per cell.
Approximately $10^8$ to $10^9$ cells were tested per MPO concentration.
B/F is the ratio of bound to free MPO; i.e., B is the number of MPO molecules bound per cell, and F is the number of MPO molecules free.
$K_{aff}$ is the affinity or association constant, and sites/microbe is the number of MPO binding sites per cell.

As can be seen from the results shown in Table 10:

(1) MPO binds to all of the pathogenic bacteria tested.

(2) Those lactic acid bacteria that are the major components of the normal flora, i.e., *Streptococcus sp.* (viridans) in the mouth and oropharynx, and *Lactobacillus sp.* (Doderlein's bacillus) of the vagina, have the lowest $K_{aff}$ values of the bacteria tested.

(3) Relative to bacteria, yeast have lower $K_{aff}$ values, but in keeping with their larger sizes, yeast have more binding sites per microbe.

(4) Essentially no binding of MPO to human erythrocytes was detected, i.e., B/F of less than 0.2 with an $r^2$ less than 0.1.

As such, the proximity requirement for XPO catalyzed microbe killing is satisfied for MPO. MPO demonstrates a high affinity for gram-negative and gram-positive pathogenic microbes, and a relatively low affinity for $H_2O_2$-producing members of the normal flora, i.e., viridans streptococci and Doderlein's lactobacillus. In an environment containing pathogens and normal flora, limiting the MPO availability effectively limits MPO binding to pathogens. Thus, microbicidal action can be selectively limited to the pathogenic microbes present, and the viability of the normal flora can be preserved. In the presence of competing pathogens, MPO would act synergistically with the LAB flora by selective binding to and killing of the pathogenic microbes.

Example 7

Scatchard Analysis of Chloroperoxidase Binding to Microbes

Materials: The bacteria, yeasts, and erythrocytes were prepared as described in Example 6. Fungal chloroperoxidase (CPO) was purchased from Sigma Chemical Company. Chloroperoxidase was Initially quantified by reduced minus oxidized (R–O) difference spectroscopy using dithionite as the reductant. The 400 nm to 280 nm absorbance ($A_{400/280}$) ratio for CPO was 0.8. An R–O difference extinction coefficient of 56 $mM^{-1}$ $cm^{-1}$ at 450 nm was used for CPO quantification. Luminol-dependent luminescence assays of CPO oxygenation activity were also taken with each microbe binding assay.

Methodology: The protocol was the same as described for Example 6, except that CPO was employed as the XPO.

Standard measurements of CPO versus CL were taken with each binding study, and these data were used for converting the chemiluminescent data to molecules CPO. The methodology was as described for MPO standardization measurements of FIG. 6.

Figure 8A:
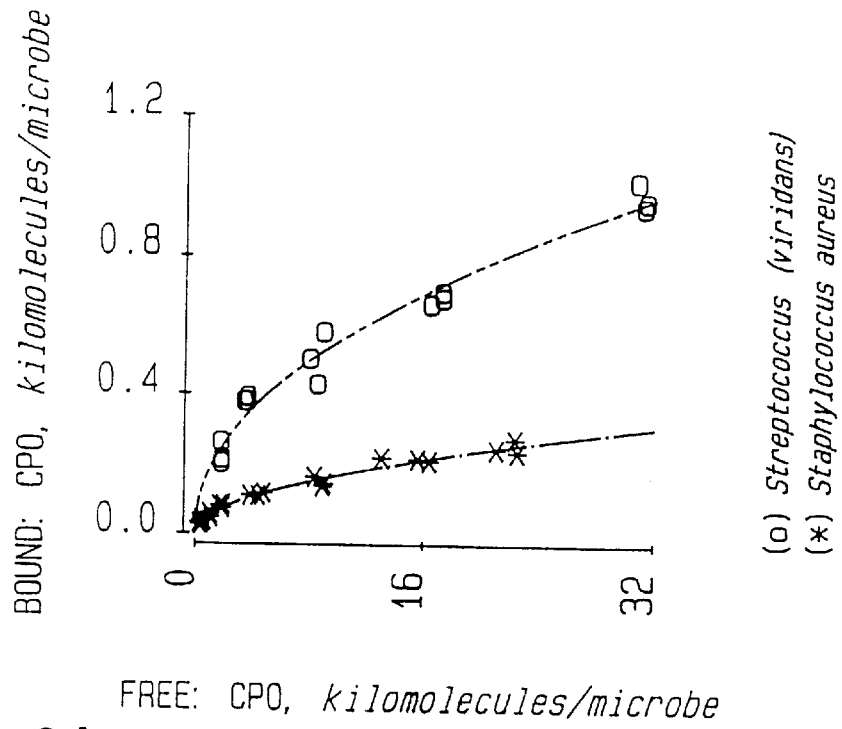
FIG. 8A is a plot of bound versus free CPO expressed in kilomolecules ($^1O_3$ molecules) per microbe.

FIG. 8A presents the molecules of CPO bound per *Staph. aureus* and *Streptococcus sp.* (viridans) plotted against the unbound molecules of CPO per microbe per reaction volume. In contrast with the MPO binding data of FIG. 7B, *Streptococcus sp.* (viridans) bind CPO more strongly than *Staph. aureus*. However, neither microbe binds CPO as effectively as MPO.

Figure 8B:
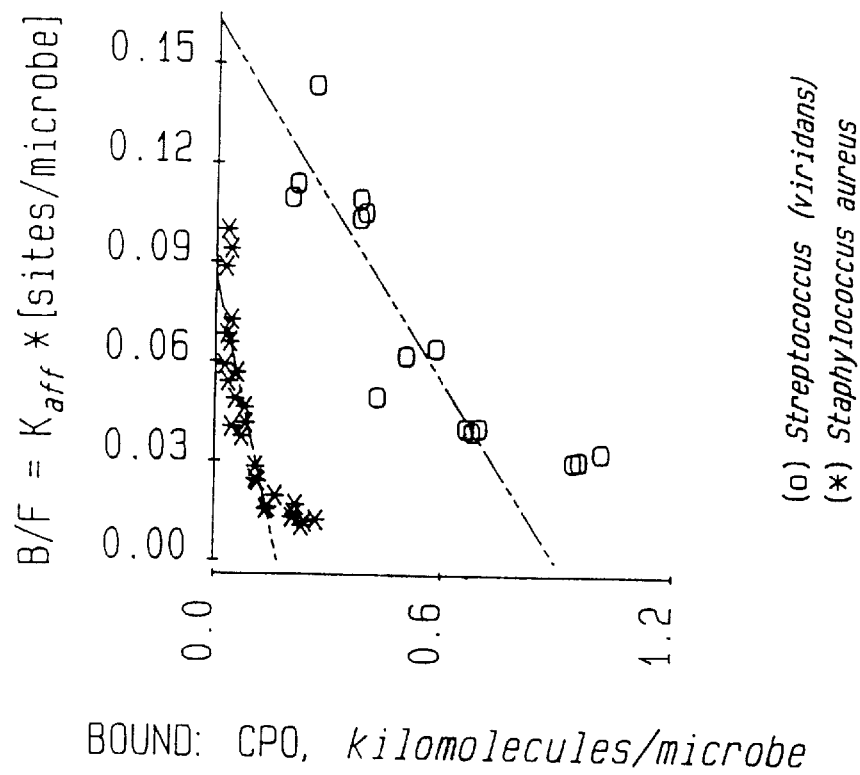
FIG. 8B is a Scatchard plot of the data of FIG. 8A, in which the ratio of bound to free CPO is plotted against the bound CPO expressed as kilomolecules per microbe in 1 ml reaction volume of a *Staph. aureus* suspension (shown as "*") or a *Streptococcus sp.* (viridans) suspension (shown as "o").

The Scatchard plot of these data is presented In FIG. 8B. Over a similar range of binding, the magnitude of the ordinate, i.e., $B/F=K_{aff}\cdot[\text{sites/microbe}]$, is a hundredfold lower than that described for the MPO Scatchard plot of FIG. 7C. CPO binding capacity of *Streptococcus sp.* (viridans) is relatively greater than that of *Staph. aureus*, but the CPO binding capacities of both microbes are low relative to MPO binding capacity.

In a manner analogous to that described for MPO, the same range of bacteria, yeast, as well as erythrocytes, were analyzed for CPO-binding capacity by the Scatchard method. The tabulated results are shown in Table 11:

TABLE 11

Chloroperoxidase:Microbe Binding Statistics Derived by the Scatchard Method:
B/F = $K_{aff}$*[Microbe Sites]

| Cell Type | Range | B/F | $K_{aff}$ (*$10^6$) | Sites/ Microbe | $r^2$ |
|---|---|---|---|---|---|
| Gram Negative Bacteria: | | | | | |
| P. aeruginosa | 20 ... 500 | 0.030 | 34 | 882 | 0.52 |
| S. typhimurium | 0 ... 200 | 0.130 | 683 | 191 | 0.65 |
| E. coli | 0 ... 150 | 0.310 | 381 | 162 | 0.72 |
| Gram Positive Bacteria: | | | | | |
| Staph. aureus | 0 ... 175 | 0.087 | 501 | 173 | 0.72 |
| Lactic Acid Bacteria (LAB): | | | | | |
| Lact. (Doderleins) | 40 ... 350 | 0.146 | 428 | 340 | 0.64 |
| Strep. (viridans) | 200 ... 700 | 0.163 | 182 | 898 | 0.78 |
| St. pyogenes (A) | 300 ... 1,500 | 0.321 | 344 | 932 | 0.70 |
| St. agalactiae (B) | 120 ... 600 | 0.085 | 139 | 614 | 0.68 |
| St. faecalis (D) | 150 ... 1,500 | 0.051 | 19 | 2,610 | 0.52 |
| Yeast (Eukaryote, Fungus): | | | | | |
| Cand. albicans | 1,600 ... 7,000 | 0.178 | 29 | 6,133 | 0.64 |
| Cryp. neoformans | 400 ... 6,500 | 0.039 | 4 | 9,010 | 0.10 |
| Erythrocyte (Eukaryote, Human): | | | | | |
| Red Blood Cell (Human RBC) | 0 ... 60,000 | <0.2 | | | <0.1 |

The CPO content of the supernatant and pellet was determined by luminometry using simultaneously run CPO standards. The conditions were as described in the legend of Table 10.

Example 8

Scatchard Analysis of Eosinophil Peroxidase and Lactoperoxidase Binding to Microbes Materials: The bacteria, yeasts, and erythrocytes were prepared as described in Example 6. Eosinophil peroxidase (EPO) was extracted and purified from porcine leukocytes as described in Example 2. Lactoperoxidase (LPO) was purchased from Sigma Chemical Co. EPO and LPO were quantified by reduced minus oxidized (R–O) difference spectroscopy using dithionite as the reductant. The 412 nm to 280 nm absorbance ($A_{412/280}$) ratio for EPO was 0.7 and the 412 nm to 280 nm absorbance ($A_{412/280}$) ratio for LPO was 0.7. An R–O difference extinction coefficient of 56 $nm^{-1}$ $cm^{-1}$ at 450 nm was used for EPO quantification, and an R–O difference extinction coefficient of 56 $mM^{-1}$ $cm^{-1}$ at 438 nm was used for LPO quantification. Luminol-dependent luminescence assays of EPO and LPO oxygenation activities were also taken with each microbe binding assay.

Methodology: The protocol was the same as described for Example 6 except that EPO and LPO were employed as the XPOs.

Figure 9A:
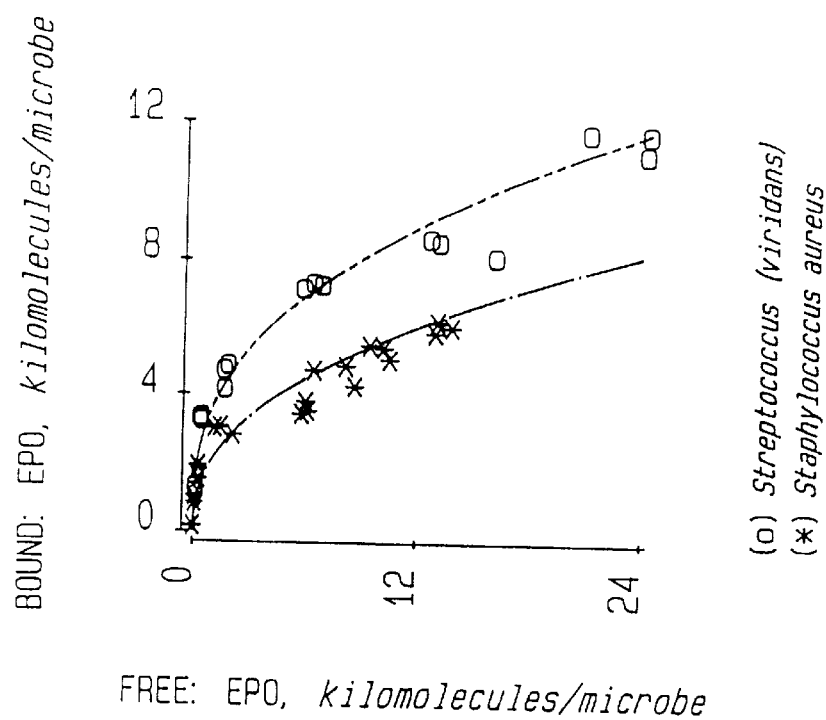
FIG. 9A is a plot of bound versus free EPO expressed in kilomolecules ($^1O_3$ molecules) per microbe.

Perusal of the MPO and EPO binding data emphasizes the differences that can distinguish haloperoxidases with regard to their microbe binding capacities. For consistency in intercomparison of the binding data, FIG. 9A presents the molecules of EPO bound per Staphylococcus aureus and Streptococcus sp. (viridans) plotted against the unbound molecules of EPO per microbe per reaction volume. EPO binding to Streptococcus sp. (viridans) and Staph. aureus are similar in the low range of EPO concentration, but there appear to be fewer binding sites per Staph. aureus. Note that within the range of concentration tested EPO is more effectively bound to either microbe that previously observed with MPO.

Figure 9B:
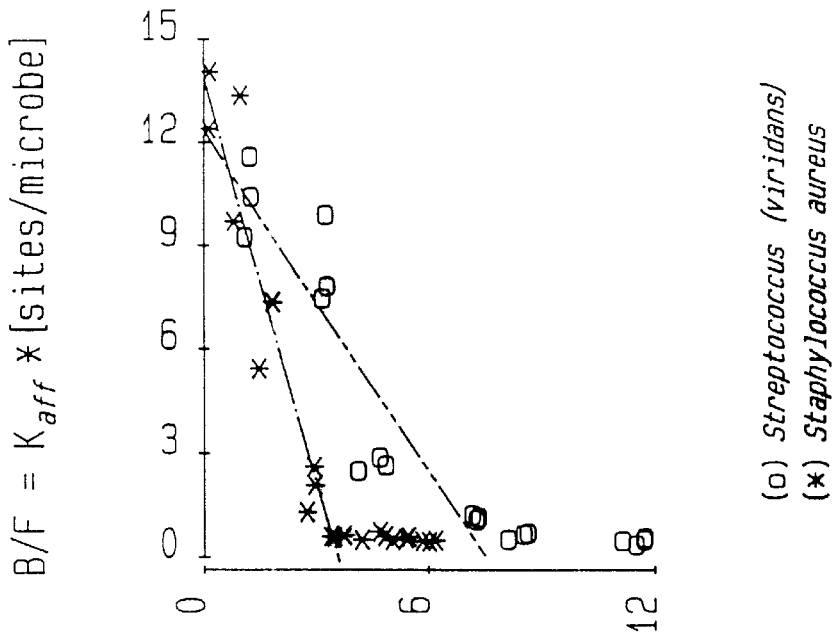
FIG. 9B is a Scatchard plot of the data of FIG. 9A, in which the ratio of bound to free EPO is plotted against the bound EPO expressed as kilomolecules per microbe in 1 ml reaction volume of a *Staph. aureus* suspension (shown as "*") or a *Streptococcus sp.* (viridans) suspension (shown as "o").

The Scatchard plot of these data is presented in FIG. 9B. Over a similar range of binding, the magnitude of the ordinate, i.e., B/F=$K_{aff}$*[sites/microbe], is the same as that described for the MPO Scatchard plot of FIG. 7C. EPO binding capacity for Streptococcus sp. (viridans) is relatively greater than MPO binding capacity. However, the binding capacity for Staph. aureus is similar to MPO. Overall, EPO binding capacity more closely resembles MPO than CPO.

As previously described for MPO and CPO, the same range of bacteria, yeast, and erythrocytes were analyzed for EPO-binding capacity by the Scatchard method. The tabulated results are present in Table 12.

TABLE 12

Eosinophil Peroxidase (EPO):Microbe Binding Statistics Derived by the Scatchard Method:
B/F = $K_{aff}$*[Microbe Sites]

| Cell Type | Range | B/F | $K_{aff}$ (*$10^6$) | Sites/ Microbe | $r^2$ |
|---|---|---|---|---|---|
| Gram Negative Bacteria: | | | | | |
| P. aeruginosa | 50 ... 300 | 0.964 | 2,771 | 348 | 0.72 |
|  | 8,500 ... 10,000 | 9.151 | 830 | 11,030 | 0.59 |
| S. typhimurium | 1,000 ... 17,100 | 11.982 | 651 | 18,394 | 0.94 |
| E. coli | 0 ... 160 | 3.444 | 22,280 | 155 | 0.72 |
|  | 100 ... 300 | 0.735 | 2,108 | 349 | 0.65 |
| Gram Positive Bacteria: | | | | | |
| Staph. aureus | 130 ... 4,000 | 13.910 | 3,829 | 3,633 | 0.92 |
| Lactic Acid Bacteria (LAB): | | | | | |
| Lact. (Doderleins) | 0 ... 50 | 1.368 | 92,089 | 15 | 0.69 |
| Strep. (viridans) | 1000 ... 7,500 | 12.349 | 1,641 | 7,526 | 0.84 |
| St. pyogenes (A) | 200 ... 2,000 | 32.750 | 12,713 | 2,576 | 0.82 |
| St. agalactiae (B) | 3,000 ... 6,000 | 8.658 | 1,417 | 6,109 | 0.93 |
| St. faecalis (D) | 0 ... 34 | 0.329 | 13,986 | 24 | 0.59 |
| Yeast (Eukaryote, Fungus): | | | | | |
| Cand. albicans | 5,000 ... 13,000 | 7.066 | 512 | 13,806 | 0.83 |
| Cryp. neoformans | 20,000 ... 60,000 | 19.123 | 329 | 58,059 | 0.95 |
| Erythrocyte (Eukaryote, Human): | | | | | |
| Red Blood Cell (Human RBC) | 0 ... 60,000 | <0.2 | | | <0.1 |

The EPO content of the supernatant and pellet was determined by luminometry using simultaneously run EPO standards. The conditions were as described in the legend of Table 10.

Comparison of the data of Table 10 and Table 12 data illustrates that EPO-binding capacities differ from MPO-binding capacities with respect to individual microbes, e.g., *Streptococcus sp.* (viridans), but that both haloperoxidases possess magnitudinally similar binding capacities with respect to the bacteria tested in general. Of potential significance is the magnitudinally greater binding capacity of EPO for the fungi tested, i.e., *Candida albicans* and *Cryptococcus neoformans*.

Figure 10A:
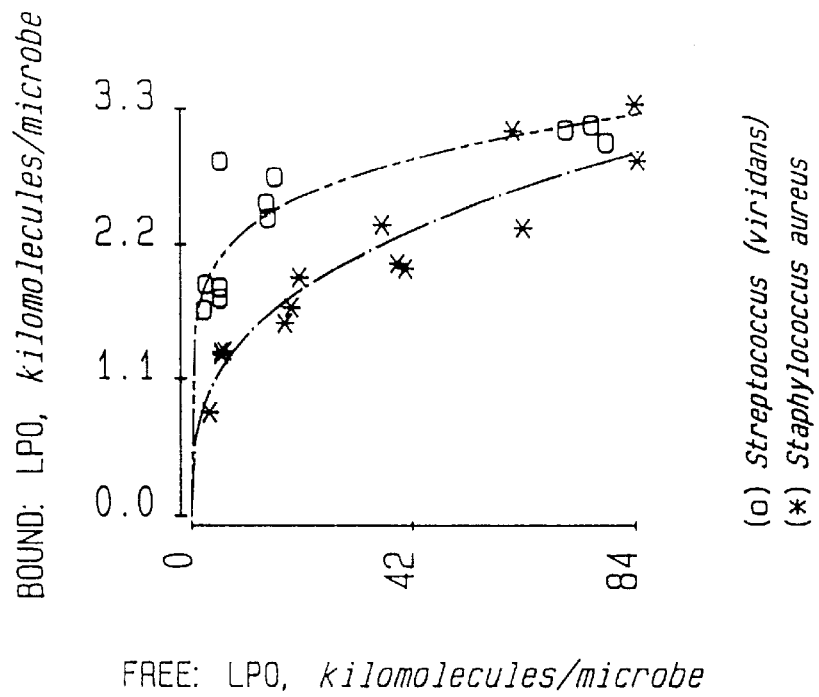
FIG. 10A is a plot of bound versus free LPO expressed in kilomolecules ($^1O_3$ molecules) per microbe.

FIG. 10A presents the molecules of LPO bound per *Staph. aureus* and *Streptococcus sp.* (viridans) plotted against the unbound molecules of LPO per microbe per reaction volume. The binding capacities of LPO for *Streptococcus sp.* (viridans) and *Staph. aureus* are less than observed for EPO and MPO, but much higher than observed for CPO.

Figure 10B:
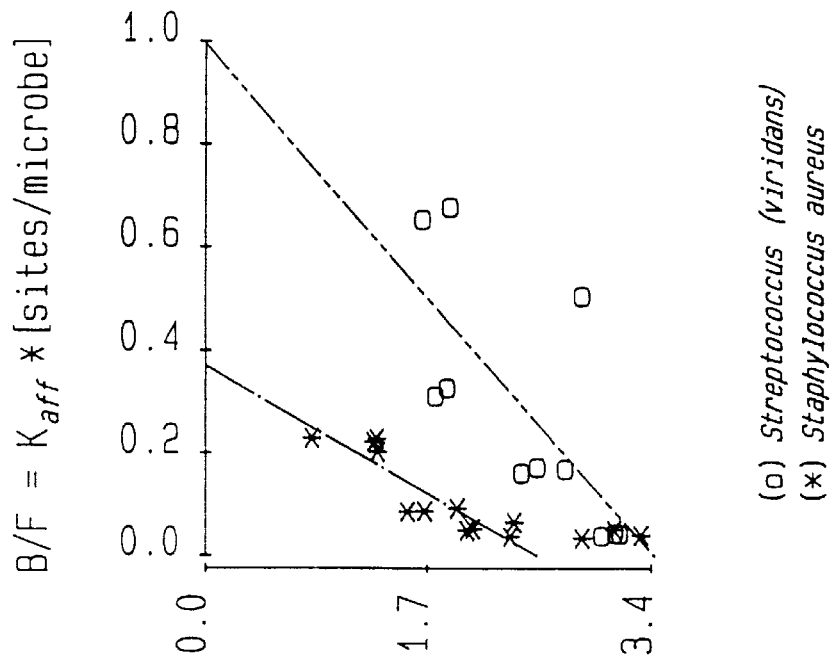
FIG. 10B is a Scatchard plot of the data of FIG. 10A, in which the ratio of bound to free LPO is plotted against the bound LPO expressed as kilomolecules per microbe in 1 ml reaction volume of a *Staph. aureus* suspension (shown as "*") or a *Streptococcus sp.* (viridans) suspension (shown as "o").

The Scatchard plot of these data is presented in FIG. 10B. The EPO binding capacities for viridans streptococcus and *Staph. aureus* are similar and relatively low in comparison with MPO and EPO. A survey of LPO-microbe binding capacities was conducted using the same range of bacteria, yeast, and erythrocytes previously employed for haloperoxidase binding analysis. The tabulated results are presented in Table 13.

TABLE 13

Lactoperoxidase:Microbe Binding Statistics Derived by the Scatchard Method:
B/F = $K_{aff}$*[Microbe Sites]

| Cell Type | Range | B/F | $K_{aff}$ (*$10^6$) | Sites/ Microbe | $r^2$ |
|---|---|---|---|---|---|
| Gram Negative Bacteria: | | | | | |
| P. aeruginosa | 1,100 ... 2,300 | 0.748 | 309 | 2,423 | 0.82 |
| S. typhimurium | 900 ... 4,000 | 0.610 | 176 | 3,462 | 0.92 |
| E. coli | 2,000 ... 5,100 | 1.053 | 201 | 5,232 | 0.75 |
| Gram Positive Bacteria: | | | | | |
| Staph. aureus | 800 ... 2,300 | 0.392 | 162 | 2,417 | 0.82 |
| Lactic Acid Bacteria (LAB): | | | | | |
| Lact. (Doderleins) | 600 ... 3,000 | 0.415 | 110 | 3,784 | 0.79 |
| St. viridans | 1,500 ... 3,200 | 0.599 | 155 | 3,877 | 0.26 |
| St. pyogenes (A) | 4,000 ... 24,000 | 0.511 | 22 | 22,793 | 0.84 |
| St. agalactiae (B) | 1,000 ... 8,000 | 0.713 | 104 | 6,884 | 0.69 |
| St. faecalis (D) | 1,250 ... 6,000 | 0.219 | 25 | 8,762 | 0.63 |

TABLE 13-continued

Lactoperoxidase:Microbe Binding Statistics Derived by the Scatchard Method:
B/F = $K_{aff}$*[Microbe Sites]

| Cell Type | Range | B/F | $K_{aff}$ (*$10^6$) | Sites/ Microbe | $r^2$ |
|---|---|---|---|---|---|
| Yeast (Eukaryote, Fungus): | | | | | |
| Cand. albicans | 7,000 ... 16,000 | 1.213 | 76 | 16,002 | 0.79 |
| Cryp. neoformans | 110,000 ... 300,500 | 0.684 | 2 | 302,664 | 0.86 |
| Erythrocyte (Eukaryote, Human): | | | | | |
| Red Blood Cell (Human RBC) | 0 ... 500,000 | <0.2 | | | <0.1 |

The LPO content of the supernatant and pellet was determined by luminometry using simultaneously run LPO standards. The conditions were as described in the legend of Table 10.

Intercomparison of the data of Tables 10, 11, 12, and 13 illustrates that the binding capacities of LPO are generally less than those of MPO and EPO, but greater than CPO. As previously noted for MPO and EPO, LPO tends to show a relatively greater binding capacity for gram-negative bacteria and yeasts.

Example 9

Lactic Acid Bacteria:Haloperoxidase Synergistic Action

The normal flora of man includes several members of the lactic acid family of bacteria. Likewise, several other members of this family are employed in the fermentation industry, e.g., cheese production. These gram-positive bacteria are characterized by an inability to synthesize protoporphin. Consequent to their lack of respiratory cytochromes, redox metabolism is catalyzed by flavoenzymes yielding lactic acid and in many cases $H_2O_2$ as metabolic products.

Many of these lactic acid bacteria (LAB) are obligately indigenous to man and related animals. Members of the viridans group of streptococci, i.e., Streptococcus mitis, salivarious, et cetera, are indigenous to the mouth, oropharyngeal, and to a lesser extent, nasopharyngeal portions of the upper respiratory tract. The viridans streptococci are also commonly found in the vagina and in feces. The lactobacilli members of the LAB are also commonly found in the mouth. Other members of this group, i.e., Tissier's bacillus (Lactobacillus bifidus) and Doderlein's lactobacillus, are indigenous to the feces of breast fed infants and to the vagina during the reproductive years.

"Wherever in nature two or more species of microorganisms (or, for that matter, macroorganisms) grow in intimate association, each will interact with the others; and if the microorganisms grow upon a host organism, then the host will be in some way influenced by the interaction: 'mere toleration is biologically and statistically improbable' (Lucas, 1949)" (Rosebury, 1962, Microorganisms Indigenous To Man, McGraw-Hill, New York). It is not unexpected that members of the LAB serve to protect the host by competition with pathogenic microbes. "The interaction of man's indigenous microflora and exogenously acquired pathogens has been the subject of sporadic investigation and continuous speculation for more than 5 decades. However, only recently has it been demonstrated conclusively that antagonistic interactions may enhance man's capacity to resist infection" (Sanders, 1969, J.Infect.Dis. 129: 698–707). The validity of this position is illustrated by the phenomenon of superinfection following the administration of antibiotics (Weinstein, 1947, Amer.J.Med.Sci. 214: 56–63; McCurdy and Neter, 1952, Pediatrics 9: 572–576).

The in vitro ability of pneumococcus and viridans streptococcus to kill meningococcus and other gram-negative bacteria was first reported by Colebrook in 1915 (Lancet, Nov. 20 1915, 1136–1138). His technique was to place a drop of streptococci (pneumococcal) culture and let it trickle across an agar plate; after the track of this stream had dried, he repeated the process by running a drop of gram-negative culture in a direction perpendicular to the original streptococci. He observed inhibition of the gram-negative culture where the two streams crossed. Furthermore, he noted that the extent of killing was proportional to the time interval separating the plating of the two cultures. "By allowing the growth of pneumococcus to get well started before the meningococcus stream was planted the growth of the latter was totally checked, not only where the two streams met, but also to a distance of nearly a centimeter on either side of that point." Colebrook also found that greatly increasing the concentration of the gram-negative bacterial suspension resulted in a vigorous growth of the microbe. "Clearly, then, the pneumococci had not deprived the medium of something which was essential for the growth of meningococcus, nor in any other way had they rendered the medium, as such unsuitable for that organism" (Colebrook, 1915). The generation of acid and $H_2O_2$ by viridans streptococcus was demonstrated by M'Leod and Gordon in 1922 (Biochem.J. 16: 499). It is probable that the time interval required for streptococcus inhibition of meningococcus is related to the accumulation of streptococcal-generated $H_2O_2$.

The in vivo importance of streptococci in suppressing the growth of potential pathogens is also implied by the phenomenon of superinfection following antibiotic therapy. "Members of the viridans group of streptococci, the predominant strains of the oropharyngeal flora in most individuals, can inhibit the growth of enteric gram-negative bacilli, the organisms that commonly overgrow at this site following therapy with massive doses of penicillin. It was proposed that suppression (or elimination) of these streptococci by massive doses of antibiotics suppresses (or eliminates) their inhibitory action and permits multiplication of the previously inhibited (or newly introduced) bacilli" (Sprunt et al., 1971, J.Infect.Dis. 123: 1–10).

As demonstrated by the data of Table 10, XPO binding is microbe specific. Furthermore, binding affinity is relatively poor for the normal flora members of the lactic acid family of bacteria. Selectivity of binding, combined with the lifetime restrictions of $^1O_2$ reactivity, provide $H_2O_2$-producing LAB with a mechanism for surviving the presence of low concentrations of MPO. Furthermore, such conditions actually favor the supremacy of indigenous LAB in antagonistic microbial competitions. Introduction of MPO into a mixed bacterial environment, e.g., *Staph. aureus* and *Streptococcus sp.* (viridans), will result in selective binding of MPO to *Staph. aureus*. Consequently $H_2O_2$, the metabolic product of *Streptococcus sp.* (viridans), serves as substrate for the *Staph. aureus*-bound MPO yielding microbial reactants, e.g., HOCl and especially $^1O_2$, with potent reactivity but limited reactive lifetime. As described in Example 6, such MPO-catalyzed microbicidal action should be relatively selective for *Staph. aureus*.

The synergistic effect of viridans streptococci on the MPO-dependent killing of *Staphylococcus aureus, Escherichia coli, Pseudomonas aeruginosa* and *Candida albicans* in the absence and presence of erythrocytes is shown as follows.

Materials: The bacteria, yeast and RBCs were prepared and quantified as described in Example 1. MPO was prepared and quantified as described in Example 2.

Methods: 100 μl of target microbe suspension (approximately $10^6$ microbes), 100 μl of *Streptococcus sp.* (viridans) suspension (approximately $5*10^7$ streptococci), 100 μl of MPO (concentration varied), 100 μl of glucose (1 mg), 500 μl of NS, and where indicated, either 100 μl of erythrocyte suspension ($10^7$ RBCs) or NS were added to each tube for a 1 ml final volume. The contents were gently mixed, and the tubes were incubated for 30 minutes at 23° C. Microbial killing was measured by agar plate dilution as previously described in Example 1 except that the colonies were allowed to grow for 2–3 days in order to fully develop the smaller colonies of streptococci.

(1) Killing of *Staph. aureus* in the Absence of Erythrocytes. The data of Table 14 demonstrate the effect of MPO on streptococci-dependent killing of *Staph. aureus*.

TABLE 14

Myeloperoxidase-Dependent Viridans Streptococcal Microbicidal Action in the Absence and Presence of Erythrocytes:

| Organism | MPO, pmol | No RBC CFU: | RBC ($10^7$) CFU: | Hemoglobin: Pellet | Super. |
|---|---|---|---|---|---|
| P. aeruginosa | None | 3,500,000 | 3,400,000 | 1.0 | 0.0 |
|  | 100.0 | 0 | 0 | 1.0 | 0.1 |
|  | 33.3 | 0 | 10,000 | 0.9 | 0.0 |
|  | 11.1 | 0 | 7,200 | 0.9 | 0.0 |
|  | 3.7 | 0 | 6,200 | 1.0 | 0.0 |
|  | 1.2 | 0 | 520,000 | 1.0 | 0.1 |
|  | 0.4 | 10,000 | 4,500,000 | 1.0 | 0.0 |
|  | 0.13 | 2,200,000 | 3,900,000 | 0.7 | 0.0 |
| E. coli | None | 2,000,000 | 2,600,000 | 1.0 | 0.0 |
|  | 100.0 | 0 | 0 | 1.0 | 0.0 |
|  | 33.3 | 0 | 0 | 1.0 | 0.0 |
|  | 11.1 | a | 10,000 | 1.0 | 0.0 |
|  | 3.7 | 10,000 | 930,000 | 1.1 | 0.0 |
|  | 1.2 | 650,000 | 2,600,000 | 1.0 | 0.0 |
|  | 0.4 | 1,900,000 | 2,500,000 | 1.0 | 0.0 |
| Staph. aureus | None | 1,600,000 | 1,800,000 | 1.0 | 0.0 |
|  | 100.0 | 0 | 8,000 | 0.9 | 0.0 |
|  | 33.3 | 0 | 740,000 | 1.0 | 0.0 |
|  | 11.1 | 820,000 | 930,000 | 1.0 | 0.0 |
|  | 3.7 | 430,000 | 1,900,000 | 1.0 | 0.0 |
|  | 1.2 | 1,600,000 | 1,700,000 | 1.0 | 0.1 |
|  | 0.4 | 1,700,000 | 1,900,000 | 1.0 | 0.0 |
| Cand. albicans | None | 200,000 | 240,000 | 1.0 | 0.0 |
|  | 100.0 | 0 | 4,000 | 0.8 | 0.0 |
|  | 33.3 | 0 | 250,000 | 0.9 | 0.0 |
|  | 11.1 | 0 | 180,000 | 1.0 | 0.0 |
|  | 3.7 | 0 | 240,000 | 1.0 | 0.0 |
|  | 1.2 | 6,000 | 250,000 | 1.0 | 0.0 |
|  | 0.4 | 160,000 | 210,000 | 1.0 | 0.0 |
|  | 0.13 | 110,000 | 260,000 | 1.0 | 0.0 |

Streptococci do not inhibit *Staph. aureus* in the absence of MPO. Addition of 3.7 pmol MPO during the 30 minute interval decreased the *Staph. aureus* count by 73% without any effect on the streptococci and addition of 33 pmol MPO produced a total kill of *Staph. aureus* without streptococci killing. Addition of 100 pmol MPO produced total kill of *Staph. aureus* and decreased the streptococci count by over an order of magnitude.

The data of Table 10 indicate that the MPO-binding capacity of *Staph. aureus* is more than thirtyfold that of streptococci. The data of Table 14 demonstrate that greater than 50% of the $10^6$ *Staph. aureus* are killed with $2*10^{12}$ molecules of MPO, and $2*10^{13}$ molecules MPO effect 100% kill of $10^6$ *Staph. aureus* with relative sparing of viridans streptococcus. This range of MPO is equivalent to a total of approximately $10^6$ to $10^7$ molecules MPO/*Staph. aureus* and $10^4$ to $10^5$ molecules MPO/streptococcus. Based on the high MPO binding capacity, i.e., B/F=14.6, of *Staph. aureus*, a very large portion of the available MPO will be bound to *Staph. aureus*. Furthermore, the low binding capacity, i.e., B/F=0.4, of Streptococcus sp. (viridans) ensures that only a small portion of the residual MPO will bind to the streptococci. At 100 pmol MPO, a concentration is magnitudinally higher than that required for *Staph. aureus* killing, streptococci was incomplete. Concentrations of MPO that effect complete killing of *Staph. aureus* inflict minimal damage on *Streptococci sp.* (viridans). As such, introduction of MPO would favor the supremacy of *Streptococci sp.* (viridans) over *Staph. aureus* and other high capacity MPO-binding microbes in antagonistic microbial competitions.

(2) Killing of *Staph. aureus* in the Presence of Erythrocytes. Table 14 further documents the effect $10^7$ RBCs on *Streptococcus sps.* (viridans)-dependent killing of *Staph. aureus* in the presence of the various concentrations of MPO tested. No killing was observed with 3.7 pmol MPO, but 33.3 pmol MPO decreased the *Staph. aureus* count by more than 50%. Inclusion of 100 pmol MPO decreased the *Staph. aureus* count by 95%, i.e., to $8*10^4$ CFU. This concentration of MPO also decreased but did not eliminate streptococci.

Bystander or collateral damage to the RBCs was assessed by measuring the extent of hemolysis, i.e., the supernatant/pellet hemoglobin ratio, and hemoglobin destruction i.e., final/initial hemoglobin ratio. Inclusion of $10^7$ RBCs in the reaction system produces a small, approximate threefold, inhibition of *Staph. aureus* killing. The added RBCs also inhibit *Streptococci sp.* (viridans) killing associated with relatively high MPO concentrations. Erythrocytes contain catalase, and the inhibition of both *Staph. aureus* and *Streptococci sp.* (viridans) killing most probably results from competitive consumption of $H_2O_2$ by RBC catalase. As presented in Table 10, erythrocytes have essentially NO binding capacity for MPO. This is consistent with the observed absence of hemolysis in combination with potent *Staph. aureus* killing. The microbicidal action of the streptococcal-MPO system does not cause bystander RBC damage, and as such, RBCs do not serve as competitive substrates. These observations are in stark contrast to those presented in Example 1 where hemolysis was observed with $H_2O_2$ and HOCl concentrations far below those required for microbicidal action.

Erythrocyte inhibition of the streptococcal-MPO system is very small relative to that observed for direct (MPO-independent) $H_2O_2$ and HOCl killing. The data of Tables 4 and 5 indicate that the equivalent quantity of RBCs caused an approximate thousandfold inhibition in both $H_2O_2$-dependent and HOCl-dependent killing of Staph. aureus.

Selective Staph. aureus killing in the presence of RBC without hemolysis strongly supports the concept of reactive proximity with respect to the selective antiseptic action of MPO; i.e., selective binding of MPO to the target microbe maximizes target damage and minimizes damage to $H_2O_2$-generating normal flora and host cells. The selective microbicidal action of MPO provides the basis for a physiologically sound approach to antisepsis. As previously described by Dakin, Fleming and others, host cells are more susceptible than microbes to the damaging actions of chemical antiseptics. The present invention Is a relatively microbe-selective, haloperoxidase antiseptic system that is: (1) capable of potent, broad spectrum pathogen killing, (2) sparing of and even selective for normal flora, and (3) non-toxic to host cells and does not interfere with the host immune response.

(3) Killing of E. coli in the Absence of Erythrocytes. The data of Table 14 further illustrate the effect of MPO on streptococci-dependent killing of E. coli. For each reaction approximately $2*10^6$ E. coli and $5*10^7$ Streptococci sp. (viridans) were incubated for 30 minutes at 23° C. with the indicated quantity of MPO. Streptococci do not kill E. coli in the absence of MPO. Rather, E. coli totally inhibited the growth of streptococci in the absence of MPO. Addition of 3.7 pmol MPO effects a greater than 99% kill of E. coli. This concentration of MPO also caused the emergence of streptococci colonies relative to the disappearance of E. coli colonies. 11.1 pmol MPO produced a total E. coli kill with relative sparing of streptococci, but at 100 pmol MPO the streptococcal count was decreased by over two order of magnitude.

E. coli has a small number of high affinity and a large number of relatively low affinity MPO binding sites as described in Table 10. The total MPO binding capacities of E. coli is greater than that of streptococci but less than that previously described for Staph. aureus. However, the streptococcal-MPO combination exerts a greater killing capacity for E. coli than for Staph. aureus. Greater than 99% kill of the $2*10^6$ E. coli was effected with $2*10^{12}$ molecules of MPO, i.e., approximately $10^6$ molecules MPO/E. coli. Increased relative kill capacity may reflect greater E. coli susceptibility to MPO-generated reactants such as HOCl and $^1O_2$.

The lesser MPO binding capacity of E. coli translates to a higher residual MPO available for streptococci binding. Consequently, the effect of 100 pmol MPO on streptococci killing in the presence of E. coli is greater than streptococcus killing in the presence of Staph. aureus.

(4) Killing of E. coli in the Presence of Erythrocytes. The effect of $10^7$ RBCs on viridans streptococci-dependent killing of E. coli in the presence of MPO is also shown in Table 14. Inclusion of 3.7 pmol MPO caused a 50% decrease in E. coli colonies and the emergence of streptococci colonies. At 11.1 pmol MPO the E. coli count was diminished by greater than 99%, i.e., to $1*10^4$ CFU, without any deleterious effect on streptococci. Complete killing of E. coli and a small decrease in streptococci were effected with 100 pmol MPO.

As previously observed with Staph. aureus, inclusion of $10^7$ RBCs in the reaction system produces a small, approximate threefold, inhibition of E. coli killing. The added RBCs also inhibit streptococci killing associated with relatively high MPO concentrations. As described in Table 14, quantities of MPO producing total E. coli killing did NOT produce hemolysis. As previously observed for Staph. aureus killing in the presence of RBCs, introduction of a small quantity of MPO to the mixed microbial suspension produces a selective and total destruction of E. coli, selectively favors the dominance of nonpathogenic streptococci, and does not cause injury to bystander erythrocytes.

(5) Killing of P. aeruginosa in the Absence and Presence of Erythrocytes.

Of all the microbes tested, P. aeruginosa is the most susceptible to MPO microbicidal action. The data of Table 14 indicate a greater than 99% kill using 0.4 pmol MPO in the absence of RBCs, and an 85% kill using 1.2 pmol MPO in the presence of RBCs. Hemolytic damage was not observed at any of MPO concentrations tested.

The results of this killing study are in agreement with the binding data of Table 10. P. aeruginosa has a small number of extremely high affinity MPO binding sites and a large number of high affinity binding sites. The overall MPO binding capacity of P. aeruginosa is greater than that of the other microbes tested.

(6) Killing of Candida albicans in the Absence and Presence of Erythrocytes.

Candida albicans is susceptible to MPO-dependent microbicidal action. As shown in Table 14, 1.2 pmol MPO produces a 97% kill in the absence of RBCs. However, killing is greatly compromised by the presence of RBCs. 100 pmol MPO are required for approximately the same kill activity in the presence of RBCs without evidence of hemolysis.

The result of MPO-dependent Candida albicans killing agree with the results of the MPO-Candida albicans binding as presented in Table 10. Candida albicans, a eukaryotic yeast, is relatively large in comparison with the bacteria tested. Each yeast contains approximately $10^4$ MPO binding sites, but these sites are of relatively low affinity. The overall MPO binding capacity for Candida albicans is greater than for Streptococcus sp. (viridans) and for RBCs. MPO plus viridans streptococci effectively kill candida. Erythrocyte inhibition of candida killing probably reflects the destruction of viridans streptococcal $H_2O_2$ by RBC catalase in combination with relatively poor MPO binding affinity.

Candida albicans lies in the gray area between normal flora and pathogen. It is typically present and accounts for a small percentage of the normal flora. Candida becomes a problem in the immunocompromised host especially in association with the use of prokaryote-specific antibiotics that in effect select out for candida overgrowth and superinfection. The data of Table 14 demonstrate the synergistic action of viridans streptococci in combination with MPO for candida killing and suppression of yeast overgrowth.

(7) Direct MPO killing of Streptococcus pyogenes (Group A) and Streptococcus agalactiae (Group B).

Materials: The bacteria, all members of the genus Streptococcus, were grown overnight in Todd-Hewitt broth (THB). The RBCs and MPO were prepared and quantified as described in Examples 1 and 2.

Methods: 100 µl of target microbe suspension (approximately $10^6$ microbes), 100 µl of MPO (concentration varied), 100 µl of glucose (1 mg), 600 µl of NS, and where indicated, either 100 µl of erythrocyte suspension ($10^7$ RBCs) or NS were added to each tube for a 1 ml final volume. The contents were gently mixed, and the tubes were incubated for 30 minutes at 23° C. Microbial killing was measured by agar plate dilution as previously described in Example 1 except that the colonies were plated on blood agar and were allowed to grow for 2 days in order to fully develop the small colonies and hemolytic patterns.

Many, but not all, members of the genus Streptococcus generate $H_2O_2$ as a product of metabolism. The results presented in Table 10 indicate that members of the genus Streptococcus also differ with regard to MPO binding capacity. These observations suggest possible differences in susceptibility to MPO killing. The results presented in Table 15 substantiate this possibility.

TABLE 15

Direct Microbicidal Action of Myeloperoxidase Against Various Streptococci:

| Organism: | MPO, pmol | No RBC CFU: | RBC ($10^7$) CFU: | Hemoglobin: Pel. | Super. |
|---|---|---|---|---|---|
| Strep. (viridans) | None | 800,000 | 260,000 | 0.7 | 0.3 |
| alpha strep | 100.0 | 0 | 22,000 | 0.1 | 0.8 |
| | 33.3 | 0 | 33,000 | 0.3 | 0.7 |
| | 11.1 | 0 | 30,000 | 0.7 | 0.4 |
| | 3.7 | 0 | 63,000 | 1.0 | 0.0 |
| | 1.2 | 600 | 200,000 | 0.7 | 0.2 |
| | 0.4 | 26,000 | 160,000 | 1.3 | 0.0 |
| | 0.13 | 37,000 | 130,000 | — | — |
| St. pyogenes | None | 2,500,000 | 970,000 | 1.0 | 0.1 |
| Group A | 100.0 | 0 | 290,000 | 0.8 | 0.1 |
| | 33.3 | 0 | 280,000 | 1.0 | 0.1 |
| | 11.1 | 0 | 260,000 | 0.7 | 0.0 |
| | 3.7 | 0 | 300,000 | 1.0 | 0.0 |
| | 1.2 | 0 | 130,000 | 0.8 | 0.0 |
| | 0.4 | 600 | 750,000 | 1.0 | 0.0 |
| | 0.13 | 1,300,000 | 970,000 | 1.4 | 0.0 |
| St. agalactiae | None | 740,000 | 930,000 | 1.0 | 0.0 |
| Group B | 100.0 | 0 | 0 | 0.6 | 0.0 |
| | 33.3 | 0 | 0 | 0.7 | 0.1 |
| | 11.1 | 0 | 0 | 0.5 | 0.0 |
| | 3.7 | 750,000 | 6,200 | 0.8 | 0.0 |
| | 1.2 | 1,700,000 | 1,300,000 | 1.0 | 0.0 |
| | 0.4 | 1,100,000 | 1,200,000 | 1.0 | 0.0 |
| | 0.13 | 1,200,000 | 1,300,000 | 1.0 | 0.0 |
| St. faecalis | None | 1,900,000 | 1,700,000 | 1.0 | 0.0 |
| Group D | 100.0 | 1,600,000 | 1,500,000 | 0.5 | 0.0 |
| | 33.3 | 1,900,000 | 1,300,000 | 1.1 | 0.3 |
| | 11.1 | 1,700,000 | 1,500,000 | 0.7 | 0.0 |
| | 3.7 | 1,500,000 | 1,400,000 | 0.6 | 0.1 |
| | 1.2 | 1,500,000 | 1,600,000 | 1.4 | 0.0 |
| | 0.4 | 1,700,000 | 1,700,000 | 1.0 | 0.0 |
| | 0.13 | 1,800,000 | 1,500,000 | 1.1 | 0.0 |

MPO effects direct killing of *Streptococcus sp.* (viridans), *Streptococcus pyogenes* (Group A), and *Streptococcus agalactiae* (Group B), but does produce a direct kill of *Streptococcus faecalis* (Group D). The presence of RBCs diminished MPO microbicidal action, but there was minimal hemolysis.

With respect to MPO kill, *Streptococcus pyogenes* (Group A) is more susceptible than *Streptococcus agalactiae* (Group B) and *Streptococcus sp.* (viridans) in the absence of RBCs. This order is in agreement with the MPO binding affinities and capacities listed in Table 10. The binding-kill correlation is distorted by the presence of RBCs. RBCs do not bind MPO, but contain catalase capable of destroying $H_2O_2$. Differential inhibition of microbe killing may reflect the action of a constant quantity of RBC catalase relative to the different rates of $H_2O_2$ generation by the various streptococci.

*Streptococcus faecalis* (Group D) is the only member of the group tested that is not alpha or beta hemolytic and does not release $H_2O_2$ as a product of metabolism. Thus, despite having the highest MPO binding affinity and capacity, *St. faecalis* is protected from the action of MPO in the absence of an exogenous source of $H_2O_2$.

These observations document direct MPO killing of pathogenic members of the LAB family, and demonstrate the therapeutic utility of MPO for eliminating Group A and/or Group B streptococcal colonization or Infection.

(8) Viridans Streptococci-Chloroperoxidase Synergistic Microbicidal Action in the Absence and Presence of Erythrocytes.

Materials: The bacteria, yeast and RBCs were prepared and quantified as described supra. CPO was purchased from Sigma Chemical Co. and prepared as described in Example 7.

Methods: The methodology was as previously described supra, except that CPO was the haloperoxidase employed.

CPO was substituted for MPO in order to provide data for comparative analysis of haloperoxidase action. The microbicidal capacity of CPO in combination with viridans streptococci was tested using the three bacteria and one yeast previously described, and the results are presented in Table 16.

TABLE 16

Chloroperoxidase-Dependent Viridans Streptococcal Microbicidal Action in the Absence and Presence of Erythrocytes

| Organism: | CPO, pmol | No RBC CFU: | RBC ($10^7$) CFU: | Hemoglobin: Pel. | Super. |
|---|---|---|---|---|---|
| P. aeruginosa | None | 2,400,000 | 2,000,000 | 0.9 | 0.0 |
| | 100.0 | 0 | 4,400 | 0.0 | 1.0 |
| | 33.3 | 200 | 5,300 | 0.0 | 1.1 |
| | 11.1 | 100 | 29,000 | 0.0 | 1.2 |
| | 3.7 | 1,100 | 10,000 | 0.7 | 0.2 |
| | 1.2 | 1,700 | 57,000 | 1.0 | 0.0 |
| | 0.4 | 23,000 | 390,000 | 1.2 | 0.0 |
| | 0.13 | 52,000 | 1,800,000 | 0.7 | 0.0 |
| E. coli | None | 2,500,000 | 2,800,000 | 1.0 | 0.0 |
| | 100.0 | 0 | 2,500 | 0.3 | 0.9 |
| | 33.3 | 0 | 6,000 | 1.1 | 0.0 |
| | 11.1 | 0 | 6,500 | 1.0 | 0.0 |
| | 3.7 | 0 | 81,000 | 0.9 | 0.0 |
| | 1.2 | 200 | 2,500,000 | 1.0 | 0.1 |
| | 0.4 | 2,600 | 2,400,000 | 1.0 | 0.0 |
| | 0.13 | 650,000 | 2,200,000 | 0.9 | 0.1 |
| Staph. aureus | None | 2,400,000 | 2,000,000 | 1.1 | 0.0 |
| | 100.0 | 30,000 | 6,200 | 0.1 | 0.9 |
| | 33.3 | 0 | 6,000 | 0.5 | 0.5 |
| | 11.1 | 500 | 1,500,000 | 1.0 | 0.0 |
| | 3.7 | 510,000 | 2,500,000 | 1.0 | 0.0 |
| | 1.2 | 1,600,000 | 2,500,000 | 0.8 | 0.0 |
| | 0.4 | 1,700,000 | 2,600,000 | 1.0 | 0.0 |
| | 0.13 | 2,000,000 | 2,700,000 | 1.0 | 0.1 |
| Cand. albicans | None | 550,000 | 840,000 | 1.2 | 0.1 |
| | 100.0 | 350,000 | 520,000 | 0.0 | 0.5 |
| | 33.3 | 310,000 | 450,000 | 0.0 | 1.3 |
| | 11.1 | 380,000 | 640,000 | 0.3 | 1.1 |
| | 3.7 | 430,000 | 560,000 | 1.0 | 0.0 |
| | 1.2 | 430,000 | 530,000 | 1.0 | 0.0 |
| | 0.4 | 440,000 | 520,000 | 1.0 | 0.1 |
| | 0.13 | 430,000 | 870,000 | 0.7 | 0.2 |

In the absence of RBCs, viridans streptococci exert a CPO-dependent bactericidal activity comparable to that previously obtained with the viridans streptococci-MPO system, but unlike the MPO system, the CPO system did not effectively kill *Candida albicans*. Both MPO and CPO have comparable activities with regard to halide oxidation and $^1O_2$ production, but comparison of MPO and CPO binding data of Tables 10 and 11, demonstrates the magnitudinally greater microbe binding capacity of MPO.

Both MPO and CPO generation of HOCl and $^1O_2$ produce a microbicidal effect, but the CPO system lacks the high degree of specificity required for selective kill with minimal collateral damage. Candida is not killed by CPO at any of the concentrations tested. Collateral damage in the form of hemolysis is observed above 10 pmol CPO/ml.

Example 10

Optimal Ranges of Chloride/$H_2O_2$ and Bromide/$H_2O_2$ Ratios for Haloperoxidase Microbicidal Action.

Materials: Candida albicans was prepared and quantified as described in Example 10. EPO and MPO were prepared as described in Example 2.

Methods: The methodology was as previously described for Example 3 except that both EPO and MPO were employed, and that both halide, i.e., $Cl^-$ and $Br^-$, and $H_2O_2$ concentrations were varied.

As previously considered in Example 3, the halide/$H_2O_2$ ratio is the critical factor with regard to haloperoxidase stability and functionality. At very low ratios, $H_2O_2$ can inhibit haloperoxidase function, and at extremely high ratios, halide can competitively block catalysis.

Table 17 presents data relating $Cl/H_2O_2$ ratio to MPO and EPO dependent killing of Candida albicans. Candida was chosen as the target microbe because of its resistance to the direct action of $H_2O_2$. The data are presented as the Candida albicans CFU. The $Cl^-/H_2O_2$ ratio is presented below and the percent kill is presented below the ratio.

TABLE 17

The Effect of $Cl^-:H_2O_2$ Ratio and Quantity on Myeloperoxidase and Eosinophil Peroxidase Dependent Killing of Candida albicans:

| $H_2O_2$, $\mu$mol | Chloride, $\mu$mol | | | | |
|---|---|---|---|---|---|
| | None | 0.10 | 1.00 | 10.00 | 100.00 |
| Myeloperoxidase: 1 pmol | | | | | |
| None | 900,000[1] | 500,000 | 820,000 | 720,000 | 840,000 |
| | (0.00)[2] | (Inf.) | (Inf.) | (Inf.) | (Inf.) |
| | 0.0%[3] | 44.4% | 8.9% | 20.0% | 6.7% |
| 0.0025 | 900,000 | 640,000 | 620,000 | 40,000 | 0 |
| | (0.00) | (40.00) | (400.00) | (4000.00) | (40000.00) |
| | 0.0% | 28.9% | 31.1% | 95.6% | 100.0% |
| 0.0500 | 580,000 | 780,000 | 720,000 | 10,000 | 0 |
| | (0.00) | (2.00) | (20.00) | (200.00) | (2000.00) |
| | 35.6% | 13.3% | 20.0% | 98.9% | 100.0% |
| 1.0000 | 560,000 | 700,000 | 480,000 | 280,000 | 480,000 |
| | (0.00) | (0.10) | (1.00) | (10.00) | (100.00) |
| | 37.8% | 22.2% | 46.7% | 68.9% | 46.7% |

TABLE 17-continued

The Effect of $Cl^-:H_2O_2$ Ratio and Quantity on Myeloperoxidase and Eosinophil Peroxidase Dependent Killing of Candida albicans:

| $H_2O_2$, $\mu$mol | Chloride, $\mu$mol | | | | |
|---|---|---|---|---|---|
| | None | 0.10 | 1.00 | 10.00 | 100.00 |
| Eosinophil Peroxidase: 1 pmol | | | | | |
| None | 960,000 | 860,000 | 960,000 | 980,000 | 1,200,000 |
| | (0.00) | (Inf.) | (Inf.) | (Inf.) | (Inf.) |
| | 0.0% | 10.4% | 0.0% | -2.1% | -25.0% |
| 0.0025 | 820,000 | 960,000 | 1,000,000 | 780,000 | 660,000 |
| | (0.00) | (40.00) | (400.00) | (4000.00) | (40000.00) |
| | 14.6% | 0.0% | -4.2% | 18.8% | 31.4% |
| 0.0500 | 960,000 | 900,000 | 760,000: | 740,000 | 540,000 |
| | (0.00) | (2.00) | (20.00) | (200.00) | (2000.00) |
| | 0.0% | 6.3% | 20.8% | 22.9% | 43.8% |
| 1.0000 | 780,000 | 700,000 | 840,000 | 900,000 | 800,000 |
| | (0.00) | (0.10) | (1.00) | (10.00) | (100.00) |
| | 18.8% | 27.1% | 12.5% | 6.3% | 16.7% |

[1]The number of colony forming units of Candida albicans.
[2]The ratio of $Cl^-/H_2O_2$.
[3]The percent Candida albicans killed.

With MPO as the haloperoxidase, candidicidal action was detected with $Cl^-/H_2O_2$ ratios of 1 through 40,000, and essentially complete killing was observed in the 200 to 40,000 range. The halide/$H_2O_2$ ratio is an important consideration in formulating an effective microbicidal environment. At low $H_2O_2$ concentrations, a relatively high ratio is essentially guaranteed because $Cl^-$ is an ubiquitous component of body fluids. In normal subjects (human) plasma $Cl^-$ levels range from 98–107 $\mu$mol/ml; cerebrospinal fluid levels range from 119–131 $\mu$mol/ml; saliva levels range from 7–43 $\mu$mol/ml, and sweat levels range from 4–60 $\mu$mol/ml. Stimulated gastric secretion ranges from 460–1,040 $\mu$mol/min, and urinary excretion ranges from 80,000–270,000 $\mu$mol/day (Geigy Scientific Tables, 8th ed., 1981, Ciba-Geigy Ltd., Basel, Switzerland). It is difficult to obtain a body fluid containing less than 5 $\mu$mol/ml, and therefore, the concentrations of available $H_2O_2$ should be maintained below 5 $\mu$mol/ml, preferably below 0.5 $\mu$mol/ml, and most preferentially below 0.05 $\mu$mol/ml for most antiseptic and selective antimicrobial applications of the enzyme.

With EPO as the haloperoxidase, candidicidal action was NOT effective within the 0 to 40,000 range of $Cl/H_2O_2$ ratios tested. As described supra, chloride is relatively ineffective as the halide cofactor for EPO microbicidal action.

The Table 18 data relate $Br/H_2O_2$ ratio to MPO and EPO dependent killing of Candida albicans. The data are presented as previously described for Table 17.

TABLE 18

The Effect of Br⁻:H$_2$O$_2$ Ratio and Quantity on Myeloperoxidase
and Eosinophil Peroxidase Dependent Killing of *Candida albicans*:

| H$_2$O$_2$, µmol | Bromide, µmol | | | | | |
|---|---|---|---|---|---|---|
| | None | 0.001 | 0.01 | 0.10 | 1.00 | 10.00 |
| Myeloperoxidase: 1 pmol | | | | | | |
| None | 900,000[1] | 580,000 | 720,000 | 720,000 | 640,000 | 720,000 |
|  | (0.00)[2] | (Inf.) | (Inf.) | (Inf.) | (Inf.) | (Inf.) |
|  | 0.0%[3] | 35.6% | 20.0% | 20.0% | 28.9% | 20.0% |
| 0.0025 | 900,000 | 500,000 | 700,000 | 9,000 | 80,000 | 620,000 |
|  | (0.00) | (0.40) | (4.00) | (40.00) | (400.00) | (4000.00) |
|  | 0.0% | 44.4% | 22.2% | 99.0% | 91.1% | 31.1% |
| 0.0500 | 580,000 | 640,000 | 660,000 | 520,000 | 40,000 | 420,000 |
|  | (0.00) | (0.02) | (0.20) | (2.00) | (20.00) | (200.00) |
|  | 35.6% | 28.9% | 26.7% | 42.2% | 95.6% | 53.3% |
| 1.0000 | 560,000 | 1,000,000 | 500,000 | 540,000 | 620,000 | 540,000 |
|  | (0.00) | (0.001) | (0.01) | (0.10) | (1.00) | (10.00) |
|  | 37.8% | −11.1% | 44.4% | 40.0% | 31.1% | 40.0% |
| Eosinophil Peroxidase: 1 pmol | | | | | | |
| None | 960,000 | 900,000 | 900,000 | 960,000 | 760,000 | 1,200,000 |
|  | (0.00) | (Inf.) | (Inf.) | (Inf.) | (Inf.) | (Inf.) |
|  | 0.0% | 6.3% | 6.3% | 0.0% | 20.8% | −25.0% |
| 0.0025 | 820,000 | 700,000 | 24,000 | 26,000 | 120,000 | 540,000 |
|  | (0.00) | (0.40) | (4.00) | (40.00) | (400.00) | (4000.00) |
|  | 14.6% | 27.1% | 97.5% | 97.3% | 87.5% | 43.8% |
| 0.0500 | 960,000 | 640,000 | 460,000 | 0 | 0 | 0 |
|  | (0.00) | (0.02) | (0.20) | (2.00) | (20.00) | (200.00) |
|  | 0.0% | 33.3% | 52.1% | 100.0% | 100.0% | 100.0% |
| 1.0000 | 780,000 | 560,000 | 780,000 | 660,000 | 600,000 | 0 |
|  | (0.00) | (0.001) | (0.01) | (0.10) | (1.00) | (10.00) |
|  | 18.8% | 41.7% | 18.8% | 31.3% | 37.5% | 100.0% |

[1]The number of colony forming units of *Candida albicans*.
[2]The ratio of Br⁻/H$_2$O$_2$.
[3]The percent *Candida albicans* killed.

With MPO as the haloperoxidase, candidicidal action was detected with Br⁻/H$_2$O$_2$ ratios of 2 through 4,000, and essentially complete killing was observed in the 20 to 400 range. With EPO as the haloperoxidase, killing was detected in the 0.2 through 4,000 range of Br/H$_2$O$_2$ ratios, and essentially complete killing was obtained in the 2 through 400 range. The increased candidicidal effectiveness of EPO relative to MPO is in agreement with the relative binding affinities of these haloperoxidases for *Candida albicans* as presented in Tables 10 and 13.

In normal human subjects, Br⁻ plasma levels range from 0.049–0.93 µmol/ml; cerebrospinal fluid levels range from 0.018–0.048 µmol/ml; saliva levels range from 0.003–0.013 µmol/ml, and sweat levels range from 0.002–0.006 µmol/ml. Br⁻ is preferentially secreted over Cl⁻ by the gastric parietal cells, and urinary excretion ranges from 20–84 µmol/day (Geigy Scientific Tables, 8th ed., 1981, Ciba-Geigy Ltd., Basel, Switzerland). The concentration of Br⁻ available in body fluids is typically in the 5 nmol to 90 nmol/ml range. Therefore, in the absence of Br supplementation, the concentration of available H$_2$O$_2$ should be maintained below 0.01 µmol/ml, preferably below 0.001 µmol/ml for most antiseptic or antimicrobial applications of bromide-requiring haloperoxidases such as EPO or LPO.

Bromide is therapeutically employed for the treatment of epilepsy. The therapeutic range is reported as 9–18 µmol/ml with toxicity above 16 µmol/ml (Cecil's Textbook of Medicine, 18th ed., 1988, W.B. Saunders Co., Philadelphia). It is therefore possible to increase the Br⁻ concentration of body fluids by ten to a hundredfold without toxicity. As such, if EPO or LPO is the haloperoxidase of choice, the Br⁻ can be included in the formulation to a concentration below the toxic range, and H$_2$O$_2$ concentration can be proportionally increased to maintain the Br⁻/H$_2$O$_2$ ratio within the optimum range.

Example 11

The Effect of High Concentrations of Competitive Substrates on MPO Bacterial Action Microbe-selective binding properties in combination with potent microbicidal action suggest the use of haloperoxidase for microbe killing with minimal collateral damage to media components and selective control of microbial flora. In order to fully realize these possibilities, haloperoxidases must effectively kill microbes in media saturated with competitive substrates. The following experiment was conducted to test the effect of a complex medium on myeloperoxidase bactericidal activity.

Materials and Methods: The materials and methods were as described for Example 3 except that the reaction medium contained Similac® infant formula (Ross Laboratories, Div. Abbott Laboratories) at a dilution of ½ standard concentration.

The data of Table 19 present the MPO-dependent bactericidal action of various concentrations of H$_2$O$_2$ on *E. coli* and *Staphylococcus aureus* in the presence of a ½ standard concentration of Similac®. MPO-dependent microbicidal action with various concentrations of H$_2$O$_2$ has been previously described in Example 3 and is illustrated by the data of Table 8A.

Similac® is a complex suspension of protein, fat, carbohydrate and vitamins. At the concentration employed for testing, each ml of medium contained 10 pmol MPO and the indicated quantity of $H_2O_2$, plus 7.5 mg protein, 18 mg fat of which 4.4 mg were linoleic acid, 36 mg of carbohydrate, and 30 μg ascorbic acid (vitamin C). Relatively high concentrations of competitive substrates, such as linoleic acid, and reductants, such as ascorbic acid, produce a large inhibition of MPO microbicidal action, but despite this inhibition, residual MPO microbicidal capacity remains potent. The data of Table 19 show that bactericidal action is complete with less than 0.6 μmol/ml $H_2O_2$.

TABLE 19

The Effect of Similac ® Infant Formula on Myeloperoxidase Dependent $H_2O_2$ Kill Capacity

| Organism: | $H_2O_2$, μmol | MPO, none CFU: | MPO, 10 pmol CFU: |
|---|---|---|---|
| E. coli | None | 6,700,000 | 4,500,000 |
|  | 700 | 0 | 0 |
|  | 70 | 0 | 0 |
|  | 14 | 300,000 | 0 |
|  | 2.8 | 3,800,000 | 0 |
|  | 0.56 | 3,900,000 | 0 |
|  | 0.112 | 3,200,000 | 3,400,000 |
|  | 0.0224 | 3,400,000 | 3,500,000 |
|  | 0.00448 | 3,100,000 | 4,700,000 |
|  | 0.000896 | 2,800,000 | 3,100,000 |
| Staph. aureua | None | 4,000,000 | 5,300,000 |
|  | 700 | 0 | 0 |
|  | 70 | 0 | 0 |
|  | 14 | 3,000,000 | 0 |
|  | 2.8 | 4,400,000 | 0 |
|  | 0.56 | 4,500,000 | 0 |
|  | 0.112 | 4,900,000 | 5,500,000 |
|  | 0.0224 | 3,600,000 | 5,900,000 |
|  | 0.00448 | 3,000,000 | 5,300,000 |
|  | 0.000896 | 5,300,000 | 5,300,000 |

Similac ® was employed at ½ standard concentration. Each ml of the test suspension contained 7.5 mg protein, 18 mg fat of which 4.4 mg was linoleic acid, 36 mg carbohydrate, and 30 μg ascorbic acid.

Microbe binding haloperoxidases can be employed in relatively low concentration for sterilizing complex media. Likewise, the microbe-specific binding and killing properties of haloperoxidases as described in Examples 6 through 9 indicate their potential role in selective control of flora composition. These haloperoxidases can be applied for control of fermentation processes as well as for medical therapy.

Various modifications and adaptations of the antiseptic methods and compositions of the invention will be apparent from the foregoing to those skilled in the art. Any such modifications and adaptations are intended to be within the scope of the appended claims except insofar as precluded by the prior art.

What is claimed is:

1. A method of selectively inhibiting the growth of pathogenic microbes while not eliminating normal flora in an animal in need of such treatment, comprising the steps of:
   a) administering to the animal an amount of a haloperoxidase which is therapeutically effective, in the presence of
      i) a peroxide and
      ii) bromide or chloride,
   wherein said haloperoxidase is selected from the group consisting of myeloperoxidase and eosinophil peroxidase, and said haloperoxidase is employed without derivatization to enhance target microbe specificity or affinity,
   b) selectively binding said haloperoxidase to the pathogenic microbes,
   c) oxidizing the halide and
   d) selectively killing the pathogenic microbes while not eliminating the normal flora of the animal.

2. The method of claim 1 which further comprises administering to the animal an amount of normal flora effective to facilitate recolonization of the normal flora of the animal.

3. The method of claim 1, wherein the haloperoxidase is a myeloperoxidase.

4. The method of claim 3 wherein the halide is chloride and which further comprises maintaining the ratio of chloride to peroxide in the range of about 1 to about 40,000 at the site of the pathogenic microbes.

5. The method of claim 4 wherein the ratio of chloride to peroxide is maintained in the range of about 200 to about 40,000.

6. The method of claim 1, wherein the haloperoxidase is eosinophil peroxidase and the halide is bromide.

7. The method of claim 6 which further comprises maintaining the ratio of bromide to peroxide in the range of about 0.1 to about 4,000 at the site of the pathogenic microbes.

8. The method of claim 7 wherein the ratio of bromide to peroxide is maintained in the range of about 1 to about 1,000.

9. The method of claim 1 wherein the haloperoxidase is administered to the animal in the form of a liquid solution and from about 0.01 pmol to about 500 pmol haloperoxidase per ml of the solution is administered to the animal.

10. The method of claim 9 wherein from about 0.1 pmol to about 50 pmol haloperoxidase per ml of the solution is administered to the animal.

11. The method of claim 10 wherein from about 0.5 pmol to about 5 pmol haloperoxidase per ml of the solution is administered to the animal.

12. The method of claim 1 which further comprises administering to the animal, in addition to the haloperoxidase, a peroxide or an agent capable of producing a peroxide when administered to the animal.

13. A method of selectively inhibiting the growth of pathogenic microbes while not eliminating normal flora in an animal with an infection, comprising the steps of:
   a) administering to the animal having said infection an amount of a haloperoxidase which is antiseptically effective, in the presence of
      i) a peroxide and
      ii) bromide or chloride,
   wherein the haloperoxidase is selected from the group consisting of myeloperoxidase and eosinophil peroxidase, and said haloperoxidase is employed without derivatization to enhance target microbe specificity or affinity,
   b) selectively binding said haloperoxidase to the pathogenic microbes,
   c) oxidizing the halide and
   d) selectively killing the pathogenic microbes while not eliminating the normal flora of the animal.

14. The method of claim 13 which further comprises administering to the animal an amount of normal flora effective to facilitate recolonization of the normal flora in the animal.

15. The method of claim 13, wherein the haloperoxidase is myeloperoxidase.

16. The method of claim 15 wherein the halide is chloride and which further comprises maintaining the ratio of chloride to peroxide in the range of about 1 to about 40,000 at the site of infection.

17. The method of claim 16 wherein the ratio of chloride to peroxide is maintained in the range of about 200 to about 40,000.

18. The method of claim 13, wherein the haloperoxidase is eosinophil peroxidase and the halide is bromide.

19. The method of claim 18 which further comprises maintaining the ratio of bromide to peroxide in the range of about 0.1 to about 4,000 at the site of infection.

20. The method of claim 19 wherein the ratio of bromide to peroxide is maintained in the range of about 1 to about 1,000.

21. The method of claim 13, wherein the haloperoxidase is administered to the animal in the form of a liquid solution and from about 0.01 pmol to about 500 pmol haloperoxidase per ml of the solution is administered to the animal.

22. The method of claim 21 wherein from about 0.1 pmol to about 50 pmol haloperoxidase per ml of the solution is administered to the animal.

23. The method of claim 22 wherein from about 0.5 pmol to about 5 pmol haloperoxidase per ml of the solution is administered to the animal.

24. The method of claim 13 which further comprises administering to the animal a peroxide or an agent capable of producing a peroxide when administered to the animal.

25. The method of claim 1 wherein said animal is a human.

26. The method of claim 13 wherein said animal is a human.

27. A method of selectively inhibiting the growth of pathogenic microbes while not eliminating normal flora in an animal in need of such treatment, comprising the steps of:
   a) administering to the animal an amount of a haloperoxidase which is therapeutically effective, in the presence of
      i) a peroxide and
      ii) bromide or chloride,
   wherein said haloperoxidase is selected from the group consisting of myeloperoxidase, eosinophil peroxidase and said haloperoxidase is employed without derivatization to enhance target microbe specificity or affinity,
   b) selectively binding said haloperoxidase to the pathogenic microbes,
   c) oxidizing the halide,
   d) selectively killing the pathogenic microbes while not eliminating the normal flora of the animal, and
   e) maintaining the ratio of chloride to peroxide in the range of about 1 to about 40,000 when the halide is chloride or maintaining the ratio of bromide to peroxide in the range of about 0.1 to about 4,000 when the halide is bromide, at the site of the pathogenic microbes.

28. The method of claim 27 which further comprises administering to the animal an amount of normal flora effective to facilitate recolonization of the normal flora of the animal.

29. The method of claim 27, wherein the haloperoxidase is a myeloperoxidase.

30. The method of claim 29 wherein the halide is chloride and the ratio of chloride to peroxide is maintained in the range of about 200 to about 40,000.

31. The method of claim 27, wherein the haloperoxidase is eosinophil peroxidase, and the halide is bromide.

32. The method of claim 31 wherein the ratio of bromide to peroxide is maintained in the range of about 1 to about 1,000.

33. The method of claim 27 wherein the haloperoxidase is administered to the animal in the form of a liquid solution and from about 0.01 pmol to about 500 pmol haloperoxidase per ml of the solution is administered to the animal.

34. The method of claim 33 wherein from about 0.1 pmol to about 50 pmol haloperoxidase per ml of the solution is administered to the animal.

35. The method of claim 34 wherein from about 0.5 pmol to about 5 pmol haloperoxidase per ml of the solution is administered to the animal.

36. The method of claim 27 which further comprises administering to the animal, in addition to the haloperoxidase, a peroxide or an agent capable of producing a peroxide when administered to the animal.

37. A method of selectively inhibiting the growth of pathogenic microbes while not eliminating normal flora in an animal with an infection, comprising the steps of:
   a) administering to the animal having said infection an amount of a haloperoxidase which is antiseptically effective, in the presence of
      i) a peroxide and
      ii) bromide or chloride,
   wherein the haloperoxidase is selected from the group consisting of myeloperoxidase, eosinophil peroxidase and said haloperoxidase is employed without derivatization to enhance target microbe specificity or affinity,
   b) selectively binding said haloperoxidase to the pathogenic microbes,
   c) oxidizing the halide,
   d) selectively killing the pathogenic microbes while not eliminating the normal flora of the animal, and
   e) maintaining the ratio of chloride to peroxide in the range of about 1 to at about 40,000 when the halide is chloride or maintaining the ratio of bromide to peroxide in the range of about 0.1 to about 4,000 when the halide is bromide, at the site of the pathogenic microbes.

38. The method of claim 37 which further comprises administering to the animal an amount of normal flora effective to facilitate recolonization of the normal flora in the animal.

39. The method of claim 37, wherein the haloperoxidase is myeloperoxidase.

40. The method of claim 37 wherein the halide is chloride and the ratio of chloride to peroxide is maintained in the range of about 200 to about 40,000.

41. The method of claim 37, wherein the haloperoxidase is eosinophil peroxidase and the halide is bromide.

42. The method of claim 41 wherein the ratio of bromide to peroxide is maintained in the range of about 1 to about 1,000.

43. The method of claim 37, wherein the haloperoxidase is administered to the animal in the form of a liquid solution and from about 0.01 pmol to about 500 pmol haloperoxidase per ml of the solution is administered to the animal.

44. The method of claim 43 wherein from about 0.1 pmol to about 50 pmol haloperoxidase per ml of the solution is administered to the animal.

45. The method of claim 44 wherein from about 0.5 pmol to about 5 pmol haloperoxidase per ml of the solution is administered to the animal.

46. The method of claim 37 which further comprises administering to the animal a peroxide or an agent capable of producing a peroxide when administered to the animal.

47. The method of claim 27 wherein said animal is a human.

48. The method of claim 37 wherein said animal is a human.

* * * * *

UNITED STATES PATENT AND TRADEMARK OFFICE
CERTIFICATE OF CORRECTION

PATENT NO.       : 6,294,168 B1
APPLICATION NO.  : 08/271583
DATED            : September 25, 2001
INVENTOR(S)      : R.C. Allen It is certified that error appears in the above-identified patent and that said Letters Patent is hereby corrected as shown below:

| COLUMN | LINE | ERROR |
|---|---|---|
| Pg. 1, col. 1 | Assistant Examiner | "Mike Meller" should read --Michael V. Meller-- |
| 1 | 51-52 | "photok-illing" should break --photo-killing-- |
| 2 | 3 | "Initially" should read --initially-- |
| 4 | 6 | "$^1$dye*" should read --$^1$Dye*-- |
| 4 | 15 | "$^1$Dye - - - $hv$→$^1$Dye*- - - ISC→$^3$Dye*" should read --$^1$Dye --- $hv$---> $^1$Dye * ---ISC---> $^3$Dye *-- |
| 4 | 31 | "$^3$Dye*+$^1$SubH→$^2$Dye+$^2$Sub." should read --$^3$Dye * + $^1$SubH - - - > $^2$Dye + $^2$Sub•-- |
| 4 | 43 | "$^2$Dye*+$^3$O$_2$→$^1$Dye+$^2$.O$_2$H(or $^2$.O$_2$-)" should read --$^2$Dye + $^3$O$_2$---> $^1$Dye + $^2$•O$_2$H (or $^2$•O$_2$-)-- |
| 4 | 47 | "$^2$.O$_2$H+$^2$.O$_2$-+H$^+$→$^1$H$_2$O$_2$+$^1$O$_2$" should read --$^2$•O$_2$H + $^2$•O$_2$-+ H$^+$ ----> $^1$H$_2$O$_2$+ $^1$O$_2$-- |
| 4 | 60 | "$^3$Dye*+$^3$O$_2$- - - $^1$DyeO$_2$→$^1$Dye+$^1$O$_2$" should read --$^3$Dye* + $^3$O$_2$ - - $^1$DyeO$_2$---> $^1$Dye + $^1$O$_2$-- |
| 4 | 65 | "$^3$Dye*+$^3$O$_2$- - $^1$DyeO$_2$ → $^2$Dye+$^2$.O$_2$" should read -- $^3$Dye* +$^3$O$_2$- - $^1$DyeO$_2$ ---> $^2$Dye$^+$ + $^2$•O$_2$ -- |
| 4 | 19 | " "$^1$dye". " should read --"dye".-- |
| 4 | 31 | "$^2$Dye+$^2$Sub." should read --$^2$Dye+$^2$Sub•-- |
| 4 | 34 | "(1SubH)" should read --($^1$SubH)-- |
| 4 | 36 | "$^2$Sub. state." should read --$^2$Sub• state.-- |
| 4 | 39 | "($^2$.O$_2$H)" should read --($^2$•O$_2$H)-- |

UNITED STATES PATENT AND TRADEMARK OFFICE
CERTIFICATE OF CORRECTION

PATENT NO. : 6,294,168 B1
APPLICATION NO. : 08/271583
DATED : September 25, 2001
INVENTOR(S) : R.C. Allen It is certified that error appears in the above-identified patent and that said Letters Patent is hereby corrected as shown below:

| COLUMN | LINE | ERROR |
|---|---|---|
| 4 | 41 | "$(^2.O_2-)$" should read --$(^2\bullet O_2-)$-- |
| 4 | 43 | "(or $^2.O_2-$)" should read --(or $^2\bullet O_2-$)-- |
| 4 | 49 | "$^2.O_2H+^2.O_2-$" should read --$^2\bullet O_2H+^2\bullet O_2^-$ -- |
| 4 | 65 | "$+^2.O_2$" should read --$+^2\bullet O_2$-- |
| 5 | 6 | "$^2.O_2^-$"should read --$^2\bullet O_2^-$-- |
| 5 | 21 | "Problem:" should read --Problem-- |
| 6 | 14-15 | "halop-<br>eroxidase" should break --halo-<br>peroxidase-- |
| 6 | 64 | "($^1O_3$ molecules)" should read --($10^3$ molecules)-- |
| 7 | 8 | "($^1O_3$ molecules)" should read --($10^3$ molecules)-- |
| 7 | 19 | "($^1O_3$ molecules)" should read --($10^3$ molecules)-- |
| 7 | 29 | "($^1O_3$ molecules)" should read --($10^3$ molecules)-- |
| 7 | 59 | "Agents:" should read --Agents-- |
| 9 | 40 | "In $[H_2O][X^-][H^+][\,]$" should read --In $[H_2O][X^-][H^+][^1O_2]$-- |
| 10 | 22 | "$^2H_2O_2$ - - - $(XPO)\rightarrow^2H_2O+^1O_2$" should read --$2H_2O_2$ - - - $(XPO)\rightarrow 2H_2O+^1O_2$-- |
| 11 | 33 | "peroxide Is" should read --peroxide is-- |
| 11 | 40-41 | "halop-<br>eroxidases" should break --halo-<br>peroxidases-- |
| 13 | 10 | "pmol bromide" should read --$\mu$ mol bromide-- |

UNITED STATES PATENT AND TRADEMARK OFFICE
CERTIFICATE OF CORRECTION

PATENT NO. : 6,294,168 B1
APPLICATION NO. : 08/271583
DATED : September 25, 2001
INVENTOR(S) : R.C. Allen It is certified that error appears in the above-identified patent and that said Letters Patent is hereby corrected as shown below:

| COLUMN | LINE | ERROR |
|---|---|---|
| 14 | 2-3 | "halop-eroxidase" should break --halo-peroxidase-- |
| 15 | 49 | "107" should read --$10^7$-- |
| 16 | 17 | "($_{10}$n)" should read --($10^n$)-- |
| 17 | 23 | "RBCs. 79" should read --RBCs, 79-- |
| 17 | 34 | "790 pmol" should read --790 $\mu$mol-- |
| 18 | 42 | "H2O$_2$" should read --$H_2O_2$-- |
| 22 Table 8A | 37 line 2 | "(100 $\mu$mol Cl):" should read --(100 $\mu$mol Cl$^-$):-- |
| 23 Table 8A, con't. | 4 line 2 | "(100 $\mu$mol Cl):" should read --(100 $\mu$mol Cl$^-$):-- |
| 23 Table 8B | 21 line 2 | "(10 $\mu$mol Br):" should read --(100 $\mu$mol Br$^-$):-- |
| 24 | 29-30 | "halop-eroxidase" should break --halo-peroxidase-- |
| 26 | 60 | "in the is range" should read --in the $\mu$s range-- |
| 32 | 36 | "Initially" should read --initially-- |
| 39 Table 14 | 55 line 16 | "a" should read --0-- |
| 40 | 38 | The sentence beginning "Concentrations of MPO" should begin a new paragraph |
| 45 | 41 | "Cl/H$_2$O$_2$" should read --Cl$^-$/$H_2O_2$-- |

UNITED STATES PATENT AND TRADEMARK OFFICE
CERTIFICATE OF CORRECTION

PATENT NO. : 6,294,168 B1
APPLICATION NO. : 08/271583
DATED : September 25, 2001
INVENTOR(S) : R.C. Allen It is certified that error appears in the above-identified patent and that said Letters Patent is hereby corrected as shown below:

| COLUMN | LINE | ERROR |
|---|---|---|
| 46 | 59 | "Cl/$H_2O_2$" should read --$Cl^-$/$H_2O_2$-- |
| 46 | 65 | "Br/$H_2O_2$" should read --$Br^-$/$H_2O_2$-- |
| 47 | 41 | "Br/$H_2O_2$" should read --$Br^-$/$H_2O_2$-- |
| 47 | 55 | "Br supplementation," should read --Br-supplementation,-- |
| 49 Table 19 | 27 line 15 | "Staph. aureua" should read --Staph. aureus-- |
| 51 (Claim 27, | 35 line 10) | "myeloperoxidase, eosinophil" should read --myeloperoxidase and eosinophil-- |
| 52 (Claim 37, | 20 line 10) | "myeloperoxidase, eosinophil" should read --myeloperoxidase and eosinophil-- |

Signed and Sealed this

Twenty-fourth Day of July, 2007

JON W. DUDAS
*Director of the United States Patent and Trademark Office*